US011357457B2

(12) United States Patent
Aida et al.

(10) Patent No.: US 11,357,457 B2
(45) Date of Patent: Jun. 14, 2022

(54) X-RAY DIAGNOSIS APPARATUS

(71) Applicant: Canon Medical Systems Corporation, Otawara (JP)

(72) Inventors: Takuya Aida, Nasushiobara (JP); Kunio Shiraishi, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 149 days.

(21) Appl. No.: 16/836,988

(22) Filed: Apr. 1, 2020

(65) Prior Publication Data

US 2020/0315557 A1 Oct. 8, 2020

(30) Foreign Application Priority Data

Apr. 2, 2019 (JP) .............................. JP2019-070826
Apr. 2, 2019 (JP) .............................. JP2019-070829

(51) Int. Cl.
*A61B 6/00* (2006.01)
(52) U.S. Cl.
CPC .......... *A61B 6/4021* (2013.01); *A61B 6/4035* (2013.01); *A61B 6/487* (2013.01); *A61B 6/50* (2013.01); *A61B 6/5205* (2013.01); *A61B 6/542* (2013.01)
(58) Field of Classification Search
CPC ......... A61B 6/032; A61B 6/542; A61B 6/484; A61B 6/06; A61B 6/4007; A61B 6/4021; H01J 35/147
See application file for complete search history.

(56) References Cited

U.S. PATENT DOCUMENTS

| 4,763,343 A * | 8/1988 | Yanaki ................... A61B 6/502 378/110 |
| 2007/0258564 A1 | 11/2007 | Gaudin et al. |
| 2012/0039443 A1 | 2/2012 | Behling |
| 2013/0142304 A1 | 6/2013 | Shiraishi et al. |
| 2014/0112441 A1* | 4/2014 | Becker ................... A61B 6/482 378/62 |
| 2015/0139382 A1 | 5/2015 | Hyung et al. |

(Continued)

FOREIGN PATENT DOCUMENTS

| JP | 2013-116184 A | 6/2013 |
| JP | 2015-097782 A | 5/2015 |

(Continued)

OTHER PUBLICATIONS

Extended European Search Report dated Aug. 12, 2020 in corresponding European Patent Application No. 20167574.1, 8 pages.

*Primary Examiner* — Courtney D Thomas
(74) *Attorney, Agent, or Firm* — Oblon, McClelland, Maier & Neustadt, L.L.P.

(57) ABSTRACT

According to one embodiment, an X-ray diagnosis apparatus includes an X-ray tube, an X-ray detector, an operating unit, and processing circuitry. The processing circuitry determines a focal-spot size of X-rays in second moving picture imaging after first moving picture imaging, based on an output of the X-ray detector in the first moving picture imaging, and determines a focal-spot size of X-rays in third moving picture imaging after the second moving picture imaging, based on an output of the X-ray detector in the second moving picture imaging.

20 Claims, 14 Drawing Sheets

(56) References Cited

U.S. PATENT DOCUMENTS

| | | | |
|---|---|---|---|
| 2015/0325011 A1* | 11/2015 | Ashida | A61B 6/504 382/131 |
| 2018/0000438 A1 | 1/2018 | Abe et al. | |
| 2018/0235564 A1 | 8/2018 | Jain et al. | |

FOREIGN PATENT DOCUMENTS

| | | |
|---|---|---|
| JP | 2015-226764 A | 12/2015 |
| JP | 2018-000380 A | 1/2018 |
| JP | 2018-134417 A | 6/2018 |
| WO | WO 2010/128416 A2 | 11/2010 |

\* cited by examiner

| X-ray conditions (maximum power)[kW] | Dose limit [mGy/min] | SID[cm] | Body thickness [cm]≤5 | 5<Body thickness [cm]≤15 | 15<Body thickness [cm]≤25 | 25<Body thickness [cm] |
|---|---|---|---|---|---|---|
| 3.0 | 50 | SID≤100 | Filter A | Filter A | Filter A | Filter A |
|  |  | 100<SID≤120 |  |  | Filter B | Filter B |
|  |  | 120<SID |  |  | Filter C | Filter C |
|  | 87 | SID≤100 | Filter A | Filter A | Filter B | Filter B |
|  |  | 100<SID≤120 |  |  | Filter A | Filter C |
|  |  | 120<SID |  |  | Filter A | Filter C |
|  | 125 | SID≤100 | Filter A | Filter B | Filter B | Filter D |
|  |  | 100<SID≤120 |  |  | Filter C | Filter D |
|  |  | 120<SID |  |  | Filter C | Filter D |

F I G. 10

| X-ray conditions (maximum power)[kW] | Dose limit [mGy/min] | SID[cm] | Body thickness [cm]≤5 | 5<Body thickness [cm]≤15 | 15<Body thickness [cm]≤25 | 25<Body thickness [cm] |
|---|---|---|---|---|---|---|
| 3.0 | 50 | SID≤100 | Filter A | Filter B | Filter B | Filter B |
| | | 100<SID≤120 | | | Filter B | Filter C |
| | | 120<SID | | | Filter B | Filter C |
| | 87 | SID≤100 | Filter A | Filter B | Filter B | Filter C |
| | | 100<SID≤120 | | | Filter C | Filter D |
| | | 120<SID | | | Filter C | Filter D |
| | 125 | SID≤100 | Filter A | Filter B | Filter C | Filter D |
| | | 100<SID≤120 | | | Filter C | Filter D |
| | | 120<SID | | | Filter C | Filter D |

F I G. 11

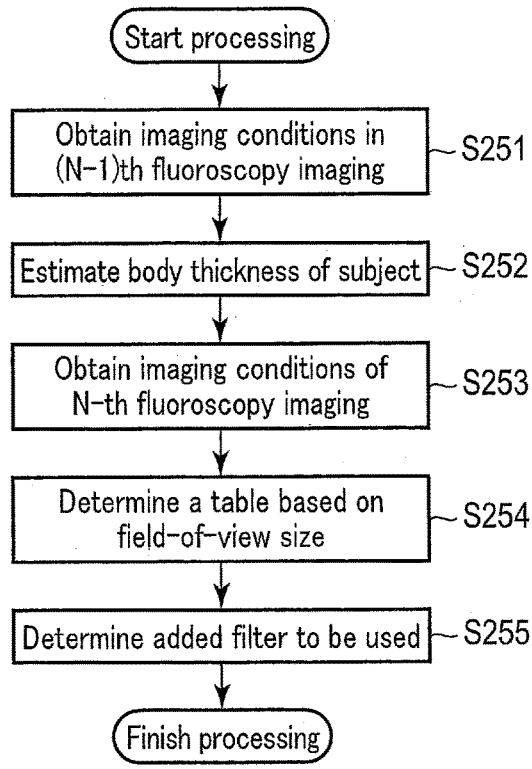
F I G. 14
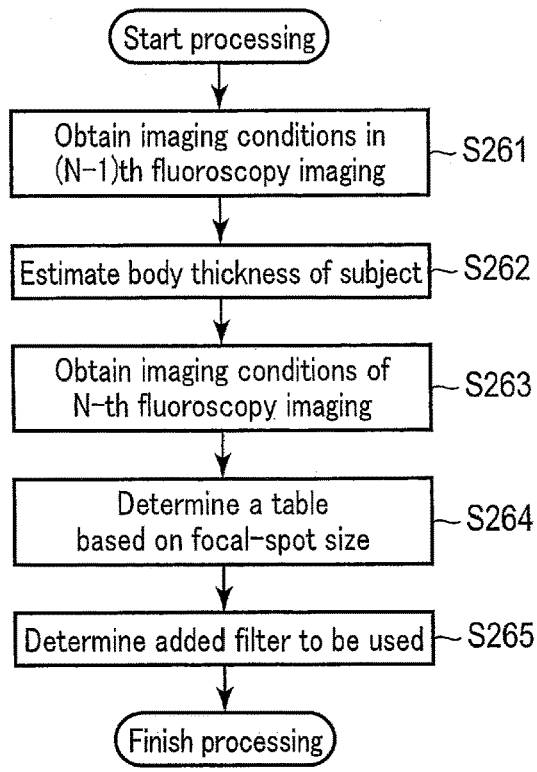
F I G. 15

X-RAY DIAGNOSIS APPARATUS

CROSS-REFERENCE TO RELATED APPLICATIONS

This application is based upon and claims the benefit of priority from the prior Japanese Patent Application No. 2019-070826, filed Apr. 2, 2019 and the prior Japanese Patent Application No. 2019-070829, filed Apr. 2, 2019; the entire contents of all of which are incorporated herein by reference.

FIELD

Embodiments described herein relate generally to an X-ray diagnosis apparatus.

BACKGROUND

Conventionally, during a single fluoroscopy examination using a circulatory system X-ray diagnosis apparatus, an operator interrupts and resumes fluoroscopy imaging in accordance with a progression of a device such as catheter, so that a plurality of fluoroscopy imaging sessions are intermittently performed. In a single fluoroscopy imaging session, a tube voltage, a tube current, and a pulse width are controlled at appropriate values through feedback control, regardless of the progression of the device. On the other hand, as a size of focal spot of X-rays (which will be referred to as "focal-spot size" hereinafter), a fixed value may be continuously used, or manually set by an operator at timing when fluoroscopy imaging is switched from a last session to a next session. Along with this, if the thickness of a subject body has been changed as the device progresses during the last fluoroscopy imaging session, for example, it may be that an appropriate focal-spot size is not selected in the next fluoroscopy imaging session.

BRIEF DESCRIPTION OF THE DRAWINGS

FIG. 10 is a diagram showing an example of a correspondence table used in the filter selecting processing by the X-ray diagnosis apparatus according to the fifth embodiment, providing a relationship of a maximum power, a dose limit, an SID, and a body thickness, to an added filter to be used.

FIG. 11 is a diagram showing an example of a correspondence table used in the filter selecting processing by the X-ray diagnosis apparatus according to the fifth embodiment, providing a relationship of a maximum power, a dose limit, an SID, and a body thickness, to an added filter to be used.

FIG. 14 is a flowchart illustrating a processing procedure of filter selecting processing performed by an X-ray diagnosis apparatus according to an eighth embodiment.

FIG. 15 is a flowchart illustrating a processing procedure of filter selecting processing performed by an X-ray diagnosis apparatus according to a ninth embodiment.

DETAILED DESCRIPTION

According to one embodiment, an X-ray diagnosis apparatus includes an X-ray tube that generates X-rays, an X-ray detector that detects X-rays generated by the X-ray tube, an operating unit that instructs performance of moving picture imaging using the X-ray tube and the X-ray detector and processing circuitry. The processing circuitry determines a condition of X-ray irradiation by the X-ray tube. The processing circuitry is configured to determine a focal-spot size of X-rays in second moving picture imaging performed in accordance with an operation input to the operating unit after first moving picture imaging, based on an output of the X-ray detector in the first moving picture imaging performed in accordance with an operation input to the operating unit, and determine a focal-spot size of X-rays in third moving picture imaging performed in accordance with an operation input to the operating unit after the second moving picture imaging, based on an output of the X-ray detector in the second moving picture imaging.

Hereinafter, the embodiments of the X-ray diagnosis apparatus will be explained in detail with reference to the accompanying drawings. In the description hereinafter, structural elements having substantially the same functions and configurations will be denoted by the same reference symbols, and a duplicate description of such elements will be given only where necessary. The X-ray diagnosis apparatus according to the embodiments described hereinafter may be a single-modality apparatus, or a composite-modality apparatus, such as an angio CT apparatus, etc., for example.

First Embodiment

Figure 1:
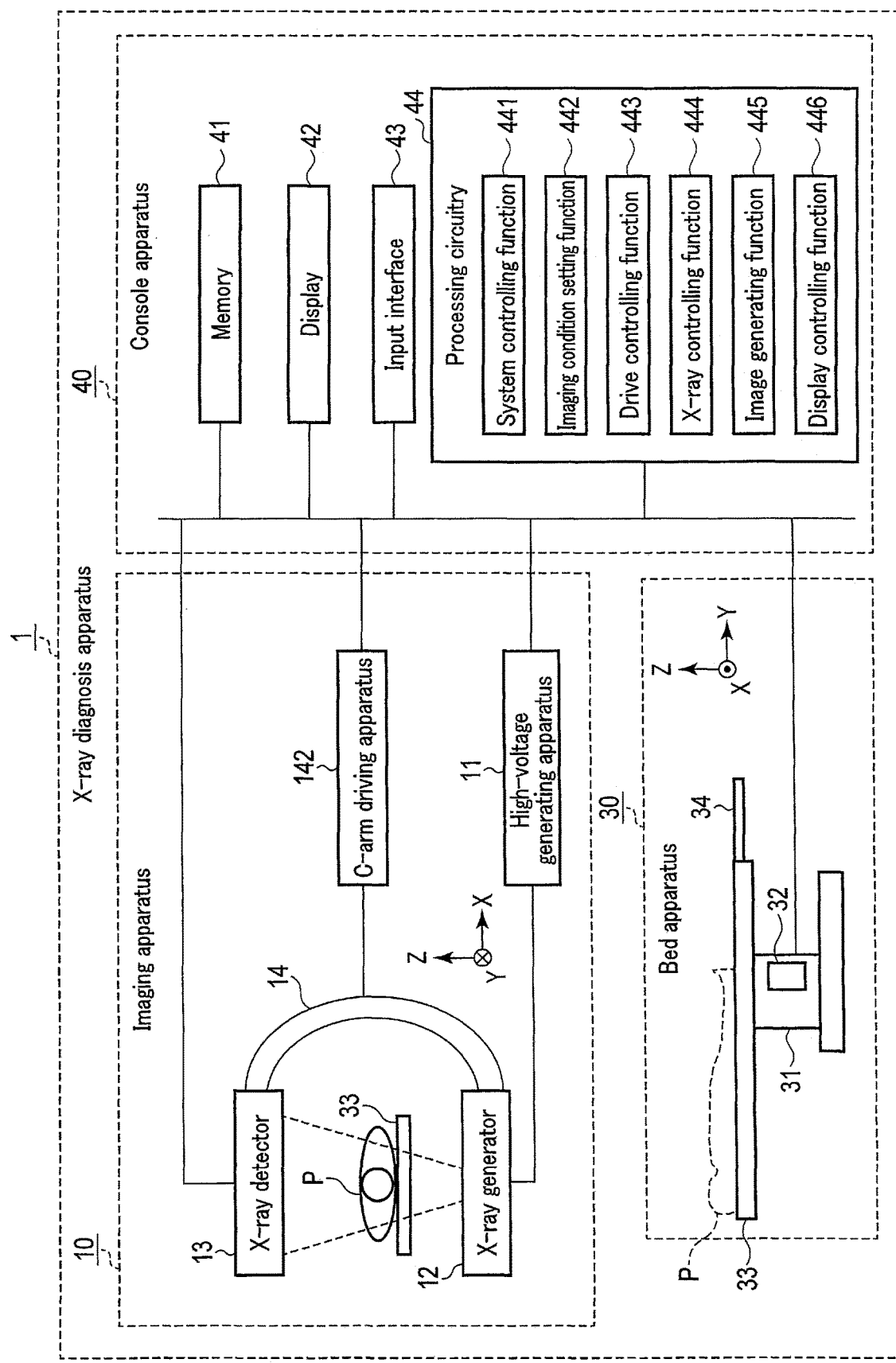
FIG. 1 is a diagram illustrating a configuration of an X-ray diagnosis apparatus according to a first embodiment.

FIG. 1 is a drawing showing the configuration example of an X-ray diagnosis apparatus 1 according to the first embodiment. As shown in FIG. 1, the X-ray diagnosis apparatus 1 has an imaging apparatus 10, a bed apparatus 30, and a console apparatus 40. The imaging apparatus 10 has a high voltage generating apparatus 11, an X-ray generator 12, an X-ray detector 13, a C-arm 14, and a C-arm driving apparatus 142.

The high voltage generating apparatus 11 generates a high voltage to be applied between an anode and a cathode, and outputs the high voltage to an X-ray tube, so that thermoelectrons generated from the cathode of the X-ray tube are accelerated.

The X-ray generator 12 has an X-ray tube that irradiates a subject P with X-rays, a plurality of filters having a function of attenuating or reducing an amount of irradiation X-ray (hereinafter "additional filters"), and an X-ray diaphragm.

The X-ray tube is a vacuum tube that generates X-rays. The X-ray tube has a tube bulb, a filament (cathode) provided on the tube bulb, and a tungsten anode. The X-ray tube accelerates the thermoelectrons released from the filament by the high voltage. The X-ray tube generates X-rays by making the accelerated electrons collide with the tungsten anode.

In the present embodiment, filaments of two types having different sizes of a focal spot (effective focal spot) of the generated X-rays (hereinafter, "focal-spot size") are provided. In accordance with an input by an operator via an input interface 43 (which will be described later), or by setting in a processing circuitry 44 (which will also be described later), a filament to be used is selected from the two filaments, and the filament being used is switched to another by the driving of a driving apparatus (not shown). Furthermore, a focal-spot size is switched between a small size and a medium size through the switching of the filament to be used. The medium focal spot is larger than the small focal spot. The small focal spot is a value in the range of 0.2 to 0.4 mm, for example. The medium focal spot is a value in the range of 0.5 to 0.7 mm, for example. The small focal spot is an example of a first focal-spot size. The medium focal spot is an example of a second focal-spot size.

In the present embodiment, these two types of focal-spot size, namely the small and medium sizes, can be set; however, three or more sizes can be set. In this case, filaments of the number corresponding to the number of possible focal-spot sizes are provided.

The additional filters are made of a metal plate, such as copper or aluminum, for example. The additional filters are inserted between the X-ray tube and the X-ray diaphragm to remove a long wavelength component (soft X-ray) of a continuous spectrum X-ray generated by the X-ray generator 12 in accordance with a thickness of each added filter. The thickness of each added filter is a value in the range of 0.1 to 5 mm, for example. The added filter may be called an "X-ray filter", "a filtering plate", "a beam filter", "a radiation quality filter", or "a beam spectrum filter". The added filter hardens a radiation quality of the X-rays generated in the X-ray generator 12 by removing the long wavelength component in accordance with its thickness. The added filter is also capable of removing an energy component of X-rays unnecessary for X-ray diagnosis. It is thereby possible for the added filter to adjust the radiation quality of the X-rays generated by the X-ray generator 12.

In the present embodiment, four additional filters (filters A through D) are provided. Filters A through D have different thicknesses. For this reason, filter A through filter D have a different soft X-ray removal rate (hereinafter, "X-ray reduction rate"). A thick added filter (added filter having a large thickness) has a greater X-ray reduction rate than that of a thin added filter (added filter having a small thickness). The thickness of filter A is larger than the thickness of filter B, the thickness of filter B is larger than the thickness of filter C, and the thickness of filter C is larger than the thickness of filter D. For this reason, the X-ray reduction rate of filter A is larger than that of filter B, the X-ray reduction rate of filter B is larger than that of filter C, and the X-ray reduction rate of filter C is larger than that of filter D.

The driving apparatus inserts, between the X-ray tube and the X-ray diaphragm, an added filter selected from the plurality of additional filters, in accordance with an input by an operator via an input interface 43 (described later), or setting in a processing circuitry 44 (described later). The thickness of the added filter is adjusted through the act of switching the added filter to be inserted between the X-ray tube and the X-ray diaphragm. In other words, the driving apparatus inserts at least one of the additional filters into a path from the focal spot of the X-ray tube and the X-ray detector 13. The driving apparatus is an example of a filter driving unit.

The X-ray diaphragm is located between the X-ray tube and the X-ray detector 13, and is made of a lead plate, which serves as a metal plate. The X-ray diaphragm cuts X-rays outside an opening area, thereby limiting the X-rays generated by the X-ray tube and irradiating only a region of interest for the subject P with the limited X-rays, so that a size of an X-ray irradiation area (X-ray irradiation field) is adjusted (hereinafter, "field-of-view size"). For example, the X-ray diaphragm has four diaphragm wings, and adjusts the area from which X-rays are cut into a desired size so as to adjust a field-of-view size by sliding these diaphragm wings. The diaphragm wings of the X-ray diaphragm are driven by a driving apparatus (not shown) in accordance with the region of interest that has been input by the operator with the input interface 43.

The X-ray detector 13 detects X-rays emitted from the X-ray tube which have passed through the subject P. As the X-ray detector 13, both an X-ray detector capable of directly converting X-rays into electric charge and an X-ray detector capable of converting X-rays into light and subsequently into electric charge can be adopted, and the former detector will be described hereinafter as an example; however, the latter detector can also be adopted. In other words, the X-ray detector 13 has a flat panel detector (FPD) that converts X-rays passed through the subject P into electric charge and accumulates the electric charge, and a gate driver that generates a drive pulse for reading the electric charge accumulated in this FPD. The size of the FPD falls within the range of 8 to 16 inches, for example. The FPD is comprised of micro detection elements, which are two-dimensionally arranged in a row direction and a line direction. Each of the detection elements has a photoelectric film that senses X-rays and generates electric charge in accordance with an amount of incident X-rays, an electric charge accumulating capacitor that accumulates electric charge generated on the photoelectric film, and a TFT (thin-film transistor) that outputs the electric charge accumulated on the electric charge accumulating capacitance at predetermined timing. The accumulated electric charge is sequentially read by a drive pulse supplied by the gate driver. The size of each detection element of the FPD (hereinafter, the element will be referred to as "FPD detection element", and the size will be referred to as "FPD element size") is a value falling under the range of 130 to 200 μm. The FPD element size is not limited to this example, and may be in a micro size, such as 76 μm per side, for example.

The C-arm 14 has a structure that allows the C-arm 14 to hold the X-ray generator 12 and the X-ray detector 13 in such a manner that they are opposed to each other with the subject P and the top plate 33 being interposed therebetween, so that X-ray imaging of the subject P who lays on the top plate 33 can be performed. The C-arm 14 is slidably and rotatably supported with respect to each of the plurality of rotation axes. The C-arm 14 is provided with a plurality of power sources at locations suitable for realizing sliding or rotation operations. These power sources constitute a C-arm driving apparatus 142. The C-arm driving apparatus 142 reads a drive signal from a drive controlling function 443 (which will be described later) to cause the C-arm 14 to slide, rotate, or move linearly.

The bed 30 is a device for placing the subject P and moving the subject P thereon, and includes a base 31, a bed driving apparatus 32, a top plate 33, and a support frame 34.

The base 31 is a case placed on the floor and supporting the support frame 34 movably in the vertical direction (a Z-axis direction).

The bed driving apparatus 32 is a motor or actuator stored in the case of the bed 30, and which moves the table top 33 on which the subject P is placed in the longitudinal direction of the top plate 33 (a Y-axis direction). The bed driving apparatus 32 reads a drive signal from the drive controlling function 443, and moves the top plate 33 in a horizontal direction or a vertical direction with respect to the floor. The positional relationship between the subject P and the imaging axis changes when the C-arm 14 or the top plate 33 moves. The bed driving apparatus 32 may not only move the top plate 33 but also the support frame 34 in the longitudinal direction of the top plate 33.

The top plate 33 is a plate provided on the top surface of the support frame 34 and on which the subject P is placed.

The support frame 34 is provided above the base 31, and slidably supports the top plate 33 in its longitudinal direction.

In the bed 30, the top plate 33 may be movable with respect to the support frame 34, or the top plate 33 and the support frame 34 may be movable together with respect to the base 31.

The console apparatus 40 includes a memory 41, a display 42, an input interface 43, and processing circuitry 44. Hereinafter, the console apparatus 40 will be described as a device separate from the imaging apparatus 10; however, the console apparatus 40 or some of the structural elements thereof may be incorporated in the imaging apparatus 10. The console apparatus 40 is, for example, a medical image processing apparatus.

Hereinafter, the console apparatus 40 will be described as an apparatus performing a plurality of functions with a single console; however, it is possible to perform a plurality of functions with separate consoles. For example, the functions of the processing circuitry 44, such as an image generating function 445 (described later) may be distributed between different console devices and thereby implemented.

The memory 41 is a storage device such as an HDD, an SSD, or an integrated circuit storage unit, etc., configured to store various kinds of information. The memory 41 may be a portable storage medium, such as a CD (compact disc), a DVD (digital versatile disc), or a flash memory, other than an HDD or SDD, etc. Alternatively, the memory 41 may be a drive apparatus that writes and reads various types of information in and from a semiconductor memory, such as a flash memory or a random access memory (RAM), etc. The storage area of the memory 41 may be in the X-ray diagnosis apparatus 1, or in an external storage device connected via a network.

The memory 41 stores X-ray images, programs executed by the processing circuitry 44, and various types of data used for the processing in the processing circuitry 44, for example. The memory 41 is an example of a storage unit.

The display 42 displays various types of information. For example, the display 42 outputs medical images (X-ray images) generated by the processing circuitry 44, and a graphical user interface (GUI) or the like for receiving various types of operations from the operator. For example, the display 42 is a liquid crystal display or a CRT (cathode ray tube) display. The display 42 is an example of a display unit. The display 42 may be provided on an imaging apparatus 10. The display 42 may be a desktop type, or comprised of a tablet device, etc. capable of wireless communication with the main body of the console apparatus 40.

The input interface 43 receives various types of input operations from the operator, converts a received input operation into an electrical signal, and outputs the electrical signal to the processing circuitry 44. For example, the input interface 43 receives subject information, imaging conditions, inputs of various types of command signals, etc. from an operator. For example, the input interface 43 is realized by a track ball, a mouse, a keyboard, switches, buttons, a joy stick, a touch pad that allows input operations through a touch on an operation screen, a touch-panel display in which a display screen and a touch pad are integrated, or a foot switch, and the like, which are all designed to instruct the movement of the C-arm 14, set a region of interest (ROI), and perform fluoroscopy imaging, etc. The input interface 43 is an example of an input unit and an operation unit. The input interface 43 may be provided in the imaging apparatus 10. The input interface 43 may be configured as a tablet device capable of communicating wirelessly with the console apparatus 40. The interface 43 is not limited to a device having physical operational components, such as a mouse and a keyboard, etc. For example, examples of the input interface 43 also include electrical signal processing circuitry that receives an electrical signal corresponding to an input operation from an external input device provided separately from the apparatus, and outputs the electrical signal to the processing circuitry 44. The input interface 43 is an example of an operating unit that instructs the operator to perform moving picture imaging using the X-ray tube and the X-ray detector 13.

The processing circuitry 44 controls the entire operation of the X-ray diagnosis apparatus 1. The processing circuitry 44 is a processor that invokes a program in the memory 41 and performs a system controlling function 441, an imaging condition setting function 442, a drive controlling function 443, an X-ray controlling function 444, an image generating function 445, and a display controlling function 446.

FIG. 1 illustrates the case where the system controlling function 441, the imaging condition setting function 442, the drive controlling function 443, the X-ray controlling function 444, the image generating function 445, and the display controlling function 446 are realized in a single processing circuitry 44; however, the processing circuitry may be constituted by a combination of a plurality of independent processors, and the functions may be realized by the processors executing the programs. The system controlling function 441, the imaging condition setting function 442, the drive controlling function 443, the X-ray controlling function 444, the image generating function 445 and the display controlling function 446 may be respectively referred to as "system controlling circuitry", "imaging condition setting circuitry", "drive controlling circuitry", "X-ray controlling circuitry", "image processing circuitry", and "display controlling circuitry"; furthermore, each of those functions may be implemented as individual hardware circuitry.

The term "processor" used in the above explanation means, for example, circuitry such as a CPU (central processing unit), a GPU (graphics processing unit), an ASIC, or a programmable logic device (for example, an SPLD (simple programmable logic device), a CPLD (complex programmable logic device), or an FPGA (field programmable gate array)). The processor realizes its function by reading and executing the program stored in the storage circuitry. Instead of storing a program on the memory circuitry, the program may be directly integrated into the circuitry of the processor. In this case, the function is activated by the reading and execution of the program integrated into the circuitry. Each processor of the present embodiment is not limited to a case where it is configured as a single circuit in itself; a plurality of independent circuits may be combined into one processor to realize the function of the processor. Furthermore, a plurality of constituent elements shown in FIG. 1 may be integrated into one processor to realize the function.

The processing circuitry 44 controls, through the system controlling function 441, each of the plurality of structural elements of the X-ray diagnosis apparatus 1 based on an input operation received from the operator via the input interface 43. For example, the processing circuitry 44 controls the structural elements of the imaging apparatus 10 in accordance with imaging conditions. The processing circuitry 44 that enables the system controlling function 441 is an example of a system control unit.

The processing circuitry 44 sets conditions for imaging (hereinafter, "imaging conditions") through the imaging condition setting function 442. Fluoroscopy imaging is an example of moving picture imaging. The processing circuitry 44 that enables the imaging condition setting function 442 is an example of an imaging condition setting unit.

The imaging conditions include at least one of the following: a condition for X-ray irradiation by an X-ray tube (hereinafter, "X-ray condition"), an AGC magnification of AGC (auto gain control) (hereinafter, "AGC magnification"), information regarding an added filter used (hereinafter "filter specifying information"), a detector spatial resolution, a field-of-view size, a source-image distance ("SID"), or an area in an FPD used to constitute one pixel of an X-ray image (hereinafter, "FPD pixel size"). The filter specifying information includes at least one of a type of the added filter used, or a thickness of the added filter used, etc. The imaging conditions may be referred to as "fluoroscopy imaging conditions". The imaging condition setting function 442 is an example of an X-ray condition determining unit that determines the X-ray conditions.

The X-ray conditions include at least one of a tube current, a tube voltage, a focal-spot size, a pulse width, or a pulse rate (the number of pulse per unit time), for example.

The processing circuitry 44 determines, through the imaging condition setting function 442, a size of a focal spot of X-rays in a fluoroscopy imaging session to be performed next based on the output of the X-ray detector 13 in the fluoroscopy imaging session performed immediately prior, in an examination including multiple fluoroscopy imaging sessions. The processing circuitry 44 sets a focal-spot size of X-rays in accordance with the determined result. Herein, the focal-spot size may either numerical value or setting parameter like as "small focal spot" or "medium focal spot" etc. The focal-spot size may be determined and set as a "small focal spot" or "medium focal spot". Alternatively, when a control grid electrode is used, the focal-spot size may be determined and set as a value within the range of 0.2 to 0.7 mm, for example. Alternatively, the focal-spot size may be determined as a value within the range of 0.2 to 0.4 mm, and set as a small focal spot. Alternatively, the focal-spot size can be determined as a value within the range of 0.5 to 0.7 mm, and set as a medium focal spot.

Specifically, the processing circuitry 44 determines, through the imaging condition setting function 442, a focal-spot size in a second fluoroscopy imaging session performed in accordance with an operation input to the input interface 43 after a first fluoroscopy imaging session, based on an output of the X-ray detector 13 in the first fluoroscopy imaging session performed in accordance with an operation input to the input interface 43, and determines a focal-spot size in a third fluoroscopy imaging session performed in accordance with an operation input to the input interface 43 after the second fluoroscopy imaging session, based on an output of the X-ray detector 13 in the second fluoroscopy imaging. To be more precise, in the first moving picture imaging and the second moving picture imaging, for example, the processing circuitry 44 sets at least one of the X-ray irradiation condition or a gain to be applied to an X-ray image in a following frame, based on an output of the X-ray detector 13 in a prior frame. Furthermore, the processing circuitry 44 determines a focal-spot size of X-rays in the second moving picture imaging based on an output of the X-ray detector 13 in the first moving picture imaging, through the conditions of X-ray irradiation in the first moving picture imaging. Similarly, the processing circuitry 44 determines a focal-spot size of X-rays in the third moving picture imaging based on an output of the X-ray detector 13 in the second moving picture imaging, through the conditions of X-ray irradiation in the second moving picture imaging.

The processing circuitry 44 may obtain the X-ray conditions in the first fluoroscopy imaging based on an X-ray image generated by the output of the X-ray detector 13 in the first fluoroscopy imaging, and determine a focal-spot size in the second fluoroscopy imaging based on the X-ray conditions in the first fluoroscopy imaging. The first fluoroscopy imaging is an example of the first moving picture imaging, the second fluoroscopy imaging is an example of the second moving picture imaging, and the third fluoroscopy imaging is an example of the third moving picture imaging.

The processing circuitry 44 controls, through the drive controlling function 443, the C-arm driving apparatus 142 and the bed driving apparatus 32 based on, for example, information regarding the driving of the C-arm 14 and the top plate 33, which is input from the input interface 43. The processing circuitry 44 that enables the drive controlling function 443 is an example of a drive controlling unit.

The processing circuitry 44, through the X-ray controlling function 444 reads, for example, the information from the system controlling function 441, and controls the X-ray conditions, such as a tube current, a tube voltage, a focal-spot size, an irradiation time, and a pulse width, etc. in the high voltage generating apparatus 11. The X-ray controlling function 444 may include a function of selecting a filament to be used from a plurality of filaments provided in the tube bulb of the X-ray tube based on the focal-spot size of X-rays determined by the imaging condition setting function 442. The processing circuitry 44 that enables the X-ray controlling function 444 is an example of an X-ray controlling unit.

The processing circuitry 44 generates, by the image generating function 445, an X-ray image based on data output from the X-ray detector 13, for example. At this time, the processing circuitry 44 performs AGC (auto gain control). The AGC is a control to adjust brightness of a generated X-ray image in order to keep the brightness constant. To be more precise, the AGC is a control of an upper limit of an entrance dose of X-rays to the subject per unit time (hereinafter, "dose limit"), or a digital gain applied to an entire image in order to secure the brightness of the X-ray image in a case when a detector entrance dose cannot be secured because of the tube bulb output limit. The AGC magnification is a ratio of a brightness of a post-adjustment X-ray image to a pre-adjustment X-ray image made by the AGC. The processing circuitry 44 may perform various types of synthesis processing or subtraction processing on the generated X-ray image. The X-ray image is an example of medical data. The processing circuitry 44 that enables the image generation function 445 is an example of an image generating unit.

The processing circuitry 44, through the display controlling function 446, reads a signal from the system controlling function 441, and displays a desired X-ray image obtained from the memory 41 on the display 42. The processing circuitry 44 that enables the X-ray controlling function 446 is an example of a display controlling unit.

Next, an operation of fluoroscopy imaging performing processing performed by the X-ray diagnosis apparatus 1 will be described. The fluoroscopy imaging performing processing is processing to perform fluoroscopy imaging on a subject during an examination, in accordance with an operation input via the input interface 43.

The processing procedure in the fluoroscopy imaging performing processing which will be described below is merely an example, and the processing can be changed as far as is reasonably possible. Omission, replacement, or addition of a step in the processing procedure described hereinafter can be made as appropriate, in accordance with an actual situation where the present embodiment is realized.

Figure 2:
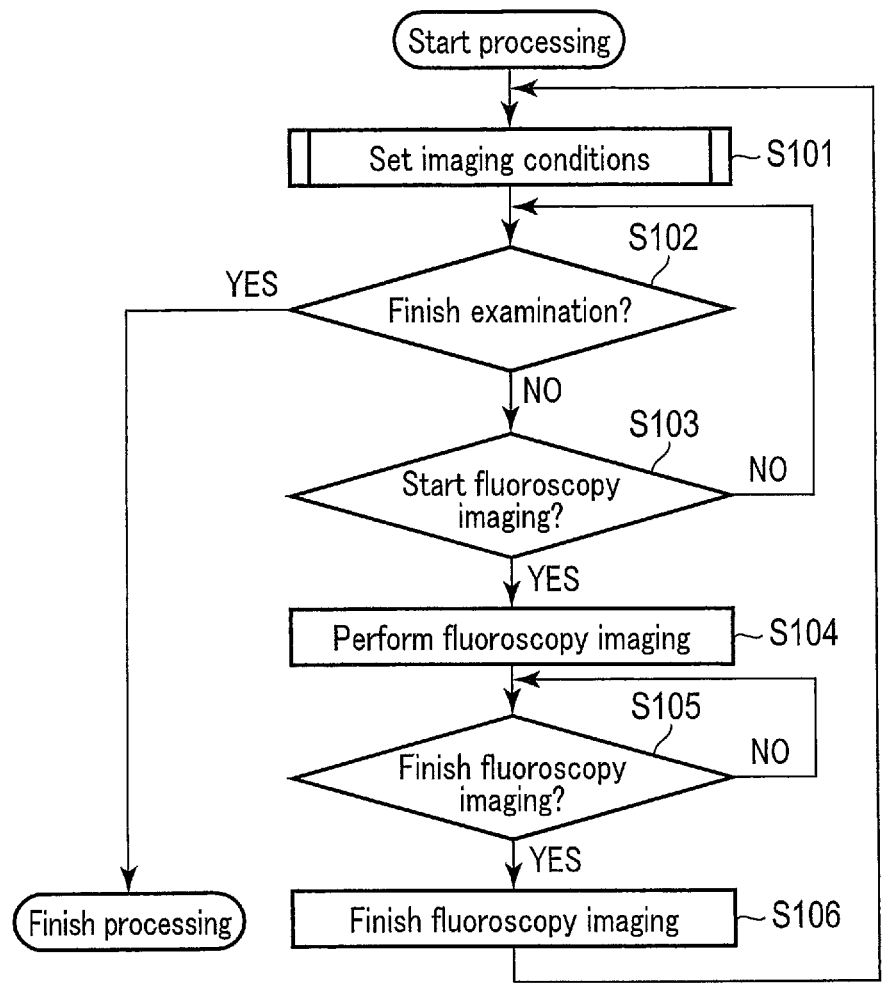
FIG. 2 is a flowchart illustrating a processing procedure of fluoroscopy imaging performing processing performed by the X-ray diagnosis apparatus according to the first embodiment.

FIG. 2 is a flowchart showing an example of a procedure of the fluoroscopy imaging performing processing according to the present embodiment. The processing circuitry 44 commences the fluoroscopy imaging performing processing upon an input of an instruction to commence an examination via the input interface 43.

(Fluoroscopy Imaging Performing Processing)
(Step S101)

The processing circuitry 44 performs the imaging condition setting function 442. The processing circuitry 44, through the imaging condition setting function 442, performs processing to set imaging conditions in fluoroscopy imaging performed next (this processing will be referred to as "imaging condition setting processing" hereinafter). The details of the image condition setting processing will be described later.

(Step S102)

The processing circuitry determines whether or not an instruction to finish an examination of a subject is input. At this time, the processing circuitry 44 detects, for example, an input of the instruction to finish an examination of a subject in the input interface 43 so as to determine whether or not the instruction to finish the examination has been input. If the instruction to finish an examination has been input (Yes in step S102), the processing circuitry 44 finishes the fluoroscopy imaging performing processing.

If the instruction to finish an examination has not been input (No in step S102), the processing proceeds to step S103.

(Step S103)

The processing circuitry 44 determines whether or not an instruction to perform fluoroscopy imaging has been input in accordance with an operator's operation of the input interface 43. At this time, the processing circuitry 44 detects, for example, whether or not a foot switch is operated so as to determine whether or not an instruction to perform fluoroscopy imaging has been input. If the instruction to perform (commence) fluoroscopy imaging (Yes in step S103), the processing proceeds to step S104. If the instruction to perform (commence) fluoroscopy imaging is not input (No in step S103), the processing returns to step S103, and the processing circuitry 44 waits until the instruction to finish an examination is input or until the instruction to perform (commence) the fluoroscopy imaging is input.

(Step S104)

The processing circuitry 44 performs the fluoroscopy imaging using the imaging apparatus 10, through performance of the system controlling function 441, the drive controlling function 443, the X-ray controlling function 444, and the image generating function 445.

During a single session of fluoroscopy imaging, the processing circuitry 44 generates, through the image generating function 445, a plurality of X-ray images, which are frames in a chronological order, and causes the memory 41 to store the generated X-ray images. Then, the processing circuitry 44 causes, through the display controlling function 446, the display 42 to display the X-ray moving images generated from the generated X-ray images. At this time, the processing circuitry 44 performs the AGC through the image generating function 445.

The processing circuitry 44 performs, through the system controlling function 441 and the X-ray controlling function 444, control to set X-ray conditions in a later frame during the fluoroscopy imaging based on the output of the X-ray detector 13 in a previous frame. In other words, during a single session of fluoroscopy imaging, the processing circuitry 44 conducts feedback control to change the X-ray conditions, etc. based on a change in subject conditions. For example, in the feedback control, when a body thickness or a structure of internal tissue of the subject changes due to an operation of moving the top plate 33 on which the subject is laid, the processing circuitry 44 detects brightness and contrast, etc. of an X-ray image generated in a previous frame, and controls at least one of a tube voltage, a tube current, a pulse width, or an AGC magnification, so that brightness and contrast, etc. of an X-ray image displayed in a later frame satisfy predetermined conditions. With this feedback control, a tube voltage, a tube current, a pulse width, and an AGC magnification can be selected as appropriate, even when the subject conditions are changed during a single session of fluoroscopy imaging. Accordingly, when the fluoroscopy imaging is finished, at least one of the tube voltage, the tube current, the pulse width, and the AGC magnification is appropriately controlled according to the change in the subject conditions. Furthermore, a last X-ray image generated during a single session of fluoroscopy imaging is controlled so that its brightness and contrast, etc. satisfy predetermined conditions.

(Step S105)

The processing circuitry 44 determines whether or not an instruction to finish fluoroscopy imaging has been input. At this time, the processing circuitry 44 detects, for example, whether or not a foot switch is operated so as to determine whether or not an instruction to finish the fluoroscopy imaging has been input. If the instruction to finish the fluoroscopy imaging (Yes in step S105), the processing proceeds to step S106. The processing circuitry 44 continues the fluoroscopy imaging in step S104 until an instruction to finish the fluoroscopy imaging is input.

(Step S106)

The processing circuitry 44 finishes the fluoroscopy imaging using the imaging apparatus 10, through performance of the system controlling function 441, the drive controlling function 443, the X-ray controlling function 444, and the image generating function 445. When the fluoroscopy imaging by the X-ray imaging is finished, the processing returns to step S101.

The processing circuitry 44 performs the imaging condition setting processing upon the conclusion of the fluoroscopy imaging by the X-ray imaging, and sets imaging conditions of fluoroscopy imaging to be performed next. Specifically, the processing circuitry 44 determines a focal-point size of X-rays in the second moving picture imaging upon the finish of the first moving picture imaging, and determines a focal-point size of X-rays in the third moving picture imaging upon the conclusion of the second moving picture imaging. Furthermore, the processing circuitry 44 determines whether or not an instruction to finish the examination in step S102 is given only after imaging conditions in fluoroscopy imaging to be performed next are set in step S101. Thus, even when the next fluoroscopy imaging is not performed because of the finish of the examination, imaging conditions in the impending fluoroscopy imaging are still set.

As described above, in the fluoroscopy imaging performing processing, the processing circuitry 44 commences fluoroscopy imaging when the instruction to perform fluoroscopy imaging is input via the input interface 43. The processing circuitry 44 finishes fluoroscopy imaging when the instruction to perform fluoroscopy imaging is canceled in the input interface 43. Then, when the instruction to perform fluoroscopy imaging is once again input at the input interface 43, the processing circuitry 44 performs a next fluoroscopy imaging session. During the performance of a single fluoroscopy imaging session, the processing circuitry 44 controls the imaging conditions so as to secure image quality of an X-ray image as appropriate based on the change in the subject conditions.

(Imaging Condition Setting Processing)

Figure 3:
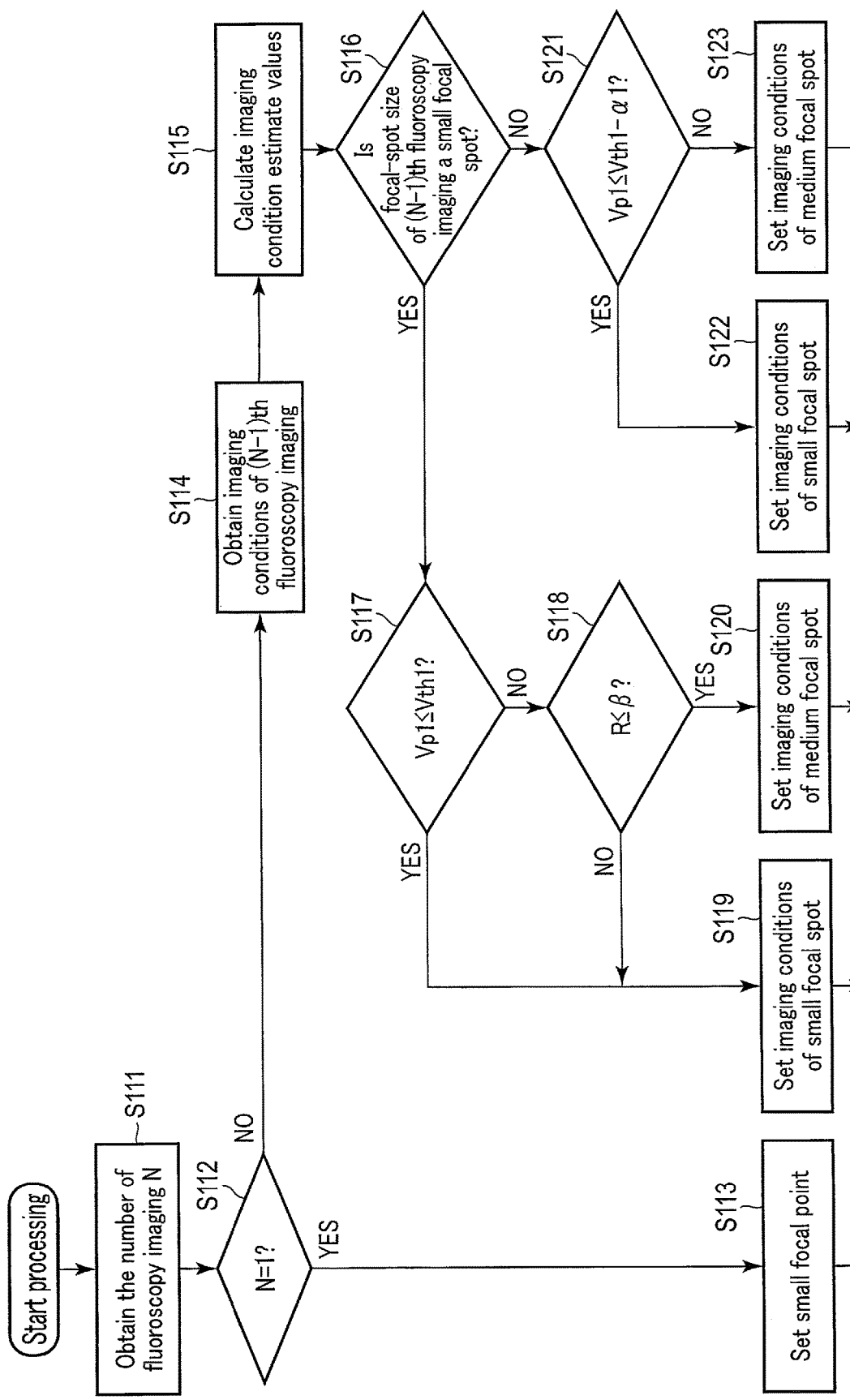
FIG. 3 is a flowchart illustrating a processing procedure of imaging condition setting processing performed by the X-ray diagnosis apparatus according to the first embodiment.

Next, the operation of the imaging condition setting processing performed by the X-ray diagnosis apparatus 1 will be described. The processing procedure in the imaging condition setting processing which will be described below is merely an example, and the processing can be changed as far as is reasonably possible. Omission, replacement, or addition of a step in the processing procedure described hereinafter can be made as appropriate, in accordance with an actual situation where the present embodiment is realized. FIG. 3 is a flowchart showing an example of the procedure of the imaging condition setting processing according to the present embodiment, and corresponds to the imaging condition setting processing in step S101 shown in FIG. 2.

(Step S111)

The processing circuitry 44 obtains a number indicating the number of times the fluoroscopy imaging has been performed since the examination commenced, in order to obtain the number of times the fluoroscopy imaging has been performed when the next imaging has been performed (hereinafter, "the number of times fluoroscopy imaging sessions performed"). The processing circuitry 44 obtains, for example, the number of times fluoroscopy imaging has been performed so far in order to determine the number of times the imaging has been performed when the next imaging has been performed. For example, if fluoroscopy imaging has not been performed since the examination commenced, the processing circuitry 44 determines that a next fluoroscopy imaging session is the first one following the commencement of the examination, and determines the number of times fluoroscopy imaging is performed to be 1. If fluoroscopy imaging has been performed once since the examination commenced, the processing circuitry 44 determines that a next fluoroscopy imaging session is the second one after the commencement of the examination, and determines the number of times fluoroscopy imaging is performed to be 2. Hereinafter, a case where the number of times fluoroscopy imaging is performed is N will be described as an example.

(Step S112)

The processing circuitry 44 determines whether or not the number N is 1. Through the determination, the processing circuitry 44 determines whether or not the fluoroscopy imaging to be performed next is fluoroscopy imaging performed for the first time since the commencement of the examination, or the imaging of the second time or thereafter since the commencement of the examination. If the number N is 1 (Yes in step S112), the fluoroscopy imaging to be performed next is the first one since the commencement of the examination, and the processing proceeds to step S113. If the number of fluoroscopy imaging sessions N is not 1 (No in step S112), in other words, if N is 2 or greater, the next fluoroscopy imaging is performed for the second time or thereafter since the commencement of the examination, and the processing proceeds to step S114.

(Step S113)

The processing circuitry 44 reads default imaging conditions for the fluoroscopy imaging performed for the first time since the commencement of the examination from the memory 41, and sets the default imaging conditions as imaging conditions for the fluoroscopy imaging to be performed next. At this time, the processing circuitry 44 sets a small focal-spot as a focal-spot size in the fluoroscopy imaging to be performed next.

(Step S114)

The processing circuitry 44 obtains the imaging conditions in the (N−1)th fluoroscopy imaging if the number of fluoroscopy imaging sessions is 2 or greater. The processing circuitry 44 reads and obtains the imaging conditions in the (N−1)th fluoroscopy imaging stored in the memory 41. The processing circuitry 44 obtains the imaging conditions for the (N−1)th fluoroscopy imaging so as to obtain imaging conditions in an immediately prior fluoroscopy imaging session among all the fluoroscopy imaging sessions performed since the commencement of the examination. The processing circuitry 44 obtains, for example, a focal-spot size, filter specifying information, a tube voltage, a tube current, a pulse width, and an AGC magnification, as imaging conditions in the (N−1)th fluoroscopy imaging. As described above, during the fluoroscopy imaging, feedback control is performed to change X-ray conditions, etc. based on the change in the subject conditions, and when the fluoroscopy imaging is finished, at least one of the tube voltage, the tube current, the pulse width, and the AGC magnification is appropriately controlled according to the change in the subject conditions. Accordingly, through obtaining the imaging conditions in the immediately prior fluoroscopy imaging session, it is possible to obtain the imaging conditions appropriately controlled in accordance with the change in the subject conditions. Through computation based on an X-ray image generated in an immediately prior fluoroscopy imaging session, the imaging conditions further appropriately controlled may be calculated in accordance with the change in the subject conditions, and the calculated imaging conditions may be obtained as imaging conditions in the fluoroscopy imaging session immediately prior.

(Step S115)

The processing circuitry 44 calculates imaging conditions when an X-ray detector entrance dose is approximated to an X-ray dose necessary to secure image quality of X-ray image (hereinafter, "target dose") to the greatest extent possible in the X-ray generator 12 (hereinafter, such conditions will be referred to as "imaging condition estimate values") for both a case where the fluoroscopy imaging is performed with a small focal spot and a case where the fluoroscopy imaging is performed with a medium focal spot in the N-th fluoroscopy imaging. The imaging condition estimate value is an imaging condition when a condition regarding a short time rating and a continuous rating of a tube are satisfied and an X-ray detector entrance dose is approximated to a target dose to the greatest extent possible. Specifically, for example, if the number of fluoroscopy imaging sessions N is 2, the processing circuitry 44 may calculate imaging condition estimate values in the second moving picture imaging based on the focal-spot size of X-rays, tube voltage, tube current, pulse width, AGC modification and filter specifying information obtained based on the output of the X-ray detector 13 in the first moving picture imaging. Herein, if the number of fluoroscopy imaging sessions N is 2, the first moving picture imaging and the second moving picture imaging correspond to the (N−1)th moving picture imaging and the Nth moving picture imaging, respectively. If the number of fluoroscopy imaging sessions N is 3, the processing circuitry 44 may calculate an imaging condition estimate value in the third moving picture imaging based on the focal-spot size of X-rays, tube voltage, tube current, pulse width, AGC modification and filter specifying information obtained based on the output of the X-ray detector 13 in the second moving picture imaging. Similarly, if the number of fluoroscopy imaging sessions N is 3, the second moving picture imaging and the third moving picture imaging correspond to the (N−1)th moving picture imaging and the Nth moving picture imaging, respectively.

The imaging condition estimate values include X-ray conditions when the X-ray detector entrance dose is approximated to the target dose to the greatest extent possible in the X-ray generator 12 (hereinafter, "X-ray condition estimate values"), and an AGC magnification which is predicted to be applied by the AGC when the X-ray detector entrance dose is approximated to the target dose to the greatest extent possible in the X-ray generator 12 (hereinafter, "AGC magnification estimate value"). The X-ray condition estimate values include: a tube voltage when an X-ray detector entrance dose is approximated to a target dose to the greatest extent possible in the X-ray generator 12 (hereinafter, "tube voltage estimate value"); a tube current when an X-ray detector entrance dose is approximated to a target dose to the greatest extent possible in the X-ray generator 12 (hereinafter, "tube current estimate value"); and a pulse width when an X-ray detector entrance dose is approximated to a target dose to the greatest extent possible in the X-ray generator 12 (hereinafter, "pulse width estimate value"). The X-ray condition estimate values may be values that include at least one of the following: a tube voltage estimate value that satisfies a condition regarding an X-ray tube output necessary for securing image quality of an X-ray image (hereinafter, "target output"); a tube current estimate value that satisfies the condition; a pulse width estimate value that satisfies the condition regarding the target output; or an AGC modification estimate value that satisfies the condition regarding the target output.

As the processing for calculating the imaging condition estimate values, for example, processing based on the following expression, wherein the X-ray condition of a current fluoroscopy imaging session is $\{xV, mA, msec, AGC\}$, and the function h of a prior or current condition is (Focus, BF, $BF_{immediately\ prior}$, $kV_{immediately\ prior}$, $msec_{immediately\ prior}$, $AGC_{immediately\ prior}$) is performed:

$$X\{XV, mA, msec, AGC\}=h(\text{Focus}, BF, BF_{immediately\ prior}, kV_{immediately\ prior}, msec_{immediately\ prior}, AGC_{immediately\ prior})$$

In the above expression, kV is a tube voltage, mA is a tube current, msec is a pulse width, AGC is an AGC magnification, Focus is a focal-spot size, BF is filter specifying information, the subscript "immediately prior" means a condition in an immediately prior fluoroscopy imaging session, and no subscript means a condition in a current fluoroscopy imaging session.

In the processing for calculating the imaging condition estimate values, the processing circuitry 44 first calculates a target output based a focal-spot size, filter specifying information, a tube voltage, a tube current, a pulse width, and an AGC magnification in the (N−1)th fluoroscopy imaging. Next, the processing circuitry 44 calculates the following based on the target output and the filter specifying information in the N-th fluoroscopy imaging: a tube voltage estimate value Vp1, a tube current estimate value Ip1, a pulse width estimate value Wp1, and an AGC magnification estimate value Mp1 in the case where the fluoroscopy imaging is performed with a small focal spot; and a tube voltage estimate value Vp2, a tube current estimate value Ip2, a pulse width estimate value Wp2, and an AGC magnification estimate value Mp2 in the case where the fluoroscopy imaging is performed with a medium focal spot. If the immediately-prior focal-spot size is the same as one of the small focal spot or the medium focal spot, imaging condition estimate values indicating approximately the same imaging conditions as those in the immediately prior fluoroscopy imaging are calculated. To be more precise, for example, if the number of fluoroscopy imaging sessions N is 2, the processing circuitry 44 calculates the imaging condition estimate values in the second moving picture imaging for each of the plurality of focal-spot sizes having different focal-spot sizes of X-rays, and determines the imaging condition estimate values corresponding to the focal-spot size determined as a focal-spot size of X-rays as imaging conditions in the second moving picture imaging. Similarly, for example, if the number of fluoroscopy imaging sessions N is 3, the processing circuitry 44 calculates the imaging condition estimate values in the third moving picture imaging for each of the plurality of focal-spot sizes having different focal-spot sizes of X-rays, and determines the imaging condition estimate values corresponding to the focal-spot size determined as a size of the focal-spot sizes of X-rays as imaging conditions in the third moving picture imaging.

(Step S116)

The processing circuitry 44 determines whether or not the focal-spot size of the (N−1)th fluoroscopy imaging is a small focal spot based on the imaging conditions in the (N−1)th fluoroscopy imaging obtained in step S114. If the focal-point size of the (N−1)th fluoroscopy imaging is a small focal spot (Yes in step S116), the processing proceeds to step S117. If the focal-spot size in the (N−1)th fluoroscopy imaging is not a small focal spot (No in step S116), the processing circuitry 44 determines that the focal-spot size is a medium focal spot, and the processing proceeds to step S121.

(Step S117)

The processing circuitry 44 determines whether or not the tube voltage estimate value Vp1 is equal to or smaller than a threshold Vth1. The threshold Vth1 is a value for determining whether or not the contrast of an X-ray image to be generated satisfies a predetermined condition. The threshold Vth1 is a value determined based on the range of, for example, 20 to 150 kV. The threshold Vth1 may be set at a predetermined value, and may be input by an operator for each examination. The threshold Vth1 is an example of a determination value. The threshold Vth1 is also an example of a first value. If the tube voltage estimate value Vp1 is equal to or smaller than the threshold Vth1 (Yes in step S117), the processing proceeds to step S118. If the tube voltage estimate value Vp1 is not equal to or smaller than the threshold Vth1 (No in step S117), in other words, if the tube voltage estimate value Vp1 is greater than the threshold Vth1, the processing proceeds to step S119.

(Step S118)

The processing circuitry 44 determines whether or not a dose limit attainment index R is equal to or smaller than a threshold β. Herein, the dose limit attainment index R (=G/L×100 [%]) is a ratio of an exposure dose estimate value G to a dose limit L. The dose limit L is an upper limit value regarding a dose of X-rays that enters a subject per unit time (an entrance dose rate). In other words, the dose limit L is an upper limit value of an exposure dose. The dose limit L is predetermined by a country in which the apparatus is used, for example. The dose limit L is 50 mGr/min or 87 mGr/min, for example. The exposure dose estimate value G is a dose of X-rays predicted to enter the subject when the Nth fluoroscopy imaging is performed on the imaging condition, which is the imaging condition estimate value for the case of fluoroscopy imaging performed with the medium focal spot. The threshold β is a value for determining whether or not the exposure dose estimate value G is sufficiently small with respect to the dose limit L. The threshold β is an example of a dose determination value. The threshold β is a value determined based on the range of, for example, 90 to 99%. The threshold β may be set at a predetermined value, or input by an operator for each fluoroscopy imaging session.

In the processing in step S118, the processing circuitry 44 first calculates the exposure dose estimate value G, based on a tube voltage estimate value Vp2, a tube current estimate value Ip2, a pulse width estimate value Wp2, an AGC magnification estimate value Mp2, and filter specifying information in the N-th fluoroscopy imaging. Then, the dose limit attainment index R is calculated based on the exposure dose estimate value G and the dose limit L. If the dose limit attainment index R is equal to or smaller than the threshold β (Yes in step S118), the processing circuitry 44 determines that the entrance dose rate is sufficiently small with respect to the dose limit L when the N-th fluoroscopy imaging is performed on the imaging condition as the imaging condition estimate value corresponding to the medium focal spot, and the processing proceeds to step S120. If the dose limit attainment index R is larger than the threshold β (No in step S118), the processing circuitry 44 determines that the entrance dose rate is not sufficiently small with respect to the dose limit L when the N-th fluoroscopy imaging is performed on the imaging condition as the imaging condition estimate value corresponding to the medium focal spot, and the processing proceeds to step S119.

(Step S119)

The processing circuitry 44 sets the focal-spot size in the N-th fluoroscopy imaging to a small focal spot. The processing circuitry 44 sets the imaging condition estimate value corresponding to the small focal spot as an imaging condition in the N-th fluoroscopy imaging. At this time, the processing circuitry 44 sets: the tube voltage estimate value Vp1 as a tube voltage in the N-th fluoroscopy imaging; the tube current estimate value Ip1 as a tube current in the N-th fluoroscopy imaging; the pulse width estimate value Wp1 as a pulse width in the N-th fluoroscopy imaging; and the AGC magnification estimate value Mp1 as an AGC magnification in the N-th fluoroscopy imaging. Then, the processing circuitry 44 finishes the imaging condition setting processing, and the processing proceeds to step S103.

(Step S120)

The processing circuitry 44 sets the focal-spot size in the N-th fluoroscopy imaging to a medium focal spot. The processing circuitry 44 sets the imaging condition estimate value corresponding to the medium focal spot as an imaging condition in the N-th fluoroscopy imaging. At this time, the processing circuitry 44 sets: the tube voltage estimate value Vp2 as a tube voltage in the N-th fluoroscopy imaging; the tube current estimate value Ip2 as a tube current in the N-th fluoroscopy imaging; the pulse width estimate value Wp2 as a pulse width in the N-th fluoroscopy imaging; and the AGC magnification estimate value Mp2 as an AGC magnification in the N-th fluoroscopy imaging. Then, the processing circuitry 44 finishes the imaging condition setting processing, and the processing proceeds to step S103.

(Step S121)

The processing circuitry 44 determines whether or not the tube voltage estimate value Vp1 is equal to or smaller than the threshold Vth2. The threshold Vth2 is smaller than the threshold Vth1 by the set value α1. In other words, Vth2=Vth1−α1. The set value α1 is a value representing room in a tube voltage to determine whether or not the medium focal spot should be changed to the small focal spot, and is a value determined within the range from 1 to 10 kV, for example. The set value α1 may be set at a predetermined value, and may be input by an operator for each examination. The threshold Vth2 is an example of a determination value. The threshold Vth2 is also an example of a second value. If the tube voltage estimate value Vp1 is equal to or smaller than the threshold Vth2 (Yes in step S121), the processing proceeds to step S122. If the tube voltage estimate value Vp1 is not equal to or smaller than the threshold Vth2 (No in step S121), in other words, if the tube voltage estimate value Vp1 is greater than the threshold Vth2, the processing proceeds to step S123.

(Step S122)

The processing in step S122 is similar to that in step S119. In other words, the processing circuitry 44 sets the focal-spot size in the N-th fluoroscopy imaging to a small focal spot. Then, the processing circuitry 44 finishes the imaging condition setting processing, and the processing proceeds to step S103.

(Step S123)

The processing in step S123 is similar to that in step S120. In other words, the processing circuitry 44 sets the focal-spot size in the N-th fluoroscopy imaging to a medium focal spot. Then, the processing circuitry 44 finishes the imaging condition setting processing, and the processing proceeds to step S103.

When the imaging condition setting processing is finished, the processing circuitry 44 performs the N-th fluoroscopy imaging based on the imaging conditions set in the imaging condition setting processing. Then, when the N-th fluoroscopy imaging is finished, in the case of performing the next fluoroscopy imaging, the processing circuitry 44 performs the imaging condition setting processing in step S101 once again. At this time, the processing circuitry 44 determines the imaging conditions including a focal-spot size in the (N+1)-th fluoroscopy imaging, based on the X-ray conditions in the N-th fluoroscopy imaging, similarly to the imaging condition setting processing in the N-th fluoroscopy imaging.

In the following description, advantageous effects of the X-ray diagnosis apparatus 1 according to the present embodiment will be described.

The X-ray diagnosis apparatus 1 in the present embodiment determines the size of a focal spot of X-rays in second moving picture imaging, which is performed in accordance with an operation input at an operating unit after the first moving picture imaging, based on an output of the X-ray detector 13 in the first moving picture imaging performed in accordance with an operation input to the operating unit. Furthermore, the X-ray diagnosis apparatus 1 in the present embodiment determines the size of a focal spot of X-rays in third moving picture imaging, which is performed in accordance with an operation input at the operating unit after the second moving picture imaging, based on an output of the X-ray detector 13 in the second moving picture imaging.

In summary, the X-ray diagnosis apparatus 1 in the present embodiment determines a focal-spot size in fluoroscopy imaging performed next in accordance with an operation input to the input interface 43, based on an output of the X-ray detector 13 in the fluoroscopy imaging performed immediately prior in accordance with an operation input to the input interface 43.

For example, the X-ray diagnosis apparatus 1 of the present embodiment determines a focal-spot size in the N-th fluoroscopy imaging, which is performed in accordance with an operation input to the input interface 43 after the (N−1)th fluoroscopy imaging, based on the X-ray conditions in the (N−1)th fluoroscopy imaging performed in accordance with an operation input to the input interface 43, and determines a focal-spot size in the (N+1)th fluoroscopy imaging, which is performed in accordance with an operation input to the input interface 43 after the N-th fluoroscopy imaging, based on the X-ray conditions in the N-th fluoroscopy imaging performed in accordance with an operation input to the input interface 43.

The X-ray diagnosis apparatus 1 of the present embodiment determines a focal-spot size of X-rays at the time when second moving picture imaging is started based on an output of the X-ray detector 13 at the time when first moving picture imaging is finished, and determines a focal-spot size of X-rays at the time when third moving picture imaging is started based on an output of the X-ray detector 13 at the time when second moving picture imaging is finished.

For example, the X-ray diagnosis apparatus 1 of the present embodiment determines a focal-spot size of X-rays at the time when the N-th fluoroscopy imaging is started based on the X-ray conditions at the time when the (N−1)-th fluoroscopy imaging is finished, and determines a focal-spot size of X-rays at the time when the (N+1)-th fluoroscopy imaging is started based on the X-ray conditions at the time when the N-th fluoroscopy imaging is finished.

The X-ray diagnosis apparatus 1 of the present embodiment calculates, based on an output of the X-ray detector 13 in first moving picture imaging, an imaging condition estimate value that satisfies a condition regarding a target output in the case where a particular focal-spot size of X-rays is used in second moving picture imaging, and determines a focal-spot size of X-rays in the second moving picture imaging based on the imaging condition estimate value in the second moving picture imaging. Furthermore, the X-ray diagnosis apparatus 1 of the present embodiment calculates, based on an output of the X-ray detector 13 in second moving picture imaging, an imaging condition estimate value for third moving picture imaging, and determines a focal-spot size of X-rays in the third moving picture imaging based on the imaging condition estimate value in the third moving picture imaging.

For example, the X-ray diagnosis apparatus 1 of the present embodiment calculates a tube voltage estimate value Vp1 in the N-th fluoroscopy imaging based on the X-ray conditions in the (N−1)th fluoroscopy imaging, determines a focal-spot size in the N-th fluoroscopy imaging based on the tube voltage estimate value Vp1, calculates a tube voltage estimate value Vp1 in the (N+1)th fluoroscopy imaging based on the X-ray conditions in the N-th fluoroscopy imaging, and determines a focal-spot size in the (N+1)th fluoroscopy imaging based on the tube voltage estimate value Vp1.

In other words, according to the X-ray diagnosis apparatus 1 of the present embodiment, with the above-described configurations and operations, it is possible to determine a focal-spot size in next fluoroscopy imaging, which is performed through stepping a foot switch once again, based on an output of the X-ray detector 13 in fluoroscopy imaging performed immediately prior. For this reason, in the next fluoroscopy imaging, it is possible to set a focal-spot size in accordance with X-ray conditions of fluoroscopy imaging performed immediately prior. Thus, even when a focal-spot size appropriate for generating an X-ray image in which its contrast satisfies a predetermined condition has been changed due to a change in a body thickness of the subject during immediately prior fluoroscopy imaging, it is still possible to automatically set an appropriate focal-spot size in next fluoroscopy imaging based on X-ray conditions controlled at appropriate values in accordance with the body thickness of the subject through the feedback control. It is thereby possible to improve image quality of an X-ray image generated in next fluoroscopy imaging. For example, if the body thickness of the subject is small and a tube bulb output is small, a focal-spot size can be set to a small focal spot, and a sharp image can be thereby generated. In contrast, when the body thickness of the subject is large and the tube voltage becomes high at the small focal spot, it is possible to generate an image having a high contrast or an image having less noise through switching the focal-spot size to a medium focal spot that provides a higher output.

The X-ray diagnosis apparatus 1 of the present embodiment determines a first focal-spot size as a focal-spot size of X-rays in second moving picture imaging when the imaging condition estimate value in the second moving picture imaging is equal to or smaller than the determination value, and determines a second focal-spot size, larger than the first focal-spot size, as a focal-spot size of X-rays in second moving picture imaging when the imaging condition estimate value in the second moving picture imaging is greater than the determination value. Furthermore, the X-ray diagnosis apparatus 1 of the present embodiment sets a first focal-spot size as a focal-spot size of X-rays in third moving picture imaging when the imaging condition estimate value in the third moving picture imaging is equal to or smaller than the determination value, and determines a second focal-spot size as a focal-spot size of X-rays in third moving picture imaging when the imaging condition estimate value in the third moving picture imaging is greater than the determination value.

In summary, for example, in the processing of step S121, the X-ray diagnosis apparatus 1 of the present embodiment determines, if the tube voltage estimate value Vp1 in the N-th fluoroscopy imaging is equal to or smaller than the threshold Vth2, a focal-spot size in the N-th fluoroscopy imaging to a small focal spot, and also determines, if the tube voltage estimate value Vp1 in the N-th fluoroscopy imaging is greater than the threshold Vth2, a focal-spot size in the N-th fluoroscopy imaging to a medium focal spot.

For example, if the body thickness of the subject becomes smaller during immediately prior fluoroscopy imaging using a medium focal spot, an X-ray tube output necessary for generating an X-ray image having brightness of a predetermined level or higher becomes smaller. In this case, according to the X-ray diagnosis apparatus 1 of the present embodiment, the tube voltage estimate value Vp1 in the small focal spot becomes equal to or smaller than the threshold Vth2, and the focal-spot size in the next fluoroscopy imaging is set to a small focal spot. Thus, if the X-ray tube output is small, in other words, if an X-ray image having a predetermined contrast or higher can be generated using a small focal spot, which provides only a small output, it is possible to generate an X-ray image having a higher resolution compared to a case where a focal-spot size is set to a medium focal spot, through setting a focal-spot size to a small focal spot in next fluoroscopy imaging.

Furthermore, for example, if the body thickness of the subject becomes larger during immediately prior fluoroscopy imaging using a small focal spot, an X-ray tube output necessary for generating an X-ray image having brightness of a predetermined level or higher becomes greater, thereby reducing a contrast of the X-ray image to be generated. In this case, according to the X-ray diagnosis apparatus 1 of the present embodiment, the tube voltage estimate value Vp1 in the small focal spot becomes greater than the threshold Vth2, and the focal-spot size in the next fluoroscopy imaging is set to a medium focal spot. For this reason, through switching the focal-spot size to a medium focal spot, which can increase the X-ray tube output compared to a small focal spot, it is possible to secure a necessary dose and control the tube voltage in next fluoroscopy imaging. Accordingly, compared to the case where a small focal-spot size is continuously used, it is possible to generate an X-ray image with more secured contrast and less noise.

The X-ray diagnosis apparatus 1 of the present embodiment changes the focal-spot size of X-rays based on the relationship in size between a parameter and a threshold based on the output of the X-ray detector, and a threshold relating to the change of the focal-spot size of X-rays from a first size to a second size, which is larger the first size, differs from a threshold relating to the change of the focal-spot size of X-rays from a second size to a first size. The dose of X-rays corresponding to a threshold when a focal-spot size of X-rays is changed from a first size to a second size is larger than the dose of X-rays corresponding to a threshold when a focal-spot size of X-rays is changed from a second size to a first size.

Specifically, the X-ray diagnosis apparatus 1 of the present embodiment changes a focal-spot size of X-rays based on a relationship in size between the tube voltage estimate value Vp1 and a threshold. The dose of X-rays corresponding to the threshold Vth1 when the focal-spot size is changed from a small focal spot to a medium focal spot is larger than the dose of X-rays corresponding to the threshold Vth2 when the focal-spot size of X-rays is changed from a medium focal spot to a small focal spot.

The X-ray diagnosis apparatus 1 of the present embodiment determines a focal-spot size of X-rays in second moving picture imaging using a first value as a determination value when a focal-spot size of X-rays in first moving picture imaging is a first focal-spot size, and determines a focal-spot size of X-rays in second moving picture imaging using a second value, which is different from the first value, as a determination value when a focal-spot size of X-rays in first moving picture imaging is a second focal-spot size. If the focal-spot size of X-rays in the second moving picture imaging is a first focal-spot size, a focal-spot size of X-rays in third moving picture imaging is determined using a first value as a determination value, and if the focal-spot size of X-rays in the second moving picture imaging is a second focal-spot size, a focal-spot size of X-rays in third moving picture imaging is determined using a second value as a determination value. For example, the second value is smaller than the first value.

In summary, the X-ray diagnosis apparatus 1 of the present embodiment determines, if the focal-spot size in the (N−1)-th fluoroscopy imaging is a small focal spot for example, a focal-spot size in the N-th fluoroscopy imaging based on the tube voltage estimate value Vp1 and the threshold Vth1 in the N-th fluoroscopy imaging, and determines, if the focal-spot size in the (N−1)-th fluoroscopy imaging is a medium focal spot for example, a focal-spot size in the N-th fluoroscopy imaging based on the tube voltage estimate value Vp1 and the threshold Vth2 in the N-th fluoroscopy imaging. Herein, the threshold Vth2 is smaller than the threshold Vth1.

In other words, according to the X-ray diagnosis apparatus 1 of the present embodiment, with the above-described configurations and operations, a threshold for determining whether or not the focal-spot size in next fluoroscopy imaging should be switched from a medium focal spot to a small focal spot differs from a threshold for switching the focal-spot size from a small focal spot to a medium focal spot. For this reason, it is possible to prevent the switching of a focal-spot size every time fluoroscopy imaging is performed, even when, for example, the tube voltage estimate value Vp1 is switched between a range smaller than the threshold Vth and a range larger than the threshold Vth every time fluoroscopy imaging is switched to a next one.

The X-ray diagnosis apparatus 1 of the present embodiment further calculates: a ratio of an exposure dose estimate value to an upper limit value of the exposure limit when imaging condition estimate values in second moving picture imaging are used as imaging conditions in the second moving picture imaging; and a ratio of an exposure dose estimate value to an upper limit value of the exposure limit when imaging condition estimate values in third moving picture imaging are used as imaging conditions in the third moving picture imaging. Furthermore, if the focal-spot size of X-rays in first moving picture imaging is a first focal-spot size and the imaging condition estimate values in the second moving picture imaging are larger than determination values, and the ratio in the second moving picture imaging is larger than a dose determination value, the first focal-spot size is determined as a focal-spot size of X-rays in the second moving picture imaging. If the focal-spot size of X-rays in the second moving picture imaging is the first focal-spot size and the imaging condition estimate values in the third moving picture imaging are larger than the determination values, and the ratio in the third moving picture imaging is larger than a dose determination value, the first focal-spot size is determined as a focal-spot size of X-rays in the third moving picture imaging.

In summary, the X-ray diagnosis apparatus 1 of the present embodiment determines a focal-spot size in N-th fluoroscopy imaging to a medium focal spot if, for example, the focal-spot size in the (N−1)th fluoroscopy imaging is a small focal spot and the tube voltage estimate value Vp1 in the N-th fluoroscopy imaging is greater than the threshold Vth1, and the exposure limit attainment index R is equal to or smaller than the threshold β, and determines a focal-spot size in the (N−1)th fluoroscopy imaging to a small focal spot if the focal-spot size in the (N−1)th fluoroscopy imaging is a small focal spot and the tube voltage estimate value Vp1 in the N-th fluoroscopy imaging is greater than the threshold Vth1, and the exposure limit attainment index R is greater than the threshold β.

Accordingly, if a small focal spot is used in immediately prior fluoroscopy imaging, the X-ray diagnosis apparatus 1 of the present embodiment switches the next focal-spot size to a medium focal-spot size only when a contrast of an X-ray image generated in next fluoroscopy imaging becomes lower, and a predicted exposure dose is sufficiently small with respect to a dose limit in the case where the medium focal spot is used as the focal-spot size is secured. In contrast, even when a contrast of an X-ray image to be generated in next fluoroscopy imaging becomes lower in the X-ray diagnosis apparatus 1 of the present embodiment, the next focal-spot size is not switched to a medium focal spot unless the predicted exposure dose is sufficiently small with respect to the dose limit is secured.

In other words, according to the X-ray diagnosis apparatus 1 of the present embodiment, with the foregoing configurations and operations, the focal-spot size is switched to a medium focal spot for which an exposure dose to the subject becomes greater, only when room in an exposure dose can be secured at a certain extent. It is thereby possible to prevent an excess of the exposure dose to the subject over the dose limit in the next fluoroscopy imaging.

Second Embodiment

Next, the second embodiment will be described. The present embodiment is a modification of the configuration of the first embodiment as will be described below. In the present embodiment, the imaging condition setting processing performed by the processing circuitry 44 through the imaging condition setting function 442 is partially different from that in the first embodiment. In the present embodiment, the processing circuitry 44 determines a focal-spot size in next fluoroscopy imaging using a tube current estimate value, instead of a tube voltage estimate value. Descriptions of the configurations, operations, and advantageous effects similar to those of the first embodiment will be omitted.

Figure 4:
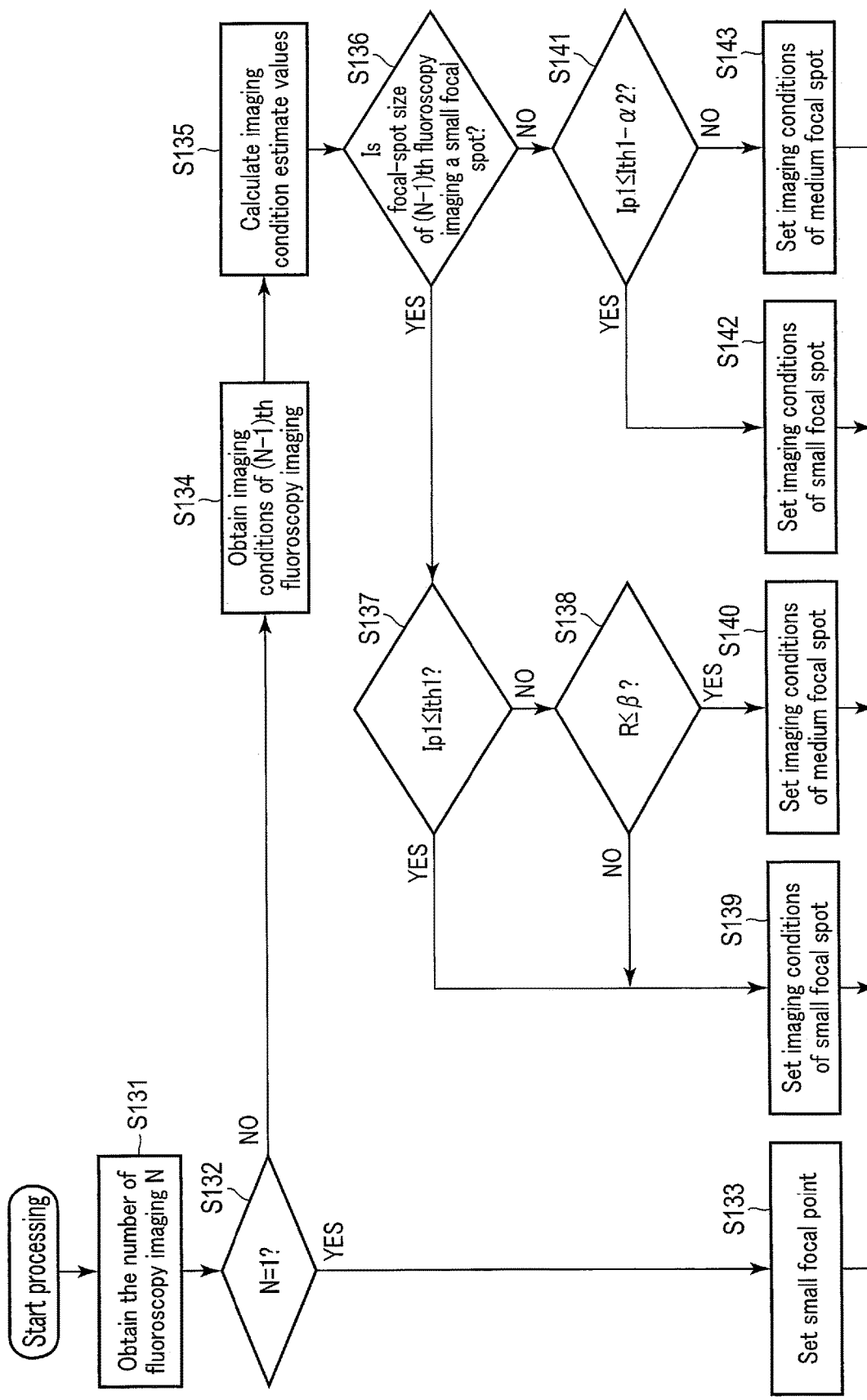
FIG. 4 is a flowchart illustrating a processing procedure of imaging condition setting processing performed by an X-ray diagnosis apparatus according to a second embodiment.

In the following, the operation of the imaging condition setting processing which is performed by the X-ray diagnosis apparatus 1 will be described. FIG. 4 is a flowchart illustrating a processing procedure of the imaging condition setting processing performed by the X-ray diagnosis apparatus 1 according to the present embodiment. Since the processing in step S131 through step S136, step S138 through step S140, step S142 through step S143 in FIG. 4 are the same as the processing in step S111 through step S116, step S119 through step S120, and step S122 through step S123 in the first embodiment, the descriptions of the processing are omitted.

(Imaging Condition Setting Processing)
(Step S137)

The processing circuitry 44 determines whether or not a tube current estimate value Ip1 is equal to or smaller than the threshold Ith1. The threshold Ith1 is a value for determining whether or not a contrast of an X-ray image to be generated satisfies a predetermined condition. The threshold Ith1 is a value determined based on the range of, for example, 50 to 200 mA. The threshold Ith1 may be set at a predetermined value, and may be input by an operator for each examination. The threshold Ith1 is an example of a determination value. The threshold Ith1 is also an example of a first value. If the tube current estimate value Ip1 is equal to or smaller than the threshold Ith1 (Yes in step S137), the processing proceeds to step S138. If the tube current estimate value Ip1 is not equal to or smaller than the threshold Ith1 (No in step S137), in other words, if the tube current estimate value Ip1 is greater than the threshold Ith1, the processing proceeds to step S139.

(Step S141)

The processing circuitry 44 determines whether or not the tube current estimate value Ip1 is equal to or smaller than the threshold Ith2. The threshold Ith2 is smaller than the threshold Ith1 by the set value $\alpha 2$. In other words, Ith2=Ith1−$\alpha$. The set value $\alpha 2$ is a value determined based on the range of, for example, 5 to 20 mA. The set value $\alpha 2$ may be set at a predetermined value, and may be input by an operator for each examination. The threshold Ith2 is an example of a determination value. The threshold Ith2 is also an example of a second value. If the tube current estimate value Ip1 is equal to or smaller than the threshold Ith2 (Yes in step S141), the processing proceeds to step S122. If the tube current estimate value Ip1 is not equal to or smaller than the threshold Ith2 (No in step S141), in other words, if the tube voltage estimate value Ip1 is greater than the threshold Ith2, the processing proceeds to step S123.

In the following description, advantageous effects of the X-ray diagnosis apparatus 1 according to the present embodiment will be described.

The X-ray diagnosis apparatus 1 of the present embodiment calculates, for example, a tube current estimate value Ip1 in the N-th fluoroscopy imaging based on the X-ray conditions in the (N−1)th fluoroscopy imaging, determines a focal-spot size in the N-th fluoroscopy imaging based on the tube current estimate value Ip1, calculates a tube voltage estimate value Vp1 in the (N+1)th fluoroscopy imaging based on an output of the X-ray conditions in the N-th fluoroscopy imaging, and determines a focal-spot size in the (N+1)th fluoroscopy imaging based on the tube voltage estimate value Vp1.

Accordingly, the X-ray diagnosis apparatus 1 in the present embodiment determines a focal-spot size in fluoroscopy imaging performed next in accordance with an operation input to the input interface 43, based on an output of the X-ray detector 13 in fluoroscopy imaging performed immediately prior to an operation input to the input interface 43. For this reason, even in the X-ray diagnosis apparatus 1 of the present embodiment, advantageous effects similar to those of the first embodiment can be achieved.

Third Embodiment

Next, the third embodiment will be described. The present embodiment is a modification of the configuration of the first embodiment as will be described below. In the present embodiment, the imaging condition setting processing performed by the processing circuitry 44 through the imaging condition setting function 442 is partially different from that in the first embodiment. In the present embodiment, the processing circuitry 44 determines a focal-spot size in next fluoroscopy imaging using a pulse width estimate value, instead of a tube voltage estimate value. Descriptions of the configurations, operations, and advantageous effects similar to those of the first embodiment will be omitted.

Figure 5:
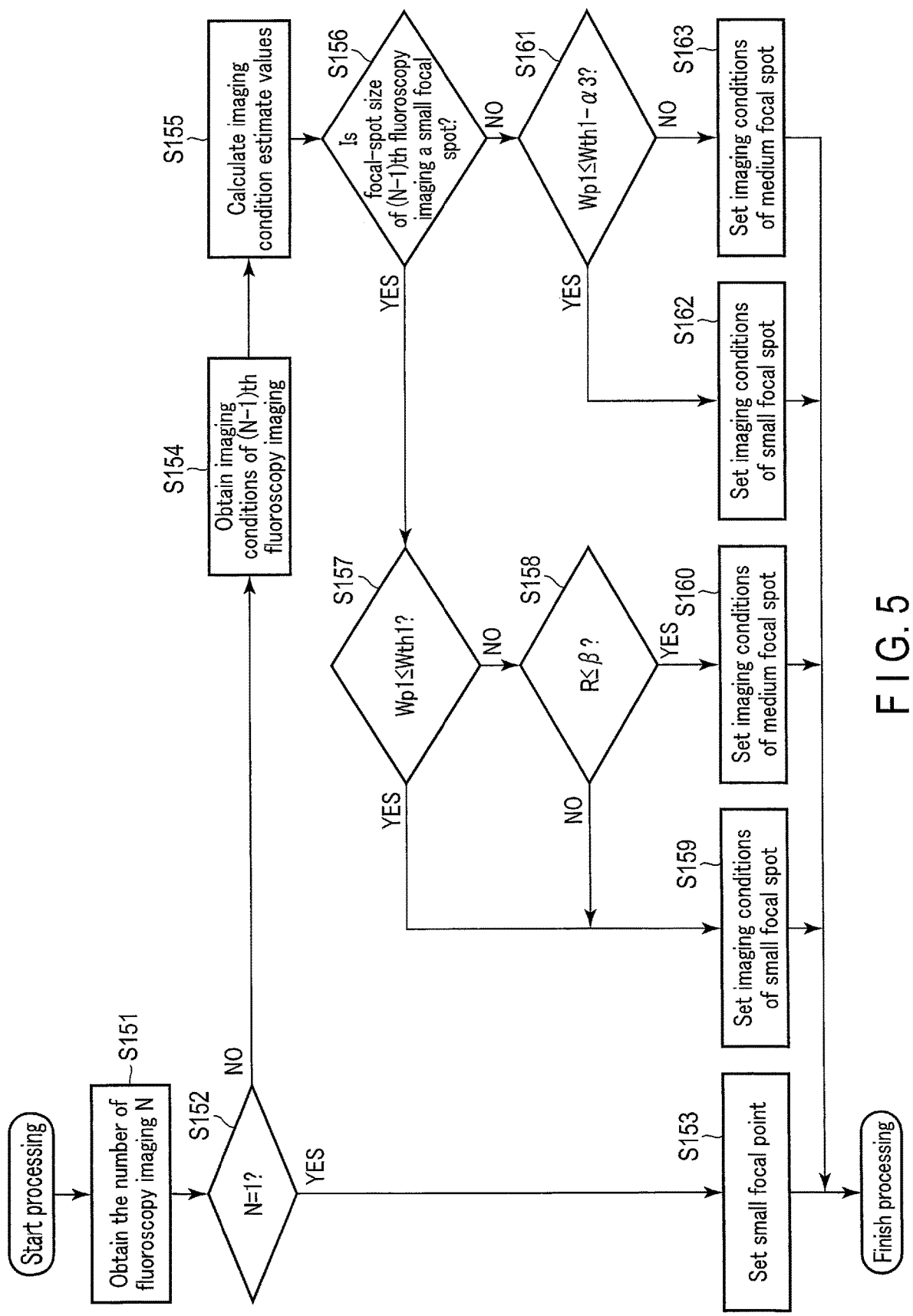
FIG. 5 is a flowchart illustrating a processing procedure of imaging condition setting processing by an X-ray diagnosis apparatus according to a third embodiment.

In the following, the operation of the imaging condition setting processing which is performed by the X-ray diagnosis apparatus 1 will be described. FIG. 5 is a flowchart illustrating a processing procedure of the imaging condition setting processing performed by the X-ray diagnosis apparatus 1 according to the present embodiment. Since the processing in step S151 through step S156, step S158 through step S160, step S162 through step S163 in FIG. 5 are the same as the processing in step S111 through step S116, step S119 through step S120, and step S122 through step S123 in the first embodiment, the descriptions of the processing are omitted.

(Imaging Condition Setting Processing)
(Step S157)

The processing circuitry 44 determines Wp1 is equal to or smaller than the threshold Wth1. The threshold Wth1 is a value for determining whether or not a contrast of an X-ray image to be generated satisfies a predetermined condition. The threshold Wth1 is a value determined based on the range of, for example, 10 to 20 ms. The threshold Wth1 may be set at a predetermined value, and may be input by an operator for each examination. The threshold Wth1 is an example of a determination value. The threshold Wth1 is also an example of a first value. If the pulse width estimate value Wp1 is equal to or smaller than the threshold Wth1 (Yes in step S157), the processing proceeds to step S158. If the pulse width estimate value Wp1 is not equal to or smaller than the threshold Wth1 (No in step S157), in other words, if the tube voltage estimate value Wp1 is greater than the threshold Wth1, the processing proceeds to step S160.

(Step S161)

The processing circuitry 44 determines whether or not the pulse width estimate value Wp1 is equal to or smaller than the threshold Wth2. The threshold Wth2 is smaller than the threshold Wth1 by the set value α3. In other words, Wth2=Wth1−α3. The set value α3 is a value determined based on the range of, for example, 3 to 5 ms. The set value α3 may be set at a predetermined value, and may be input by an operator for each examination. The threshold Wth2 is an example of a determination value. The threshold Wth2 is also an example of a second value. If the pulse width estimate value Wp1 is equal to or smaller than the threshold Wth2 (Yes in step S161), the processing proceeds to step S162. If the pulse width estimate value Wp1 is not equal to or smaller than the threshold Wth2 (No in step S161), in other words, if the pulse width estimate value Wp1 is greater than the threshold Wth2, the processing proceeds to step S163.

In the following description, advantageous effects of the X-ray diagnosis apparatus 1 according to the present embodiment will be described.

The X-ray diagnosis apparatus 1 of the present embodiment calculates a pulse width estimate value Wp1 in the N-th fluoroscopy imaging based on the X-ray conditions in the (N−1)th fluoroscopy imaging, determines a focal-spot size of X-rays in the N-th fluoroscopy imaging based on a tube current estimate value Ip1, calculates a pulse width estimate value Wp1 in the (N+1)th fluoroscopy imaging based on the X-ray conditions in the N-th fluoroscopy imaging, and determines a focal-spot size of X-rays in the (N+1)th fluoroscopy imaging based on a tube voltage estimate value Vp1.

Accordingly, the X-ray diagnosis apparatus 1 in the present embodiment determines a focal-spot size in fluoroscopy imaging performed next in accordance with an operation input to the input interface 43, based on an output of the X-ray detector 13 in fluoroscopy imaging performed immediately prior to an operation input to the input interface 43. For this reason, advantageous effects similar to those of the first embodiment can be achieved by the X-ray diagnosis apparatus 1 of the present embodiment.

Fourth Embodiment

Figure 6:
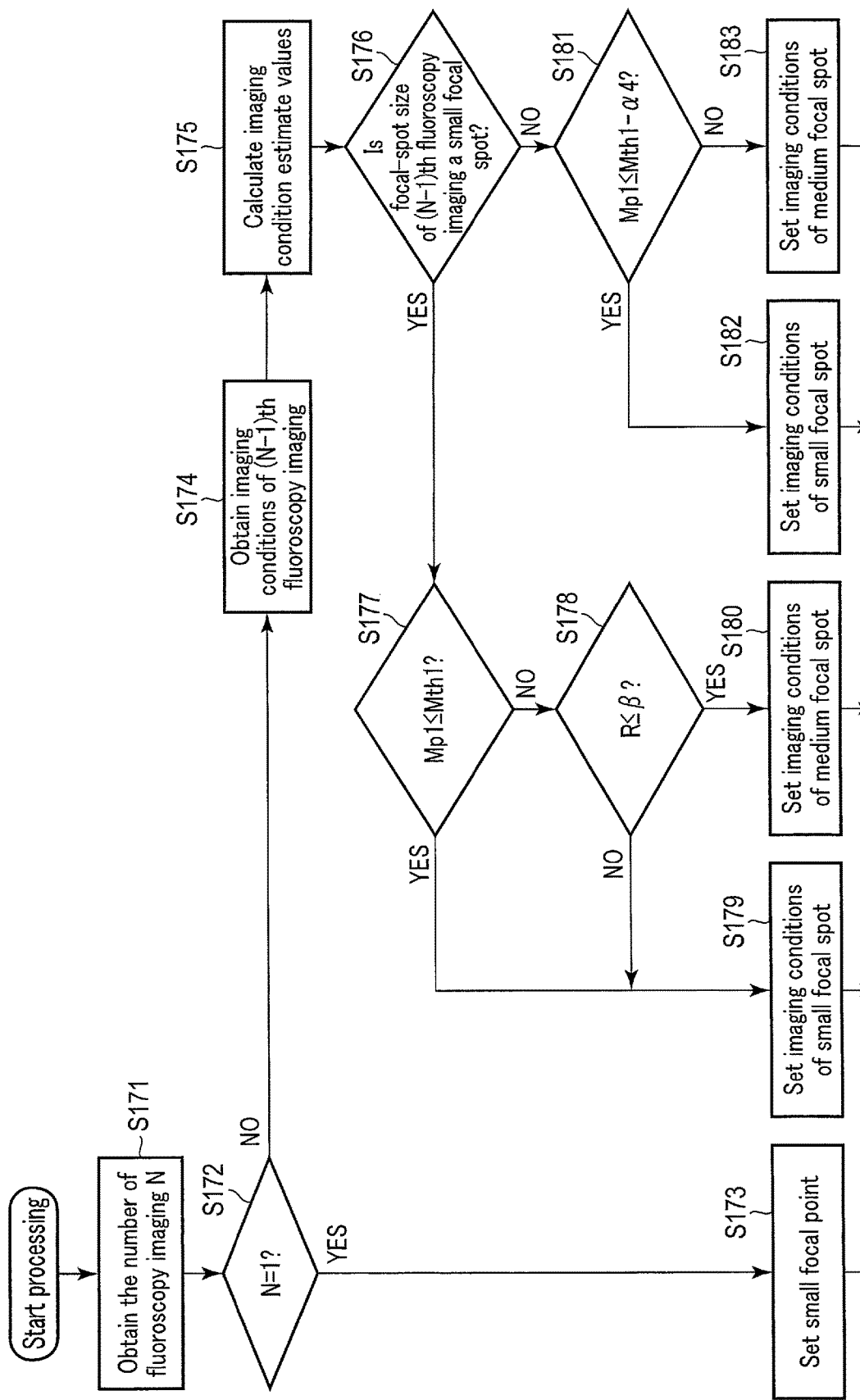
FIG. 6 is a flowchart illustrating a processing procedure of imaging condition setting processing by an X-ray diagnosis apparatus according to a fourth embodiment.

Next, the fourth embodiment will be described. The present embodiment is a modification of the configuration of the first embodiment as will be described below. In the present embodiment, the imaging condition setting processing performed by the processing circuitry 44 through the imaging condition setting function 442 is partially different from that in the first embodiment. In the present embodiment, the processing circuitry 44 determines a focal-spot size in next fluoroscopy imaging using an AGC magnification estimate value, instead of a tube voltage estimate value. Descriptions of the configurations, operations, and advantageous effects similar to those of the first embodiment will be omitted. In the following, the operation of the imaging condition setting processing which is performed by the X-ray diagnosis apparatus 1 will be described. FIG. 6 is a flowchart illustrating a processing procedure of the imaging condition setting processing performed by the X-ray diagnosis apparatus 1 according to the present embodiment. Since the processing in step S171 through step S176, step S178 through step S180, step S182 through step S183 in FIG. 6 are the same as the processing in step S111 through step S116, step S119 through step S120, and step S122 through step S123 in the first embodiment, the descriptions of the processing are omitted.

(Imaging Condition Setting Processing)
(Step S177)

The processing circuitry 44 determines whether or not the AGC magnification estimate value Mp1 is equal to or smaller than the threshold Mth1. The threshold Mth1 is a value for determining whether or not noise of an X-ray image to be generated satisfies a predetermined condition. The threshold Mth1 is a value determined based on the range of, for example, 110 to 200%. The threshold Mth1 may be set at a predetermined value, and may be input by an operator for each examination. The threshold Mth1 is an example of a determination value. The threshold Mth1 is also an example of a first value. If the AGC magnification estimate value Mp1 is equal to or smaller than the threshold Mth1 (Yes in step S177), the processing proceeds to step S178. If the AGC magnification estimate value Mp1 is not equal to or smaller than the threshold Mth1 (No in step S177), in other words, if the AGC magnification estimate value Mp1 is greater than the threshold Mth1, the processing proceeds to step S179.

(Step S181)

The processing circuitry 44 determines whether or not the AGC magnification estimate value Mp1 is equal to or smaller than the threshold Mth2. The threshold Mth2 is smaller than the threshold Mth1 by the set value α4. In other words, Mth2=Mth1−α4. The set value α4 is a value determined based on the range of, for example, 5 to 20%. The set value α4 may be set at a predetermined value, and may be input by an operator for each examination. The threshold Mth2 is an example of a determination value. The threshold Mth2 is also an example of a second value. If the AGC magnification estimate value Mp1 is equal to or smaller than the threshold Mth2 (Yes in step S181), the processing proceeds to step S182. If the AGC magnification estimate value Mp1 is not equal to or smaller than the threshold Mth2 (No in step S181), in other words, if the AGC magnification estimate value Mp1 is greater than the threshold Mth2, the processing proceeds to step S183.

In the following description, advantageous effects of the X-ray diagnosis apparatus 1 according to the present embodiment will be described.

The X-ray diagnosis apparatus 1 of the present embodiment calculates an AGC magnification estimate value Mp1 in the N-th fluoroscopy imaging based on the X-ray conditions in the (N−1)th fluoroscopy imaging, determines a focal-spot size of X-rays in the N-th fluoroscopy imaging based on the AGC magnification estimate value Mp1, calculates an AGO magnification estimate value Mp1 in the (N+1)th fluoroscopy imaging based on the X-ray conditions in the N-th fluoroscopy imaging, and determines a focal-spot size of X-rays in the (N+1)th fluoroscopy imaging based on the AGC magnification estimate value Mp1.

In other words, according to the X-ray diagnosis apparatus 1 of the present embodiment, with the above-described configurations and operations, it is possible to determine a focal-spot size in next fluoroscopy imaging performed through stepping a foot switch once again, based on an output of the X-ray detector 13 in immediately prior fluoroscopy imaging. For this reason, in the next fluoroscopy imaging, it is possible to set a focal-spot size in accordance with X-ray conditions of immediately prior fluoroscopy imaging. Thus, even when a focal-spot size appropriate for generating an X-ray image in which its noise satisfies a predetermined condition has been changed due to a change in a body thickness of the subject during immediately prior fluoroscopy imaging, it is still possible to automatically set an appropriate focal-spot size in next fluoroscopy imaging based on X-ray conditions controlled at appropriate values in accordance with the subject's body thickness through the feedback control. Image quality of an X-ray image generated in next fluoroscopy imaging is thus improved.

Furthermore, in the processing of step S181 for example, the X-ray diagnosis apparatus 1 of the present embodiment determines, if the AGC magnification estimate value Mp1 in the N-th fluoroscopy imaging is equal to or smaller than the threshold Mth2, a focal-spot size in the N-th fluoroscopy imaging to a small focal spot, and determines, if the AGC magnification estimate value Mp1 in the N-th fluoroscopy imaging is greater than the threshold Mth2, a focal-spot size in the N-th fluoroscopy imaging to a medium focal spot.

For example, if an X-ray image having a predetermined brightness or higher even when the X-ray tube output is used at maximum, when the thickness of the subject's body becomes smaller during immediately prior fluoroscopy imaging using a medium focal spot, the AGC magnification necessary for generating an X-ray image having a brightness of a predetermined level or higher becomes smaller. In this case, according to the X-ray diagnosis apparatus 1 of the present embodiment, the AGC magnification estimate value Mp1 in the small focal spot becomes equal to or smaller than the threshold Mth2, and the focal-spot size in the next fluoroscopy imaging is set to a small focal spot. Thus, if there is sufficient room in the X-ray tube output, in other words, if an X-ray image having a predetermined brightness or higher and a small amount of noise can be generated using a small focal spot, which provides only a small output, it is possible to generate an X-ray image having a higher resolution compared to a case where a focal-spot size is set to a medium focal spot, through setting a focal-spot size to a small focal spot in next fluoroscopy imaging.

Furthermore, for example, if the thickness of the subject's body becomes smaller during immediately prior fluoroscopy imaging using a medium focal spot, the AGC magnification necessary for generating an X-ray image having a brightness of a predetermined level or higher becomes greater, thereby increasing noise in the X-ray image to be generated. In this case, according to the X-ray diagnosis apparatus 1 of the present embodiment, the AGC magnification estimate value Mp1 in the small focal spot becomes greater than the threshold Mth2, and the focal-spot size in the next fluoroscopy imaging is set to a medium focal spot. For this reason, through switching the focal-spot size to a medium focal spot, which can increase the X-ray tube output compared to a small focal spot, it is possible to secure a necessary dose and suppress the AGC magnification in next fluoroscopy imaging. Accordingly, compared to the case where a small focal-spot size is continuously used, it is possible to generate an X-ray image with more secured brightness and less noise.

Modifications of First to Fourth Embodiments

The imaging condition setting processing performed in step S101 is performed during the moving picture imaging in the fluoroscopy imaging, and a focal-spot size in next fluoroscopy imaging is determined based on current imaging conditions in the fluoroscopy imaging under processing. Thereafter, between the conclusion of the fluoroscopy imaging under processing and the commencement of the next fluoroscopy imaging, the focal-spot size is switched based on the focal-spot size determined in the imaging condition setting processing. In this case, the fluoroscopy imaging under processing corresponds to first moving picture imaging or second moving picture imaging, and the fluoroscopy imaging to be performed next after the fluoroscopy imaging under processing corresponds to second moving picture imaging or third moving picture imaging.

In the processing in step S117, step S137, step S157, or step S177, an imaging condition estimate value of a medium focal spot may be used instead of an imaging condition estimate value of a small focal spot; alternatively, an imaging condition estimate value in the case where a focal-spot size other than the small focal spot or medium focal spot is used may be used. Similarly, in the processing in step S121, step S141, step S161, or step S181, an imaging condition estimate value of a medium focal spot may be used instead of an imaging condition estimate value of a small focal spot; alternatively, an imaging condition estimate value in the case where a focal-spot size other than the small focal spot or medium focal spot is used may be used.

For example, if fluoroscopy imaging is performed in a first imaging mode in which a small focal spot is used and a high resolution level is provided, an upper limit of the X-ray tube output becomes smaller compared to the case where fluoroscopy imaging is performed in a second imaging mode in which a large focal spot is used and a low resolution level is provided; as a result, the X-ray tube output tends to reach a maximum output. For this reason, even when the body thickness of the subject changes during fluoroscopy imaging performed immediately prior, the tube voltage estimate value does not change easily. For this reason, a type of imaging condition estimate value used for determination may be selected in accordance with a resolution level of an X-ray image to be generated in next fluoroscopy imaging. For example, when an X-ray image having a first resolution level is generated, a focal-spot size in next fluoroscopy imaging is selected using an AGC magnification estimate value in a manner similar to the fourth embodiment; on the other hand, when an X-ray image having a resolution level higher than the first resolution level is generated, a focal-spot size in next fluoroscopy imaging is selected using a tube voltage estimate value in a manner similar to the first embodiment. The resolution level of the X-ray image generated in next fluoroscopy imaging may be obtained through an input of an imaging mode by an operator, or automatically obtained from the memory 41, etc., for example.

The focal-spot size may be switched by control of a control grid electrode capable of continuously adjusting a focal-spot size. In this case, the X-ray generator 12 is a grid control discharge tube having a cathode, an anode, and a control grid electrode, and one filament provided in a tube bulb will do. The processing circuitry 44 determines, through the imaging condition setting function 442, a next focal-spot size in next fluoroscopy imaging. Thereafter, the processing circuitry 44 controls, by the X-ray controlling function 444, the control grid electrode based on the determined focal-spot size of X-rays. Specifically, the processing circuitry 44 controls the control grid electrode so that the focal-spot size becomes the determined value.

The "output of the X-ray detector" used for determining the focal-spot size of X-rays by the imaging condition setting function 442 may be something other than X-ray image, as long as it is information to which an X-ray dose detected by the X-ray detector is reflected; for example, it can be a nondestructive reading result of a part or all of the pixels altogether in the X-ray detector (in other words, a signal corresponding to a sum of cumulative charge of a part or all of the pixels).

Although fluoroscopy is described as an example of moving picture imaging above, embodiments are not limited thereto. Other examples of moving picture imaging include radiography for a moving picture such as DA (Digital Angiography) and DSA (Digital Subtraction Angiography). Radiography is an imaging technique using stronger X-ray than fluoroscopy, and acquired images in radiography are stored in a storage. Radiography may be assigned to a switch different from the switch for fluoroscopy at the input interface 43.

When radiography is performed after fluoroscopy, the focal-spot size in radiography may be determined based on imaging condition estimate value in fluoroscopy. For example, when radiography is performed after two fluoroscopy operations, the focal-spot size in the second fluoroscopy operation may be determined based on the imaging condition estimate value in the first fluoroscopy operation, and the focal-spot size in the radiography may be determined based on the imaging condition estimate value in the second fluoroscopy.

According to at least one of the foregoing embodiments, it is possible to automatically set an appropriate focal-spot size.

Summary of Fifth to Eleventh Embodiments

Next, a summary of fifth to eleventh embodiments will be described. Conventionally, an X-ray diagnosis apparatus is provided in an X-ray generating unit, and has an X-ray diaphragm for adjusting a size of an X-ray irradiation size (hereinafter, a field-of-view size). The X-ray diaphragm has a plurality of filters having different thicknesses (hereinafter, "additional filters"). The added filter may be called "a radiation quality filter" or "a beam spectrum filter". At least one of the additional filters is inserted into a path from the focal spot of the X-ray tube to the X-ray detector, and arranged on the front surface of the X-ray radiation window in the X-ray generating unit. The added filter inserted in the path adjusts a radiation quality of X-rays by reducing soft X-rays passing through the added filter. The added filter inserted in the path is automatically selected based on a thickness of the subject's body (hereinafter, "body thickness") estimated from conditions of X-ray irradiation by an X-ray tube (hereinafter, "X-ray conditions"), and a source image distance (SID).

On the other hand, when a size of each of the detection elements of FPD (flat panel detector) provided in the X-ray detector (hereinafter, "FPD element size"), or a field-of-view size changes, a dose of X-rays necessary for securing an image quality of an X-ray image (hereinafter "target dose") also changes. If an added filter is selected without a consideration of the change in the target dose, there is a possibility that an appropriate added filter may not be selected.

For this reason, it is desired to select an appropriate added filter in accordance with a target dose.

In order to achieve the above objective, an X-ray diagnosis apparatus according to an embodiment includes the following: an X-ray tube that generates X-rays, an X-ray detector that detects X-rays generated from the X-ray tube; a plurality of filters that attenuate X-rays generated from the X-ray tube; a filter driving unit that inserts at least one of the plurality of filters into an X-ray path from a focal spot of X-rays in the X-ray tube to the X-ray detector; and a filter selecting unit that selects a filter to be inserted into the path from the plurality of filters based on at least one of a pixel size in the X-ray detector, a pixel size in an X-ray image based on the output of the X-ray detector, or a size of the X-ray irradiation area, and information regarding the body thickness of the subject.

Fifth Embodiment

Figure 7:
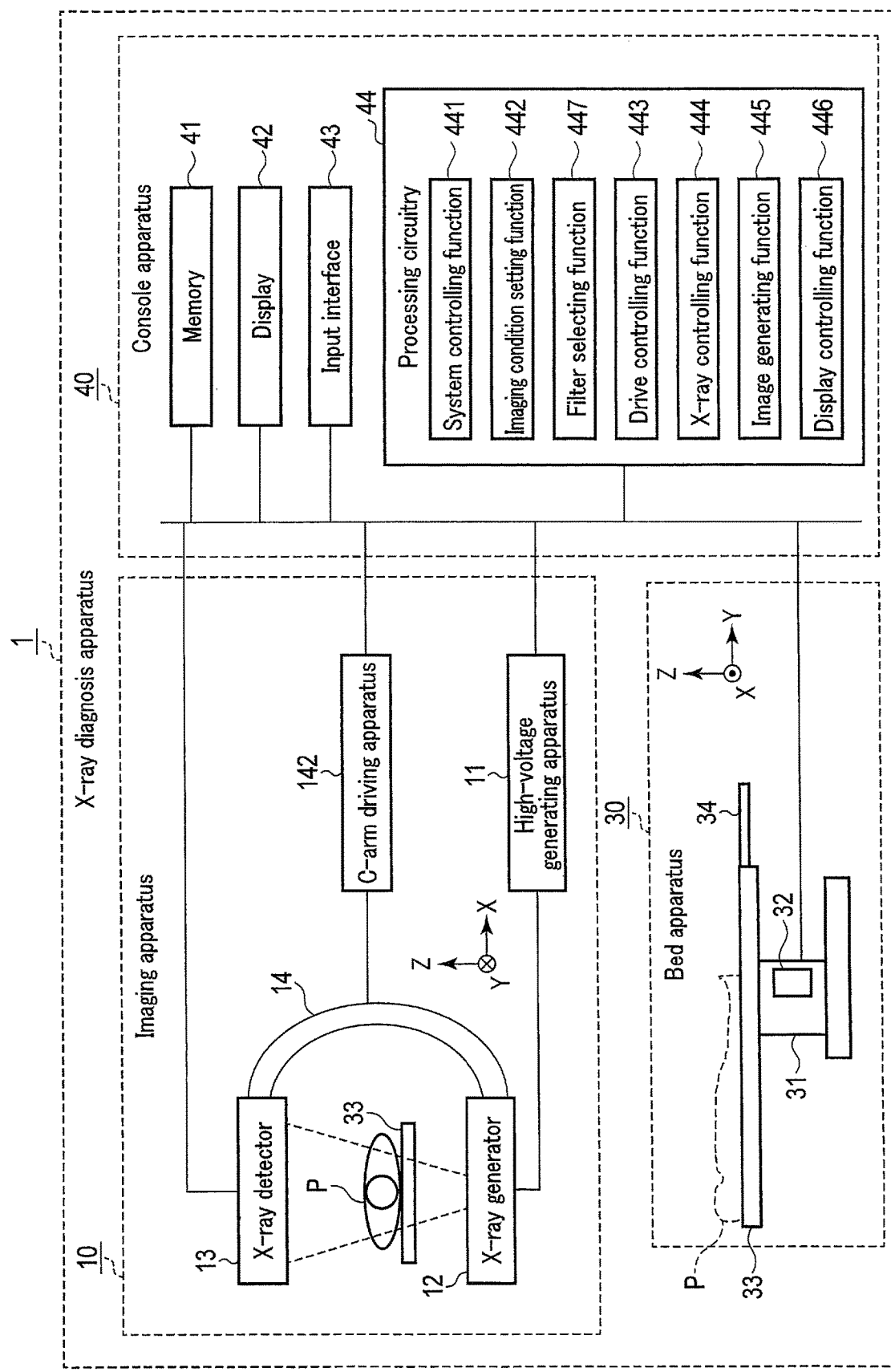
FIG. 7 is a block diagram showing the configuration of an X-ray image diagnosis apparatus according to a fifth embodiment.

Next, the fifth embodiment will be described. The present embodiment is a modification of the configuration of the first embodiment as will be described below. Descriptions of the configurations, operations, and advantageous effects similar to those of the first embodiment will be omitted. FIG. 7 is a drawing showing the configuration example of the X-ray image diagnosis apparatus 1 according to the fifth embodiment.

In the present embodiment, two types of FPD (FPD1 and FPD2) are provided in the X-ray detector 13. The FPD1 and FPD2 differ from each other in the following points: the number of detector elements (hereinafter, "FPD element number"); a size of the FPD element; a resolution level; a dose of X-rays necessary for securing an image quality of X-ray image (hereinafter "target dose"); and a corresponding imaging mode, etc. In the present embodiment, the FPD element size corresponds to a pixel size of the FPD (hereinafter, "FPD pixel size"). The FPD pixel size is an example of a pixel size in the X-ray detector 13. In accordance with an input by an operator via an input interface 43 (which will be described later), or setting of an imaging mode in a processing circuitry 44 (which will also be described later), an FPD to be used is selected from the two FPDs, and the FPD being used is switched to another by the driving of a driving apparatus (not shown). The FPD element number, the FPD element size, the FPD pixel size, the resolution level, and the target dose can be switched through the switching of the FPD being used. The size of the FPD1 and the size of the FPD2 may be different or the same. The FPD1 and the FPD2 may share one scintillator.

The FPD1 corresponds to a normal mode of an imaging mode. The FPD1 corresponds to a high-definition mode of an imaging mode that provides a higher resolution level than the normal mode does. The FPD2 has a larger FPD element number, a smaller FPD pixel size, and a smaller FPD element size, compared to the FPD1. For this reason, the target dose of the FPD2 is larger than that of the FPD1. The normal mode is an example of a first imaging mode. The high-definition mode is an example of a second imaging mode. The FPD pixel size of the FPD1 is an example of a first size of the FPD pixel size. The FPD pixel size of the FPD1 is an example of a first size of the FPD pixel size. The FPD element size of the FPD1 is an example of a first size of the FPD element size. The FPD element size of the FPD2 is an example of a second size of the FPD element size.

The processing circuitry 44 controls entire operation of the X-ray diagnosis apparatus 1. The processing circuitry 44 is a processor that invokes a program in the memory 41 and performs a system controlling function 441, an imaging condition setting function 442, a filter selecting function 447, a drive controlling function 443, an X-ray controlling function 444, an image generating function 445, and a display controlling function 446.

The processing circuitry 44 sets conditions for imaging (hereinafter, "imaging conditions") through the imaging condition setting function 442. Fluoroscopy imaging is an example of moving picture imaging. The processing circuitry 44 that enables the imaging condition setting function 442 is an example of an imaging condition setting unit.

The imaging conditions include at least one of the following: conditions of X-ray irradiation by an X-ray tube (hereinafter, "X-ray conditions"); an AGC (auto gain control) magnification (hereinafter, "AGC magnification"); information regarding an added filter to be used (hereinafter, "filter specifying information"); a detector spatial resolution; a resolution level; a size of a single pixel in an X-ray image (hereinafter, "pixel size"); an FPD pixel size; an FPD element size; an FPD element number; the number of FPD detection elements corresponding to a single pixel of an FPD in a control method in which a plurality of PFD detection elements are treated as a single pixel (this method will be referred to as "binning control" hereinafter); or an imaging mode. The filter specifying information includes at least one of a type of the added filter used, or a thickness of the added filter used, etc. The imaging conditions may be referred to as "fluoroscopy imaging conditions". The imaging condition setting function 442 is an example of an X-ray condition determining unit that determines the X-ray conditions.

The X-ray conditions include at least one of a tube current, a tube voltage, a focal-spot size, a pulse rate (the number of pulse per unit time), a field-of-view size, a source image distance ("SID"), or a duration time of X-ray exposure, etc.

The processing circuitry 44 switches, by the X-ray controlling function 444 and the image generating function 445, an FPD for use in accordance with the selected imaging mode. Upon switching of an FPD for use, the FPD pixel size and the FPD element size are changed. For example, when a normal mode is selected as an imaging mode, the processing circuitry 44 switches the FPD being in use to the FPD1, and performs control of the X-ray conditions corresponding to the normal mode and generation of an X-ray image. For example, when a high-definition mode is selected as an imaging mode, the processing circuitry 44 switches the FPD being in use to the FPD2, controls the X-ray conditions corresponding to the high-definition mode, and generates an X-ray image.

The processing circuitry 44 selects, by the filter selecting function 447, an added filter to be inserted into the path from a focal spot of the X-ray tube to the X-ray detector 13 from the plurality of additional filters based on the following: an FPD element size in the N-th fluoroscopy imaging; a maximum output of X-rays defined by rating, etc. of a tube bulb of an X-ray tube (hereinafter, "maximum power"); an upper limit of an entrance dose of X-rays to the subject per unit time (hereinafter "dose limit"); and a thickness of the subject's body (hereinafter, "body thickness"). The maximum power may be called "an upper limit of an X-ray tube output". The body thickness is an example of subject information. The filter selecting function 447 is an example of a filter selecting unit.

(Imaging Condition Setting Processing)

Figure 8:
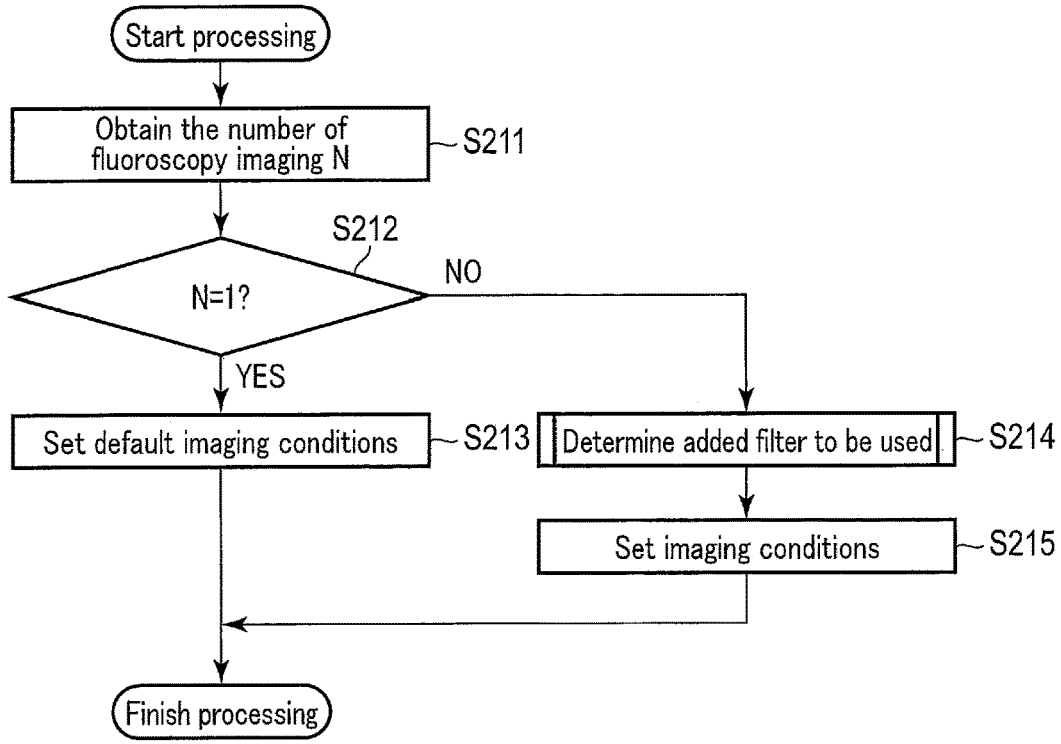
FIG. 8 is a flowchart illustrating a processing procedure of imaging condition setting processing performed by an X-ray diagnosis apparatus according to the fifth embodiment.

Next, the operation of the imaging condition setting processing which is performed by the X-ray diagnosis apparatus 1 will be described. The processing procedure in the imaging condition setting processing which will be described below is merely an example, and the processing can be changed as far as is reasonably possible. Omission, replacement, or addition of a step in the processing procedure described hereinafter can be made as appropriate, in accordance with an actual situation where the present embodiment is realized. FIG. 8 is a flowchart showing an example of the procedure of the imaging condition setting processing according to the present embodiment, and corresponds to the imaging condition setting processing in step S101 shown in FIG. 2. Since the processing in step S212 through step S212 is the same as the processing in step S121 through step S122 in the first embodiment, descriptions thereof are omitted.

(Step S213)

The processing circuitry 44 sets, through the imaging condition setting function 442 and the filter selecting function 447, imaging conditions in fluoroscopy imaging performed for the first time as predetermined conditions. At this time, for example, the processing circuitry 44 sets, by the imaging condition setting function 442, a small focal spot as the focal-spot size, and determines, by the filter selecting function 447, filter D as an added filter to be used. Furthermore, the processing circuitry 44 obtains, by the imaging condition setting function 442, predetermined imaging conditions corresponding to the small focal spot and filter D from the memory 41, and sets the obtained imaging conditions as imaging condition in the N-th fluoroscopy imaging, namely imaging conditions in the impending fluoroscopy imaging. Then, the processing circuitry 44 finishes the imaging condition setting processing, and the processing proceeds to step S103.

(Step S214)

The processing circuitry 44 performs, by the filter selecting function 447, processing of selecting an added filter to be used in the N-th fluoroscopy imaging if the number of times of fluoroscopy imaging is 2 or greater (hereinafter, "filter selecting processing").

(Step S215)

The processing circuitry 44 obtains imaging conditions corresponding to the added filter determined in the processing in step S214 from the memory 41, and sets the obtained imaging conditions as imaging condition in the N-th fluoroscopy imaging, namely imaging conditions in fluoroscopy imaging next performed. Then, the processing circuitry 44 finishes the imaging condition setting processing, and the processing proceeds to step S103.

(Filter Selecting Processing)

Figure 9:
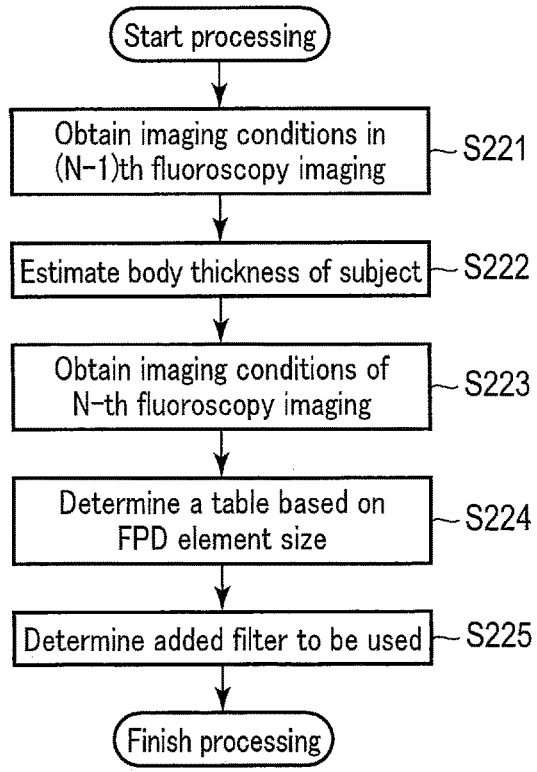
FIG. 9 is a flowchart illustrating a processing procedure of filter selecting processing performed by the X-ray diagnosis apparatus according to the fifth embodiment.

In the following, the operation of the filter selecting processing which is performed by the X-ray diagnosis apparatus 1 will be described. The processing procedure in the filter selecting processing which will be described below is merely an example, and the processing can be changed as far as is reasonably possible. Omission, replacement, or addition of a step in the processing procedure described hereinafter can be made as appropriate, in accordance with an actual situation where the present embodiment is realized. FIG. 9 is a flowchart showing an example of the procedure of the filter selecting processing according to the present embodiment, and corresponds to the filter selecting processing in step S214 shown in FIG. 8.

(Step S221)

The processing circuitry 44 obtains imaging conditions in the (N−1)th fluoroscopy imaging. The processing circuitry 44 reads and obtains the imaging conditions in the (N−1)th fluoroscopy imaging stored in the memory 41. The processing circuitry 44 obtains the imaging conditions for the (N−1)th fluoroscopy imaging so as to obtain imaging conditions in immediately prior fluoroscopy imaging among all the fluoroscopy imaging sessions performed since the commencement of the examination. The processing circuitry 44 obtains, for example, a focal-spot size, filter specifying information, a tube voltage, a tube current, a pulse width, and an AGC magnification, as imaging conditions in the (N−1)th fluoroscopy imaging. As described above, during the fluoroscopy imaging, feedback control is performed to change X-ray conditions, etc. based on the change in the subject conditions, and by the time the fluoroscopy imaging is finished, at least one of the tube voltage, the tube current, the pulse width, or the AGC magnification is in an appropriately controlled state in accordance with the change in the subject conditions. Accordingly, through obtaining imaging conditions in the fluoroscopy imaging performed immediately prior, it is possible to obtain the imaging conditions appropriately controlled in accordance with the change in the subject conditions. Through computation based on an X-ray image generated in the fluoroscopy imaging performed immediately prior, the further appropriately controlled imaging conditions may be calculated in accordance with the change in the subject conditions, and the calculated imaging conditions may be obtained as imaging conditions in the fluoroscopy imaging performed immediately prior.

(Step S222)

The processing circuitry 44 determines the body thickness in the (N−1)th fluoroscopy imaging based on the imaging conditions in the (N−1)th fluoroscopy imaging. Specifically, the processing circuitry 44 calculates an estimate value of the body thickness in the (N−1)th fluoroscopy imaging with a use of the correspondence table stored in the memory 41 in advance, or a known calculation method, based on the filter specifying information, the tube voltage, the tube current, the pulse width, and the AGC magnification at the time the (N−1)th fluoroscopy imaging is concluded. Suppose the body thickness at the time when the (N−1)th fluoroscopy imaging is concluded is the same as the body thickness at the time when the N-th fluoroscopy imaging is commenced. The body thickness at the time when (N−1)th fluoroscopy imaging is concluded is an estimate value of the body thickness calculated based on the X-ray conditions appropriately adjusted in accordance with the change in the subject conditions thorough the foregoing feedback control. The processing circuitry 44 may obtain the body thickness by detecting an operation input that inputs the body thickness at the input interface 43, for example. The estimate value of the body thickness of the subject calculated based on the X-ray conditions adjusted by the feedback control is an example of information regarding the body thickness.

(Step S223)

The processing circuitry 44 obtains an imaging mode, a maximum power, a dose limit, a body thickness, and an SID in the N-th fluoroscopy imaging. In order to do so, the processing circuitry 44 reads, from the memory 41, an imaging mode, a maximum power, a dose limit, a body thickness, and an SID in the N-th fluoroscopy imaging, for example.

Furthermore, the processing circuitry 44 obtains an FPD element size in the N-th fluoroscopy imaging by, for example, detecting an operation input in the display 42 which is used as an input interface 43. For example, if the imaging mode is a normal mode, the processing circuitry 44 obtains an element size of the detector element of the FPD1 as the FPD element size in the N-th fluoroscopy imaging. If the imaging mode is a high-definition mode, the processing circuitry 44 obtains an element size of the detector element of the FPD2 as the FPD element size in the N-th fluoroscopy imaging.

(Step S224)

The processing circuitry 44 reads a corresponding correspondence table from a plurality of correspondence tables stored in the memory 41 based on the FPD element size in the N-th fluoroscopy imaging obtained in the processing in step S223.

FIGS. 10 and 11 show examples of correspondence table used in the processing of determining an added filter in step S224. FIG. 10 is an example of correspondence table which is used when the imaging mode is a normal mode. FIG. 11 is an example of correspondence table which is used when the imaging mode is a high-definition mode. Each of FIGS. 10 and 11 shows a relationship of the maximum power, the dose limit, the SID, and the body thickness to the used added filter. For example, FIG. 10 shows the relationship in which a thinner added filter is used for the same maximum power if the dose limit, the SID, and the body thickness is larger (although, the thickness of the added filter: A>B>C>D). This relationship prominently appears when the body thickness exceeds 25 cm. FIG. 11 also shows a similar relationship. The processing circuitry 44 reads the correspondence table shown in FIG. 10 if the imaging mode is a normal mode, in other words, when the FPD element size in the N-th fluoroscopy imaging is the element size of the detector element of the FPD1. The processing circuitry 44 reads the correspondence table shown in FIG. 11 if the imaging mode is a high-definition mode, in other words, if the FPD element size in the N-th fluoroscopy imaging is an element size of the detection element of the FPD2.

(Step S225)

The processing circuitry 44 determines an added filter used in the N-th fluoroscopy imaging from filters A through D, based on the correspondence table read from the processing in step S224, the maximum power, the dose limit, SID, and the body thickness in the N-th fluoroscopy imaging. The processing circuitry 44 stores the filter specifying information regarding the determined added filter in the memory 41.

In the processing in step S224 and step S225, if the FPD element size is large, the processing circuitry 44 selects an added filter having a thickness larger than that of the added filter selected in the case of a small FPD element size. For example, the processing circuitry 44 selects a first filter having a first thickness if the FPD element size is a first size, and selects a second filter having a second thickness, which is larger than the first thickness, if the FPD element size is a second size, which is larger than the first size. To be more precise, in this example, whether or not the FPD element size is large corresponds to whether or not the FPD element size is of a second size when it can be of either a first size or a second size. In other words, in this example, the case of a large FPD element size corresponds to a case where the FPD element size is of a second size when it can be of either a first size or a second size. However, the embodiment is not limited to this example; a reference value between a first size and a second size may be used to determine whether or not the FPD element size is large in accordance with whether or not the FPD element size is larger than the reference value. The same determination can be made with respect to whether or not the FPD pixel size is large. Similarly, the case of a small FPD element size (or the FPD pixel size) corresponds to a case where the FPD element size is of a first size when it can be of either a first size or a second size. The embodiment is not limited to this example, and a case of a small the FPD element size (or the FPD pixel size) can be determined with the use of the relationship with the reference value The processing circuitry 44 may obtain an FPD pixel size based on an FPD element size. In this case, if the FPD pixel size is large, the processing circuitry 44 selects an added filter having a thickness larger than that of the added filter selected in the case of a small FPD pixel size. For example, the processing circuitry 44 selects a first filter having a first thickness if the FPD pixel size is a first size, and selects a second filter having a second thickness, which is larger than the first thickness, if the FPD pixel size is a second size, which is larger than the first size.

The processing circuitry 44 selects, if the imaging mode is a normal mode, an added filter having a thickness larger than that of an added filter selected in the case where the imaging mode is a high-definition mode. The processing circuitry 44 selects, if the maximum power is large, an added filter having a thickness larger than that of an added filter selected in the case where the maximum power is small. The processing circuitry 44 selects, if the dose limit is small, an added filter having a thickness larger than that of an added filter selected in the case where the dose limit is large. The processing circuitry 44 selects, if the SID is small, an added filter having a thickness larger than that of an added filter selected in the case where the SID is large. The processing circuitry 44 selects, if the thickness is small, an added filter having a thickness larger than that of an added filter selected in the case where the thickness is large.

In the following description, advantageous effects of the X-ray diagnosis apparatus 1 according to the present embodiment will be described.

The X-ray diagnosis apparatus 1 of the present embodiment selects, from a plurality of filters, a filter to be inserted into the X-ray path from the focal spot of the X-ray tube to the X-ray detector 13, based on a pixel size in the X-ray detector 13 and the information regarding the body thickness of the subject.

Specifically, the X-ray diagnosis apparatus 1 of the present embodiment selects an added filter to be inserted into the path from the focal spot of the X-ray tube to the X-ray detector 13 from the plurality of additional filters based on the FPD element size and the body thickness in fluoroscopy imaging performed next. The X-ray diagnosis apparatus 1 of the present embodiment selects an added filter to be inserted into the path from the focal spot of the X-ray tube to the X-ray detector 13 from the plurality of additional filters based on the FPD pixel size and the body thickness in next fluoroscopy imaging.

The X-ray diagnosis apparatus 1 of the present embodiment obtains a pixel size in the X-ray detector 13 based on the size of the detection element, and if the pixel size in the X-ray detector 13 is large, selects, as a filter to be inserted into the X-ray path from a focal spot of the X-ray tube to the X-ray detector 13, a filter having a thickness larger than that of a filter selected in the case where the pixel size in the X-ray detector 13 is small, based on the pixel size and the information regarding the body thickness of the subject.

In summary, the X-ray diagnosis apparatus 1 of the present embodiment selects an added filter having a large thickness if the FPD element size is large, compared to the case where the FPD element size is small. The X-ray diagnosis apparatus 1 of the present embodiment selects an added filter having a large thickness if the FPD pixel size is large, compared to the case where the FPD pixel size is small.

In other words, according to the X-ray diagnosis apparatus 1 of the present embodiment, with the above-described configurations and operations, an appropriate added filter can be selected by considering the FPD element size and the body thickness in tandem with the change in a target dose.

For example, if the FPD element size is large, the FPD element size becomes larger and the target dose becomes smaller compared to the case where the FPD element size is small. For this reason, if the FPD element size is large, it is relatively easy to secure a target dose, even when an added filter having a large thickness is used. According to the X-ray diagnosis apparatus 1 of the present embodiment, if the FPD element size is large, an added filter having a large thickness is selected compared to the case where the FPD element size is small. For this reason, in the case where the target dose can be easily secured, it is possible to secure image quality of an X-ray image and reduce an exposure dose of the subject through selecting an added filter having a large X-ray reduction rate.

For example, if the FPD element size is small, the FPD pixel size becomes smaller and the target dose becomes larger, compared to the case where the FPD element size is large. For this reason, if the FPD element size is small, it is difficult to secure a target dose, when an added filter having a small thickness is used. According to the X-ray diagnosis apparatus 1 of the present embodiment, if the FPD element size is small, an added filter having a small thickness is selected, compared to the case where the FPD element size is large. For this reason, in the case where the target dose cannot be easily secured, it is possible to select an appropriate added filter in accordance with the target dose through selecting an added filter having a small X-ray reduction rate.

Furthermore, the X-ray diagnosis apparatus 1 of the present embodiment selects, from a plurality of filters, a filter to be inserted into the path from the focal spot of the X-ray tube to the X-ray detector 13, based on at least one of the following: a pixel size in the X-ray detector 13, information regarding the body thickness of the subject, a maximum output of the X-ray tube, an upper limit of an entrance dose of X-rays to the subject per unit time, or an SID.

In summary, the X-ray diagnosis apparatus 1 of the present embodiment selects a more appropriate added filter to be inserted into the X-ray path from the focal spot of the X-ray tube to the X-ray detector 13 from the plurality of additional filters based on, in addition to the FPD pixel size and the body thickness, at least one of the maximum power, the dose limit, and the SID.

Sixth Embodiment

Next, the sixth embodiment will be described. The present embodiment is a modification of the configuration of the sixth embodiment as will be described below. In the present embodiment, the processing circuitry 44 determines an added filter to be used in next fluoroscopy imaging based on the number of "bins", instead of the FPD element size. The number of bins is the number of FPD detection elements corresponding to one pixel of an FPD in a control method (binning control) in which a plurality of FPD detection elements as one pixel of the FPD. Descriptions of the configurations, operations, and advantageous effects similar to those of the first embodiment will be omitted.

A single type of FPD is provided in the X-ray detector 13.

The processing circuitry 44 selects, through the filter selecting function 447, from a plurality of additional filters, an added filter to be inserted into the path from the focal spot of the X-ray tube to the X-ray detector 13 based on the number of bins, the maximum power, the dose limit, and the body thickness in the N-th fluoroscopy imaging. Herein, the FPD pixel size changes in accordance with the change in the number of bins. In other words, the processing circuitry 44 selects, through the filter selecting function 447, from a plurality of additional filters, an added filter to be inserted into the path from the focal spot of the X-ray tube to the X-ray detector 13 based on the FPD pixel size, the maximum power, the dose limit, and the body thickness in the N-th fluoroscopy imaging.

The processing circuitry 44 controls the number of bins, by the X-ray controlling function 444 and the image generating function 445, so as to switch the FPD pixel size in accordance with the selected imaging mode. For example, if a normal mode is selected as the imaging mode, the processing circuitry 44 controls the number of bins to four, and controls the FPD pixel size as four detection elements of the FPD. In this case, taking four detection elements of the FPD as a single pixel of the FPD, the processing circuitry 44 bundles the output from these four detection elements into one, and reads it as an output corresponding to a single pixel of the FPD. For example, when a high-definition mode is selected as the imaging mode, the processing circuitry 44 controls the number of bins to 1, and controls the FPD pixel size as one detection element of the FPD. In this case, the processing circuitry 44 takes a single detection element of the FPD as a single pixel of the FPD, and reads an output of each of the detection elements of the FPD as an output corresponding to a pixel of the FPD.

The other configurations are the same as those of the fifth embodiment.

Figure 12:
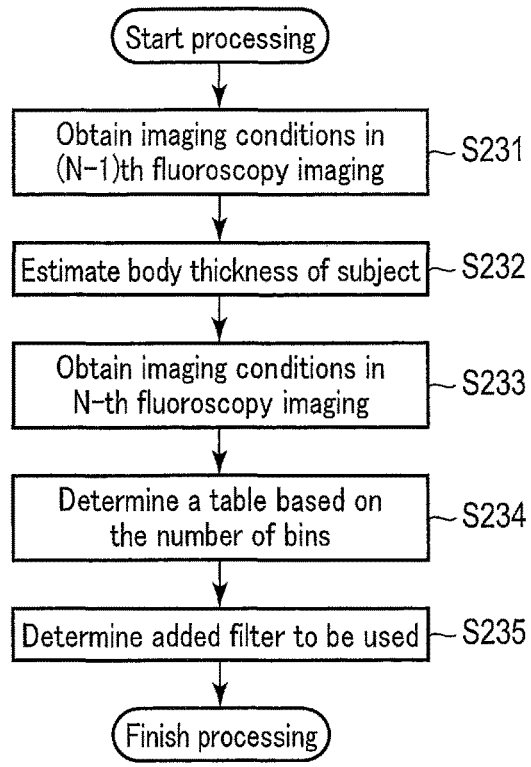
FIG. 12 is a flowchart illustrating a processing procedure of filter selecting processing performed by an X-ray diagnosis apparatus according to a sixth embodiment.

In the following, the operation of the filter selecting processing which is performed by the X-ray diagnosis apparatus 1 will be described. FIG. 12 is a flowchart showing an example of the procedure of the filter selecting processing performed by the X-ray diagnosis apparatus 1 of the present embodiment, and corresponds to the filter selecting processing in step S214 shown in FIG. 8. Since the processing in step 231 through step S232 in FIG. 12 is the same as the processing step S221 through step S222 in the fifth embodiment, descriptions thereof are omitted.

(Filter Selecting Processing)

(Step S233)

The processing circuitry 44 obtains imaging conditions in N-th fluoroscopy imaging. The processing circuitry 44 reads from the memory 41, imaging conditions in the N-th fluoroscopy imaging, for example. The processing circuitry 44 obtains imaging conditions in next fluoroscopy imaging by obtaining imaging conditions in the N-th fluoroscopy imaging. The processing circuitry 44 obtains, for example, the number of bins, a maximum power, a dose limit, a body thickness, and an SID as the imaging conditions in the N-th fluoroscopy imaging.

(Step S234)

The processing circuitry 44 reads a corresponding correspondence table from a plurality of correspondence tables stored in the memory 41 based on the number of bins in the N-th fluoroscopy imaging obtained in the processing in step S233. For example, if the number of bins is 4, the correspondence table of FIG. 10 is selected. For example, if the number of bins is 1, the correspondence table of FIG. 11 is selected.

(Step S235)

The processing circuitry 44 determines an added filter used in the N-th fluoroscopy imaging from filters A through D, based on the correspondence table read from the processing in step S234, the maximum power, the dose limit, the SID, and the body thickness in the N-th fluoroscopy imaging.

In the processing in step S234 and step S235, if the number of bins is large, the processing circuitry 44 selects an added filter having a thickness larger than that of the added filter selected in the case where the number of bins is small. In other words, if the FPD pixel size is large, the processing circuitry 44 selects an added filter having a thickness larger than that of the added filter selected in the case of a small FPD pixel size. For example, the processing circuitry 44 selects a first filter having a first thickness if the number of bins is a first size, and selects a second filter having a second thickness, which is larger than the first thickness, if the number of bins is a second size, which is larger than the first size. The processing circuitry 44 obtains an FPD pixel size based on the number of bins. In this case, if the FPD pixel size is large, the processing circuitry 44 selects an added filter having a thickness larger than that of the added filter selected in the case of a small FPD pixel size. For example, the processing circuitry 44 selects a first filter having a first thickness if the FPD pixel size is a first size, and selects a second filter having a second thickness (which is larger than the first thickness) if the FPD pixel size is a second size (which is larger than the first size). Since the other processing is the same as that in step S224 and step S225 of the fifth embodiment, descriptions of the processing are omitted.

In the following description, advantageous effects of the X-ray diagnosis apparatus 1 according to the present embodiment will be described.

The X-ray diagnosis apparatus 1 of the present embodiment obtains a pixel size in the X-ray detector 13 based on the number of detection elements corresponding to a single pixel of the X-ray detector 13, and if the pixel size in the X-ray detector 13 is large, selects, as a filter to be inserted into the X-ray path from a focal spot of the X-ray tube to the X-ray detector 13, a filter having a thickness larger than that of a filter selected in the case where the pixel size in the X-ray detector 13 is small, based on the pixel size and the information regarding the body thickness of the subject.

In summary, the X-ray diagnosis apparatus 1 of the present embodiment selects an added filter to be inserted into the path from the focal spot of the X-ray tube to the X-ray detector 13 from the plurality of additional filters based on the number of bins and the body thickness in next fluoroscopy imaging. The X-ray diagnosis apparatus 1 of the present embodiment selects an added filter having a large thickness when the number of bins is large, compared to the case where the number of bins is small.

When the number of bins is different, the FPD pixel size is also different; as a consequence, the target dose is different, and an appropriate added filter is different. According to the X-ray diagnosis apparatus 1 of the present embodiment, with the above-described configurations and operations, an appropriate added filter can be selected by considering the FPD element size and body thickness in tandem with the change in a target dose.

For example, if the FPD element size is large, the FPD element size becomes larger and the target dose becomes smaller compared to the case where the FPD element size is small. For this reason, if the FPD element size is large, it is relatively easy to secure a target dose, even when an added filter having a large thickness is used. The X-ray diagnosis apparatus 1 of the present embodiment selects an added filter having a large thickness when the number of bins is large, compared to the case where the number of bins is small. For this reason, in the case where the target dose can be easily secured, it is possible to secure image quality of an X-ray image and reduce an exposure dose of the subject through selecting an added filter having a large X-ray reduction rate.

For example, if the FPD element size is small, the FPD pixel size becomes smaller and the target dose becomes larger, compared to the case where the FPD element size is large. For this reason, if the FPD element size is small, it is difficult to secure a target dose, when an added filter having a small thickness is used. According to the X-ray diagnosis apparatus 1 of the present embodiment, if the FPD element size is small, an added filter having a small thickness is selected, compared to the case where the FPD element size is large. For this reason, in the case where the target dose cannot be easily secured, it is possible to select an appropriate added filter in accordance with the target dose through selecting an added filter having a small X-ray reduction rate.

Seventh Embodiment

Next, the seventh embodiment will be described. The present embodiment is a modification of the configuration of the fifth embodiment as will be described below. In the present embodiment, the processing circuitry 44 determines an added filter to be used in next fluoroscopy imaging based on a pixel size in an X-ray image based on an output of the X-ray detector 13, instead of an FPD element size. Descriptions of the configurations, operations, and advantageous effects similar to those of the fifth embodiment will be omitted.

A single type of FPD is provided in the X-ray detector 13. The processing circuitry 44 selects, through the filter selecting function 447, from a plurality of additional filters, an added filter to be inserted into the path from the focal spot of the X-ray tube to the X-ray detector 13 based on a pixel size, a maximum power, a dose limit, and a body thickness in the N-th fluoroscopy imaging.

The processing circuitry 44 switches, through the X-ray controlling function 444 and the image generating function 445, a pixel size in accordance with a selected imaging mode. For example, if a normal mode is selected as the imaging mode, the processing circuitry 44 controls the pixel size as four FPD pixels. In this case, the processing circuitry 44 bundles the output from the four FPD pixels into one, and reads it as an output corresponding to a single pixel of the X-ray image. For example, when a high-definition mode is selected as the imaging mode, the processing circuitry 44 controls the pixel size as a single FPD pixel. In this case, the processing circuitry 44 reads an output of each of the FPD pixels as an output corresponding to a single pixel of the X-ray image. The pixel size of a single FPD pixel is an example of a first size of the pixel size. The pixel size of four FPD pixels is an example of a second size of the pixel size.

The other configurations are the same as those of the fifth embodiment.

Figure 13:
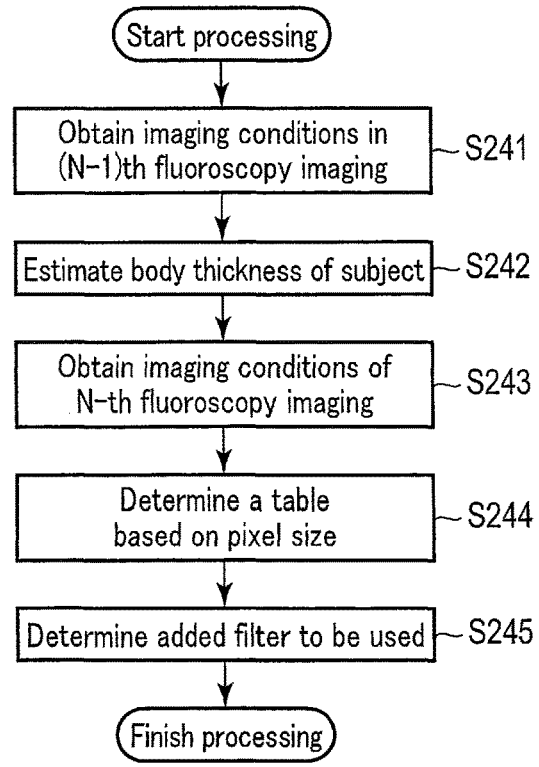
FIG. 13 is a flowchart illustrating a processing procedure of filter selecting processing performed by an X-ray diagnosis apparatus according to a seventh embodiment.

In the following, the operation of the filter selecting processing which is performed by the X-ray diagnosis apparatus 1 will be described. FIG. 13 is a flowchart showing an example of the procedure of the filter selecting processing performed by the X-ray diagnosis apparatus 1 of the present embodiment, and corresponds to the filter selecting processing in step S214 shown in FIG. 8. Since the processing in step 241 through step S242 in FIG. 13 is the same as the processing step S221 through step S222 in the fifth embodiment, descriptions thereof are omitted.

(Filter Selecting Processing)

(Step S243)

The processing circuitry 44 obtains imaging conditions in (N−1)th fluoroscopy imaging. The processing circuitry 44 reads from the memory 41, imaging conditions in the N-th fluoroscopy imaging, for example. The processing circuitry 44 obtains imaging conditions in next fluoroscopy imaging by obtaining imaging conditions in the N-th fluoroscopy imaging. The processing circuitry 44 obtains, for example, a pixel size, a maximum power, a dose limit, a body thickness, and an SID as the imaging conditions in the N-th fluoroscopy imaging.

(Step S244)

The processing circuitry 44 reads a corresponding correspondence table from a plurality of correspondence tables stored in the memory 41 based on the pixel size in the N-th fluoroscopy imaging obtained in the processing in step S243. For example, if the pixel size is defined as four FPD pixels, the correspondence table of FIG. 10 is selected. For example, if the pixel size is a single FPD pixel, the correspondence table of FIG. 11 is selected.

(Step S245)

The processing circuitry 44 determines an added filter used in the N-th fluoroscopy imaging from filters A through D, based on the correspondence table read from the processing in step S244, the maximum power, the dose limit, SID, and the body thickness in the N-th fluoroscopy imaging.

In the processing in step S244 and step S245, if the pixel size is large, the processing circuitry 44 selects an added filter having a thickness larger than that of the added filter selected in the case of a small pixel size. For example, the processing circuitry 44 selects a first filter having a first thickness if the pixel size is a first size, and selects a second filter having a second thickness (which is larger than the first thickness) if the pixel size is a second size (which is larger than the first size). Since the other processing is the same as that in step S224 and step S225 of the fifth embodiment, descriptions of the processing are omitted.

In the following description, advantageous effects of the X-ray diagnosis apparatus 1 according to the present embodiment will be described.

If the pixel size in the X-ray detector 13 is large, the X-ray diagnosis apparatus 1 of the present embodiment selects, as a filter to be inserted into the X-ray path from a focal spot of the X-ray tube to the X-ray detector 13, a filter having a thickness larger than that of a filter selected in the case where the pixel size in the X-ray image based on the output of the X-ray detector 13 is small, based on the pixel size and the information regarding the body thickness of the subject.

In summary, the X-ray diagnosis apparatus 1 of the present embodiment selects an added filter to be inserted into the path from the focal spot of the X-ray tube to the X-ray detector 13 from the plurality of additional filters based on the pixel size and the body thickness, and selects an added filter having a large thickness if the pixel size is large, compared to the case of a small pixel size.

In other words, according to the X-ray diagnosis apparatus 1 of the present embodiment, with the above-described configurations and operations, an appropriate added filter can be selected by considering the pixel size and the body thickness in tandem with the change in a target dose.

For example, if the pixel size is large, the target dose becomes smaller compared to the case of a small pixel size; as a result, it is relatively easy to secure the target dose even when an added filter having a large thickness is used. According to the X-ray diagnosis apparatus 1 of the present embodiment, if the pixel size is large, an added filter having a large thickness is selected compared to the case where the FPD element size is small. For this reason, in the case where the target dose can be easily secured, it is possible to secure image quality of an X-ray image and reduce an exposure dose of the subject through selecting an added filter having a large X-ray reduction rate.

Furthermore, if the pixel size is small for example, the target dose becomes larger compared to the case of a large pixel size; as a result, it is difficult to secure the target dose when an added filter having a small thickness is used. According to the X-ray diagnosis apparatus 1 of the present embodiment, if the pixel size is small, an added filter having a small thickness is selected, compared to the case where the pixel size is large. For this reason, in the case where the target dose cannot be easily secured, it is possible to select an appropriate added filter in accordance with the target dose through selecting an added filter having a small X-ray reduction rate.

Eighth Embodiment

Next, the eighth embodiment will be described. The present embodiment is a modification of the configuration of the fifth embodiment as will be described below. In the present embodiment, the processing circuitry 44 determines an added filter to be used in next fluoroscopy imaging based on a field-of-view size, instead of the FPD element size. Descriptions of the configurations, operations, and advantageous effects similar to those of the fifth embodiment will be omitted.

The processing circuitry 44 selects, through the filter selecting function 447, from a plurality of additional filters, an added filter to be inserted into the path from the focal spot of the X-ray tube to the X-ray detector 13 based on a field-of-view size, a maximum power, a dose limit, and a body thickness in the N-th fluoroscopy imaging.

The other configurations are the same as those of the fifth embodiment.

In the following, the operation of the filter selecting processing which is performed by the X-ray diagnosis apparatus 1 will be described. FIG. 14 is a flowchart showing an example of the procedure of the filter selecting processing performed by the X-ray diagnosis apparatus 1 of the present embodiment, and corresponds to the filter selecting processing in step S214 shown in FIG. 8. Since the processing in step 251 through step S252 in FIG. 14 is the same as the processing step S221 through step S222 in the fifth embodiment, descriptions thereof are omitted.

(Filter Selecting Processing)

(Step S253)

The processing circuitry 44 obtains imaging conditions in N-th fluoroscopy imaging. The processing circuitry 44 reads imaging conditions in the N-th fluoroscopy imaging from the memory 41, for example. The processing circuitry 44 obtains imaging conditions in next fluoroscopy imaging by obtaining imaging conditions in the N-th fluoroscopy imaging. The processing circuitry 44 obtains, for example, a field-of-view size, a maximum power, a dose limit, a body thickness, and an SID as the imaging conditions in the N-th fluoroscopy imaging.

(Step S254)

The processing circuitry 44 reads a corresponding correspondence table from a plurality of correspondence tables stored in the memory 41 based on the field-of-view size in the N-th fluoroscopy imaging obtained in the processing in step S253. For example, if the field-of-view size is a first size, the correspondence table of FIG. 11 is selected. For example, if the field-of-view size is a second size larger than the first size, the correspondence table of FIG. 10 is selected.

(Step S255)

The processing circuitry 44 determines an added filter used in the N-th fluoroscopy imaging from filters A through D, based on the correspondence table read from the processing in step S254, the maximum power, the dose limit, SID, and the body thickness in the N-th fluoroscopy imaging.

In the processing in step S254 and step S255, if the field-of-view size is large, the processing circuitry 44 selects an added filter having a thickness larger than that of the added filter selected in the case of a field-of-view size. For example, the processing circuitry 44 selects a first filter having a first thickness if the field-of-view size is a first size, and selects a second filter having a second thickness, which is larger than the first thickness, if the field-of-view size is a second size, which is larger than the first size. Since the other processing is the same as that in step S224 and step S225 of the fifth embodiment, descriptions of the processing are omitted.

In the following description, advantageous effects of the X-ray diagnosis apparatus 1 according to the present embodiment will be described.

If the X-ray irradiation area is large, the X-ray diagnosis apparatus 1 of the present embodiment selects, as a filter to be inserted into the X-ray path from the focal spot of the X-ray tube to the X-ray detector 13, a filter having a thickness larger than that selected in the case where the X-ray irradiation area is small, based on the size of the X-ray irradiation area and the information regarding the body thickness of the subject.

In summary, the X-ray diagnosis apparatus 1 of the present embodiment selects an added filter to be inserted into the path from the focal spot of the X-ray tube to the X-ray detector 13 from the plurality of additional filters based on the field-of-view size and the body thickness, and selects an added filter having a large thickness if the field-of-view size is large, compared to the case of a small field-of-view size.

If fluoroscopy imaging is performed with a different field-of-view size, the influence of scattered radiation and a target dose become different; thus, an appropriate added filter will also be different. According to the X-ray diagnosis apparatus 1 of the present embodiment, with the above-described configurations and operations, an appropriate added filter can be selected by considering the field-of-view size and the body thickness in tandem with the influence of scattered radiation and the target dose.

For example, if the field-of-view size is large, the X-ray irradiation area becomes larger; as a result, the scattered radiation increases compared to the case where a field-of-view size is small. If the scattered radiation increases, a dose of X-rays that enters the X-ray detector 13 also increases; accordingly, it is relatively easy to secure a target dose even if an added filter having a large thickness is used. According to the X-ray diagnosis apparatus 1 of the present embodiment, if the field-of-view size is large, an added filter having a large thickness is selected, compared to the case where a field-of-view size is small. For this reason, in the case where the target dose can be easily secured, it is possible to secure image quality of an X-ray image and reduce an exposure dose of the subject through selecting an added filter having a large X-ray reduction rate.

For example, if the field-of-view size is small, the X-ray irradiation area becomes smaller; as a result, the scattered radiation decreases compared to the case where a field-of-view size is large. If the scattered radiation decreases, a dose of X-rays that enters the X-ray detector 13 also decreases; accordingly, it is relatively easy to secure a target dose even if an added filter having a small thickness is used. According to the X-ray diagnosis apparatus 1 of the present embodiment, if the field-of-view size is small, an added filter having a small thickness is selected, compared to the case where the field-of-view size is large. For this reason, in the case where the target dose cannot be easily secured, it is possible to select an appropriate added filter in accordance with the target dose through selecting an added filter having a small X-ray reduction rate.

Ninth Embodiment

Next, the ninth embodiment will be described. The present embodiment is a modification of the configuration of the fifth embodiment as will be described below. In the present embodiment, the processing circuitry 44 determines an added filter to be used in next fluoroscopy imaging based on a focal-spot size, instead of the FPD element size. Descriptions of the configurations, operations, and advantageous effects similar to those of the fifth embodiment will be omitted.

The processing circuitry 44 selects, through the filter selecting function 447, from a plurality of additional filters, an added filter to be inserted into the path from the focal spot of the X-ray tube to the X-ray detector 13 based on a focal-spot size, a maximum power, a dose limit, and a body thickness in N-th fluoroscopy imaging.

The other configurations are the same as those of the fifth embodiment.

In the following, the operation of the filter selecting processing which is performed by the X-ray diagnosis apparatus 1 will be described. FIG. 15 is a flowchart showing an example of the procedure of the filter selecting processing performed by the X-ray diagnosis apparatus 1 of the present embodiment, and corresponds to the filter selecting processing in step S214 shown in FIG. 8. Since the processing in step 261 through step S262 in. FIG. 15 is the same as the processing step S221 through step S222 in the fifth embodiment, descriptions thereof are omitted.

(Filter Selecting Processing)
(Step S263)

The processing circuitry 44 obtains imaging conditions in N-th fluoroscopy imaging. The processing circuitry 44 reads from the memory 41, imaging conditions in N-th fluoroscopy imaging, for example. The processing circuitry 44 obtains imaging conditions in next fluoroscopy imaging by obtaining the imaging conditions in the N-th fluoroscopy imaging. The processing circuitry 44 obtains, for example, a focal-spot size, a maximum power, a dose limit, a body thickness, and an SID as the imaging conditions in the N-th fluoroscopy imaging.

(Step S264)

The processing circuitry 44 reads a corresponding correspondence table from a plurality of correspondence tables stored in the memory 41 based on the focal-spot size in the N-th fluoroscopy imaging obtained in the processing in step S263. For example, if the focal-spot size is a medium focal spot, the correspondence table of FIG. 10 is selected. For example, if the focal-spot size is a small focal spot, the correspondence table of FIG. 11 is selected.

(Step S265)

The processing circuitry 44 determines an added filter used in the N-th fluoroscopy imaging from filters A through D, based on the correspondence table read from the processing in step S264, the maximum power, the dose limit, the SID, and the body thickness in the N-th fluoroscopy imaging.

In the processing in step S264 and step S265, if the focal-spot size is large, the processing circuitry 44 selects an added filter having a thickness larger than that of the added filter selected in the case where the focal-spot size is small. For example, the processing circuitry 44 selects a first filter having a first thickness if the focal-spot size is a small focal spot, and selects a second filter having a second thickness, which is larger than the first thickness, if the focal-spot size is a medium focal spot. Since the other processing is the same as that in step S224 and step S225 of the fifth embodiment, descriptions of the processing are omitted.

In the following description, advantageous effects of the X-ray diagnosis apparatus 1 according to the present embodiment will be described.

The X-ray diagnosis apparatus 1 of the present embodiment selects a filter to be inserted into the X-ray path from the focal spot of the X-ray tube to the X-ray detector 13, based on the information regarding the body thickness of the subject and the focal-spot size of the tube bulb of the X-ray tube. If the focal-spot size is large, the filter selecting unit selects, as a filter to be inserted into the X-ray path of the X-rays from the focal spot of the X-ray tube to the X-ray detector 13, a filter having a thickness larger than the thickness of a filter selected in the case where the focal-spot size is small.

In summary, the X-ray diagnosis apparatus 1 of the present embodiment selects an added filter to be inserted into the path from the focal spot of the X-ray tube to the X-ray detector 13 from the plurality of additional filters based on the focal-point size, the maximum power, the dose limit, and the body thickness. The X-ray diagnosis apparatus 1 of the present embodiment selects an added filter having a large thickness if the focal-spot size is large, compared to the case where the focal-spot size is small.

If fluoroscopy imaging is performed with a different focal-point size, the maximum power of the tube bulb becomes different; thus, an appropriate added filter will also be different. According to the X-ray diagnosis apparatus 1 of the present embodiment, with the above-described configurations and operations, an appropriate added filter can be selected by considering the focal-spot size and the body thickness in tandem with the change in the maximum power.

For example, if the focal-spot size is large, the maximum power of the tube bulb is large, and it is thereby easy to increase the output of the tube bulb, compared to the case where the focal-spot size is small. For this reason, it is relatively easy to secure a target dose even when an added filter having a large thickness is used. According to the X-ray diagnosis apparatus 1 of the present embodiment, if the focal-spot size is large, an added filter having a large thickness is selected compared to the case where a focal-spot size is small. For this reason, in the case where the target dose can be easily secured, it is possible to secure image quality of an X-ray image and reduce an exposure dose of the subject through selecting an added filter having a large X-ray reduction rate.

For example, if the focal-spot size is small, the maximum power of the tube bulb is small, and it is thereby easy to increase the output of the tube bulb, compared to the case where the focal-spot size is large. For this reason, it is relatively difficult to secure a target dose, when an added filter having a small thickness is used. According to the X-ray diagnosis apparatus 1 of the present embodiment, if the focal-spot size is small, an added filter having a small thickness is selected, compared to the case where the pixel size is small. For this reason, in the case where the target dose cannot be easily secured, it is possible to select an appropriate added filter in accordance with the target dose through selecting an added filter having a small X-ray reduction rate.

Tenth Embodiment

Next, the tenth embodiment will be described. The present embodiment is a modification of the configuration of the fifth embodiment as will be described below. In the present embodiment, the processing circuitry 44 determines an added filter to be used in next fluoroscopy imaging based on a pulse rate, instead of an FPD element size. Descriptions of the configurations, operations, and advantageous effects similar to those of the fifth embodiment will be omitted.

The processing circuitry 44 selects, through the filter selecting function 447, from a plurality of additional filters, an added filter to be inserted into the path from the focal spot of the X-ray tube to the X-ray detector 13 based on a pulse rate, a maximum power, a dose limit, and a body thickness in N-th fluoroscopy imaging.

The other configurations are the same as those of the fifth embodiment.

Figure 16:
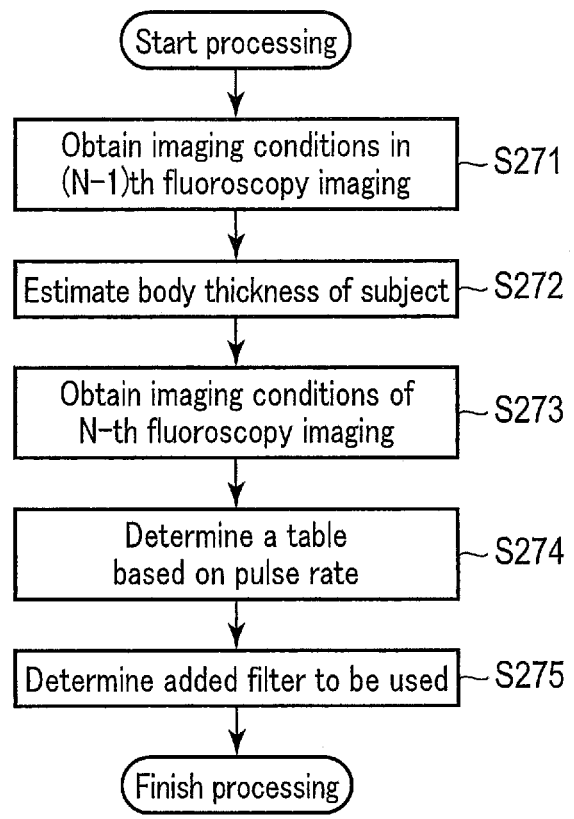
FIG. 16 is a flowchart illustrating a processing procedure of filter selecting processing performed by an X-ray diagnosis apparatus according to a tenth embodiment.

In the following, the operation of the filter selecting processing which is performed by the X-ray diagnosis apparatus 1 will be described. FIG. 16 is a flowchart showing an example of the procedure of the filter selecting processing performed by the X-ray diagnosis apparatus 1 of the present embodiment, and corresponds to the filter selecting processing in step S214 shown in FIG. 8. Since the processing in step 241 through step S271 in FIG. 16 is the same as the processing step S221 through step S222 in the fifth embodiment, descriptions thereof are omitted.

(Filter Selecting Processing)

(Step S273)

The processing circuitry 44 obtains imaging conditions in N-th fluoroscopy imaging. The processing circuitry 44 reads imaging conditions in N-th fluoroscopy imaging from the memory 41, for example. The processing circuitry 44 obtains imaging conditions in next fluoroscopy imaging by obtaining the imaging conditions in the N-th fluoroscopy imaging. The processing circuitry 44 obtains, for example, a pulse rate, a maximum power, a dose limit, a body thickness, and an SID as the imaging conditions in the N-th fluoroscopy imaging.

(Step S274)

The processing circuitry 44 reads a corresponding correspondence table from a plurality of correspondence tables stored in the memory 41 based on the pulse rate in the N-th fluoroscopy imaging obtained in the processing in step S273. For example, if the pulse rate is a first size, the correspondence table of FIG. 11 is selected. For example, if the pulse rate is a second size larger than the first size, the correspondence table of FIG. 10 is selected.

(Step S275)

The processing circuitry 44 determines an added filter used in the N-th fluoroscopy imaging from filters A through D, based on the correspondence table read from the processing in step S274, the maximum power, the dose limit, the SID, and the body thickness in the N-th fluoroscopy imaging.

In the processing in step S274 and step S275, if the pulse rate is large, the processing circuitry 44 selects an added filter having a thickness larger than that of the added filter selected in the case where the pulse rate is small. For example, the processing circuitry 44 selects a first filter having a first thickness if the pulse rate is a first size, and selects a second filter having a second thickness (which is larger than the first thickness) if the pulse rate is a second size (which is larger than the first size). Since the other processing is the same as that in step S224 and step S225 of the fifth embodiment, descriptions of the processing are omitted.

In the following description, advantageous effects of the X-ray diagnosis apparatus 1 according to the present embodiment will be described.

The X-ray diagnosis apparatus 1 of the present embodiment selects a filter to be inserted into the X-ray path from the focal spot of the X-ray tube to the X-ray detector 13, based on the information regarding the body thickness of the subject and the pulse rate of X-rays generated from the X-ray tube. If the pulse rate is large, the filter selecting unit selects, as a filter to be inserted into the X-ray path of the X-rays from the focal spot of the X-ray tube to the X-ray detector 13, a filter having a thickness larger than the thickness of a filter selected in the case where the pulse rate is small.

In summary, the X-ray diagnosis apparatus 1 of the present embodiment selects an added filter to be inserted into the path from the focal spot of the X-ray tube to the X-ray detector 13 from the plurality of additional filters based on the pulse rate, the maximum power, the dose limit, and the body thickness. The X-ray diagnosis apparatus 1 of the present embodiment selects an added filter having a large thickness if the pulse rate is large, compared to the case where the pulse rate is small.

If fluoroscopy imaging is performed with a different pulse rate, a dose of X-rays that enters the subject in the fluoroscopy imaging becomes different; as a result, the ratio of (the X-ray dose entering the subject):(the dose limit) will also be different. For this reason, if fluoroscopy imaging is performed with a different pulse rate, an appropriate added filter is different. According to the X-ray diagnosis apparatus 1 of the present embodiment, with the above-described configurations and operations, an appropriate added filter can be selected by considering the pulse rate and the body thickness in tandem with the ratio of the X-ray dose that enters the subject to the dose limit.

For example, if the pulse rate is large, an X-ray dose that enters the subject is large and tends to reach the dose limit, compared to the case where the pulse rate is small. The X-ray diagnosis apparatus 1 of the present embodiment selects an added filter having a large thickness if the pulse rate is large, compared to the case where the pulse rate is small. For this reason, in the case where the dose limit can be easily reached, it is possible to suppress the amount of excess X-ray dose (exceeding the dose limit) entering the subject through the selecting of an added filter having a large X-ray reduction rate.

Furthermore, for example, if the pulse rate is small, the X-ray dose that enters the subject is small and the dose limit cannot be easily reached, compared to the case where the pulse rate is large. According to the X-ray diagnosis apparatus 1 of the present embodiment, if the pulse rate is small, an added filter having a small thickness is selected, compared to the case where the pulse rate is large. For this reason, in the case where the dose limit cannot be easily reached, it is possible to select an appropriate added filter in accordance with the ratio of the X-ray dose that enters the subject to the dose limit through selecting an added filter having a small X-ray reduction rate.

Eleventh Embodiment

Next, the eleventh embodiment will be described. The present embodiment is a modification of the configuration of the fifth embodiment as will be described below. Descriptions of the configurations, operations, and advantageous effects similar to those of the fifth embodiment will be omitted.

In an examination including multiple fluoroscopy imaging sessions, the processing circuitry 44 determines, through the imaging condition setting function 442, a size of a focal spot of X-rays in fluoroscopy imaging session to be performed next based on the output of the X-ray detector 13 in a fluoroscopy imaging session performed immediately prior. The processing circuitry 44 sets a focal-spot size of X-rays in accordance with the determined result. Herein, the focal-spot size may be a single value or have a range of values. If the focal-spot size is a single value, it can be determined and set as "small focal spot" or "medium focal spot". Alternatively, even in a case where the focal-spot size has a single value, when a control grid electrode is used, the focal-spot size may be determined and set as a value within the range of 0.2 to 0.7 mm, for example. On the other hand, in a case where the focal-spot size has a range of values, it may be determined as a value within the range of 0.2 to 0.4 mm, and set as a small focal spot. Alternatively, the focal-spot size can be determined as a value within the range of 0.5 to 0.7 mm, and set as a medium focal spot.

Specifically, the processing circuitry 44 determines, through the imaging condition setting function 442, a focal-spot size in a second fluoroscopy imaging session performed in accordance with an operation input to the input interface 43 after a first fluoroscopy imaging session, based on an output of the X-ray detector 13 in the first fluoroscopy imaging session performed in accordance with an operation input to the input interface 43, and determines a focal-spot size in a third fluoroscopy imaging session performed in accordance with an operation input to the input interface 43 after the second fluoroscopy imaging session, based on an output of the X-ray detector 13 in the second fluoroscopy imaging. To be more precise, in the first moving picture imaging and the second moving picture imaging, for example, the processing circuitry 44 sets at least one of the X-ray irradiation condition or a gain to be applied to an X-ray image in a following frame, based on an output of the X-ray detector 13 in a prior frame. Furthermore, the processing circuitry 44 determines a focal-spot size of X-rays in the second moving picture imaging based on an output of the X-ray detector 13 in the first moving picture imaging, through the conditions of X-ray irradiation in the first moving picture imaging. Similarly, the processing circuitry 44 determines a focal-spot size of X-rays in the third moving picture imaging based on an output of the X-ray detector 13 in the second moving picture imaging, through the conditions of X-ray irradiation in the second moving picture imaging.

The processing circuitry 44 may obtain the X-ray conditions in the first fluoroscopy imaging based on an X-ray image generated by the output of the X-ray detector 13 in the first fluoroscopy imaging, and determine a focal point size in the second fluoroscopy imaging based on the X-ray conditions in the first fluoroscopy imaging. The first fluoroscopy imaging is an example of the first moving picture imaging, the second fluoroscopy imaging is an example of the second moving picture imaging, and the third fluoroscopy imaging is an example of the third moving picture imaging.

The other configurations are the same as those of the fifth embodiment.

Figure 17:
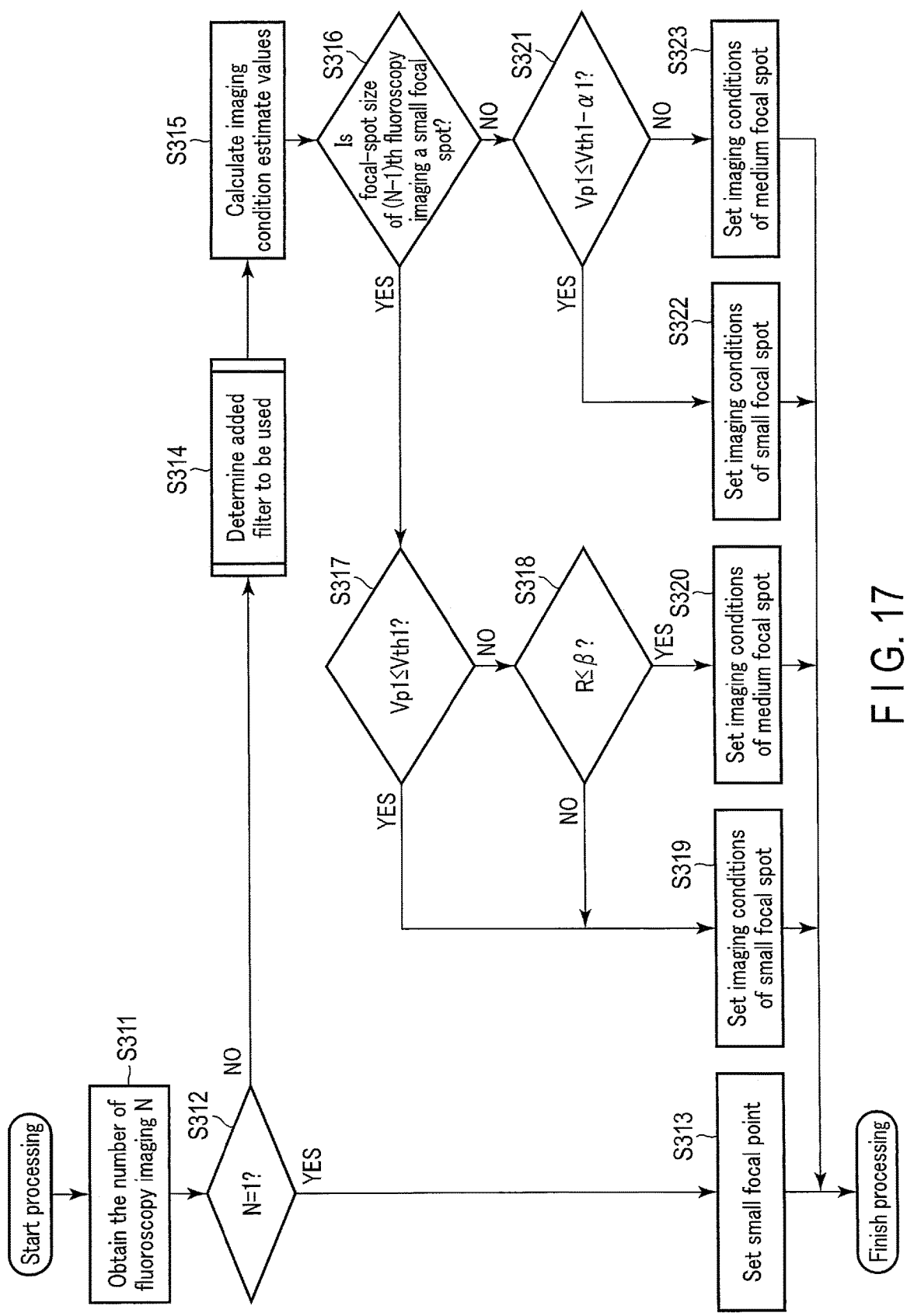
FIG. 17 is a flowchart illustrating a processing procedure of imaging condition setting processing performed by an X-ray diagnosis apparatus according to an eleventh embodiment.

In the following, the operation of the filter selecting processing which is performed by the X-ray diagnosis apparatus 1 will be described. FIG. 17 is a flowchart showing an example of the procedure of the imaging condition setting processing performed by the X-ray diagnosis apparatus 1 according to the present embodiment, and corresponds to the imaging condition setting processing in step S101 shown in FIG. 2. Since the processing in step S311 through step S312 and step S314 in FIG. 17 is the same as the processing in step S211 through step S212 and step S214 in the fifth embodiment, descriptions thereof are omitted.

(Imaging Condition Setting Processing)
(Step S313)

The processing circuitry 44 reads default imaging conditions for the fluoroscopy imaging which is performed for the first time since the commencement of the examination from the memory 41, and sets the default imaging conditions as imaging conditions for the fluoroscopy imaging to be performed next. At this time, the processing circuitry 44 sets a small focal-spot as a focal-spot size in the fluoroscopy imaging to be performed next.

(Step S315)

The processing circuitry 44 calculates imaging conditions when an X-ray detector entrance dose is approximated to a target dose to the greatest extent in the X-ray generator 12 (hereinafter, such conditions will be referred to as "imaging condition estimate values") for both a case where the fluoroscopy imaging is performed with a small focal spot and a case where the fluoroscopy imaging is performed with a medium focal spot in the N-th fluoroscopy imaging. The imaging condition estimate values are imaging conditions in the case where a condition regarding a short-time rating and a continuous rating of a tube is satisfied and an X-ray detector entrance dose is approximated to a target dose to the greatest extent possible. Specifically, for example, if the number of fluoroscopy imaging sessions N is 2, the processing circuitry 44 may calculate imaging condition estimate values in the second moving picture imaging based on a focal-spot size of X-rays, a tube voltage, a tube current, a pulse width, n AGC modification and filter specifying information obtained based on the output of the X-ray detector 13 in the first moving picture imaging. Herein, if the number of fluoroscopy imaging sessions N is 2, the first moving picture imaging and the second moving picture imaging correspond to the (N−1)th moving picture imaging and the N-th moving picture imaging, respectively. If the number of fluoroscopy imaging sessions N is 3, the processing circuitry 44 may calculate imaging condition estimate values in the third moving picture imaging based on a focal-spot size of X-rays, a tube voltage, a tube current, a pulse width, an AGC modification, and filter specifying information obtained based on the output of the X-ray detector 13 in the second moving picture imaging. Similarly, if the number of fluoroscopy imaging sessions N is 3, the second moving picture imaging and the third moving picture imaging correspond to the (N−1)th moving picture imaging and the N-th moving picture imaging, respectively.

The imaging condition estimate values include X-ray conditions when the X-ray detector entrance dose is approximated to the target dose to the greatest extent possible in the X-ray generator 12 (hereinafter, "X-ray condition estimate values"), and an AGC magnification which is predicted to be applied by the AGC when the X-ray detector entrance dose is approximated to the target dose to the greatest extent possible in the X-ray generator 12 (hereinafter, "AGC magnification estimate value"). The X-ray condition estimate values include: a tube voltage when an X-ray detector entrance dose is approximated to a target dose to the greatest extent possible in the X-ray generator 12 (hereinafter, "tube voltage estimate value"); a tube current when an X-ray detector entrance dose is approximated to a target dose to the greatest extent possible in the X-ray generator 12 (hereinafter, "tube current estimate value"); and a pulse width when an X-ray detector entrance dose is approximated to a target dose to the greatest extent possible in the X-ray generator 12 (hereinafter, "pulse width estimate value"). The X-ray condition estimate values may be values that include at least one of the following: a tube voltage estimate value that satisfies a condition regarding an X-ray tube output necessary for securing image quality of an X-ray image (hereinafter, "target output"); a tube current estimate value that satisfies the condition; a pulse width estimate value that satisfies the condition regarding the target output; or an AGC modification estimate value that satisfies the condition regarding the target output.

As the processing of calculating the imaging condition estimate values, for example, processing based on the following expression, wherein the X-ray condition of a current fluoroscopy imaging session is {xV, mA, msec, AGC}, and the function h of a prior or current condition is (Focus, BF, $BF_{immediately\ prior}$, $kV_{immediately\ prior}$, $msec_{immediately\ prior}$, $AGC_{immediately\ prior}$) is performed:

$$X\{xV, mA, msec, AGC\} = h(Focus, BF, BF_{immediately\ prior}, kV_{immediately\ prior}, msec_{immediately\ prior}, AGC_{immediately\ prior})$$

In the above expression, kV is a tube voltage, mA is a tube current, msec is a pulse width, AGC is an AGC magnification, Focus is a focal-spot size, BF is filter specifying information, the subscript "immediately prior" means a condition in an immediately prior fluoroscopy imaging session, and no subscript means a condition in a current fluoroscopy imaging session.

In the processing for calculating the imaging condition estimate values, the processing circuitry 44 obtains imaging conditions in the (N−1)th fluoroscopy imaging. The processing circuitry 44 reads and obtains the imaging conditions in the (N−1)th fluoroscopy imaging stored in the memory 41. The processing circuitry 44 obtains the imaging conditions for the (N−1)th fluoroscopy imaging so as to obtain imaging conditions in an immediately prior fluoroscopy imaging session among all the fluoroscopy imaging sessions performed since the commencement of the examination. The processing circuitry 44 obtains, for example, a focal-spot size, filter specifying information, a tube voltage, a tube current, a pulse width, and an AGC magnification, as imaging conditions in the (N−1)th fluoroscopy imaging. As described above, during the fluoroscopy imaging, feedback control is performed to change the X-ray conditions, etc. based on the change in the subject conditions, and when the fluoroscopy imaging is finished, at least one of the tube voltage, the tube current, the pulse width, or the AGC magnification is in an appropriately controlled state according to the change in the subject conditions. Accordingly, through obtaining the imaging conditions in the immediately prior fluoroscopy imaging session, it is possible to obtain the imaging conditions appropriately controlled in accordance with the change in the subject conditions. Through computation based on an X-ray image generated in an immediately prior fluoroscopy imaging session, the imaging conditions further appropriately controlled may be calculated in accordance with the change in the subject conditions, and the calculated imaging conditions may be obtained as imaging conditions in the immediately prior fluoroscopy imaging session.

Next, the processing circuitry 44 calculates a target output based on the focal-spot size, the filter specifying information, the tube voltage, the tube current, the pulse width, and the AGC magnification in the (N−1)th fluoroscopy imaging. The processing circuitry 44 calculates the following based on the target output and the filter specifying information in the N-th fluoroscopy imaging: a tube voltage estimate value Vp1, a tube current estimate value Ip1, a pulse width estimate value Wp1, and an AGC magnification estimate value Mp1 in the case where the fluoroscopy imaging is performed with a small focal spot; and a tube voltage estimate value Vp2, a tube current estimate value Ip2, a pulse width estimate value Wp2, and an AGC magnification estimate value Mp2 in the case where the fluoroscopy imaging is performed with a medium focal spot. If the immediately prior focal-spot size is the same as one of the small focal spot or the medium focal spot, imaging condition estimate values indicating approximately the same imaging conditions as those in the immediately prior fluoroscopy imaging are calculated. To be more precise, for example, if the number of fluoroscopy imaging sessions N is 2, the processing circuitry 44 calculates the imaging condition estimate values in the second moving picture imaging for each of the plurality of focal-spot sizes having different focal-spot sizes of X-rays, and determines the imaging condition estimate values corresponding to the focal-spot size determined as a focal-spot size of X-rays as imaging conditions in the second moving picture imaging. Similarly, for example, if the number of fluoroscopy imaging sessions N is 3, the processing circuitry 44 calculates the imaging condition estimate values in the third moving picture imaging for each of the plurality of focal-spot sizes having different focal-spot sizes of X-rays, and determines the imaging condition estimate values corresponding to the focal-spot size determined as a size of the focal-spot sizes of X-rays as imaging conditions in the third moving picture imaging.

(Step S316)

The processing circuitry 44 determines whether or not the focal-spot size of the (N−1)th fluoroscopy imaging is a small focal spot based on the imaging conditions in the (N−1)th fluoroscopy imaging obtained in step S315. If the focal-point size of the (N−1)th fluoroscopy imaging a small focal spot (Yes in step S316), the processing proceeds to step S317. If the focal-spot size in the (N−1)th fluoroscopy imaging is not a small focal spot (No in step S316), the processing circuitry 44 determines that the focal-spot size is a medium focal spot, and the processing proceeds to step S321.

(Step S317)

The processing circuitry 44 determines whether or not the tube voltage estimate value Vp1 is equal to or smaller than a threshold Vth1. The threshold Vth1 is a value for determining whether or not the contrast of an X-ray image to be generated satisfies a predetermined condition. The threshold Vth1 is a value determined based on the range of, for example, 20 to 150 kV. The threshold Vth1 may be set at a predetermined value, and may be input by an operator for each examination. The threshold Vth1 is an example of a determination value. The threshold Vth1 is also an example of a first value. If the tube voltage estimate value Vp1 is equal to or smaller than the threshold Vth1 (Yes in step S317), the processing proceeds to step S318. If the tube voltage estimate value Vp1 is not equal to or smaller than the threshold Vth1 (No in step S317), in other words, the tube voltage estimate value Vp1 is greater than the threshold Vth1, the processing proceeds to step S319.

(Step S318)

The processing circuitry 44 determines whether or not a dose limit attainment index R is equal to or smaller than a threshold β. Herein, the dose limit attainment index R (=G/L×100 [%]) is a ratio of an exposure dose estimate value G to a dose limit L. The dose limit L is an upper limit value regarding a dose of X-rays that enters a subject per unit time (an entrance dose rate). In other words, the dose limit L is an upper limit value of an exposure dose. The dose limit L is predetermined by a country in which the apparatus is used, for example. The dose limit L is 50 mGr/min or 87 mGr/min, for example. The exposure dose estimate value G is a dose of X-rays predicted to enter the subject when the Nth fluoroscopy imaging is performed on the imaging condition, and is the imaging condition estimate value for the case of fluoroscopy imaging performed with the medium focal spot. The threshold β is a value for determining whether or not the exposure dose estimate value G is sufficiently small with respect to the dose limit L. The threshold β is an example of a dose determination value. The threshold β is a value determined based on the range of, for example, 90 to 99%. The threshold β may be set at a predetermined value, or input by an operator for each fluoroscopy imaging session.

In the processing in step S318, the processing circuitry 44 first calculates the exposure dose estimate value G, based on a tube voltage estimate value Vp2, a tube current estimate value Ip2, a pulse width estimate value Wp2, an AGC magnification estimate value Mp2, and filter specifying information in the N-th fluoroscopy imaging. Then, the dose limit attainment index R is calculated based on the exposure dose estimate value G and the dose limit L. If the dose limit attainment index R is equal to or smaller than the threshold β (Yes in step S318), the processing circuitry 44 determines whether or not the entrance dose rate is sufficiently small with respect to the dose limit L when the N-th fluoroscopy imaging is performed on the imaging condition as the imaging condition estimate value corresponding to the medium focal spot, and the processing proceeds to step S320. If the dose limit attainment index R is larger than the threshold β (No in step S318), the processing circuitry 44 determines whether or not the entrance dose rate is sufficiently small with respect to the dose limit L when the N-th fluoroscopy imaging is performed on the imaging condition as the imaging condition estimate value corresponding to the medium focal spot, and the processing proceeds to step S319.

(Step S319)

The processing circuitry 44 sets the focal-spot size in the N-th fluoroscopy imaging to a small focal spot. The processing circuitry 44 sets the imaging condition estimate value corresponding to the small focal spot as an imaging condition in the N-th fluoroscopy imaging. At this time, the processing circuitry 44 sets: the tube voltage estimate value Vp1 as a tube voltage in the N-th fluoroscopy imaging; the tube current estimate value Ip1 as a tube current in the N-th fluoroscopy imaging; the pulse width estimate value Wp1 as a pulse width in the N-th fluoroscopy imaging; and the AGC magnification estimate value Mp1 as an AGC magnification in the N-th fluoroscopy imaging. Then, the processing circuitry 44 finishes the imaging condition setting processing, and the processing proceeds to step S103.

(Step S320)

The processing circuitry 44 sets the focal-spot size in the N-th fluoroscopy imaging to a medium focal spot. The processing circuitry 44 sets the imaging condition estimate value corresponding to the medium focal spot as an imaging condition in the N-th fluoroscopy imaging. At this time, the processing circuitry 44 sets: the tube voltage estimate value Vp2 as a tube voltage in the N-th fluoroscopy imaging; the tube current estimate value Ip2 as a tube current in the N-th fluoroscopy imaging; the pulse width estimate value Wp2 as a pulse width in the N-th fluoroscopy imaging; and the AGC magnification estimate value Mp2 as an AGC magnification in the N-th fluoroscopy imaging. Then, the processing circuitry 44 finishes the imaging condition setting processing, and the processing proceeds to step S103.

(Step S321)

The processing circuitry 44 determines whether or not the tube voltage estimate value Vp1 is equal to or smaller than the threshold Vth2. The threshold Vth2 is smaller than the threshold Vth1 by the set value α1. In other words, Vth2=Vth1−α1. The set value α1 is a value representing room in a tube voltage to determine whether or not the medium focal spot should be switched to the small focal spot, and is a value determined within the range from 1 to 10 kV, for example. The set value α1 may be set at a predetermined value, and may be input by an operator for each examination. The threshold Vth2 is an example of a determination value. The threshold Vth2 is also an example of a second value. If the tube voltage estimate value Vp1 is equal to or smaller than the threshold Vth2 (Yes in step S321), the processing proceeds to step S322. If the tube voltage estimate value Vp1 is not equal to or smaller than the threshold Vth2 (No in step S321), in other words, if the tube voltage estimate value Vp1 is greater than the threshold Vth2, the processing proceeds to step S323.

(Step S322)

The processing in step S322 is similar to that in step S319. In other words, the processing circuitry 44 sets the focal-spot size in the N-th fluoroscopy imaging to a small focal spot. Then, the processing circuitry 44 finishes the imaging condition setting processing, and the processing proceeds to step S103.

(Step S323)

The processing in step S323 is similar to that in step S320. In other words, the processing circuitry 44 sets the focal-spot size in the N-th fluoroscopy imaging to a medium focal spot. Then, the processing circuitry 44 finishes the imaging condition setting processing, and the processing proceeds to step S103.

When the imaging condition setting processing is finished, the processing circuitry 44 performs the N-th fluoroscopy imaging based on the imaging conditions set in the imaging condition setting processing. Then, when the N-th fluoroscopy imaging is finished, in the case of performing the next fluoroscopy imaging, the processing circuitry 44 performs the imaging condition setting processing in step S101 once again. At this time, the processing circuitry 44 determines the imaging conditions including a focal-spot size in the (N+1)th fluoroscopy imaging, based on the X-ray conditions in the N-th fluoroscopy imaging, similarly to the imaging condition setting processing in the N-th fluoroscopy imaging.

In the following description, advantageous effects of the X-ray diagnosis apparatus 1 according to the present embodiment will be described.

The X-ray diagnosis apparatus 1 in the present embodiment determines the size of a focal spot of X-rays in second moving picture imaging, which is performed in accordance with an operation input at an operating unit after first moving picture imaging, based on an output of the X-ray detector 13 in the first moving picture imaging performed in accordance with an operation input to the operating unit. Furthermore, the X-ray diagnosis apparatus 1 in the present embodiment determines the size of a focal spot of X-rays in third moving picture imaging, which is performed in accordance with an operation input at the operating unit after second moving picture imaging, based on an output of the X-ray detector 13 in the second moving picture imaging.

In summary, the X-ray diagnosis apparatus 1 in the present embodiment determines a focal-spot size in fluoroscopy imaging performed next in accordance with an operation input to the input interface 43, based on an output of the X-ray detector 13 in fluoroscopy imaging performed immediately prior in accordance with an operation input to the input interface 43.

For example, the X-ray diagnosis apparatus 1 of the present embodiment determines a focal-spot size in N-th fluoroscopy imaging, which is performed in accordance with an operation input to the input interface 43 after (N−1)th fluoroscopy imaging, based on X-ray conditions in the (N−1)th fluoroscopy imaging performed in accordance with an operation input to the input interface 43, and determines a focal-spot size in (N+1)th fluoroscopy imaging, which is performed in accordance with an operation input to the input interface 43 after the N-th fluoroscopy imaging, based on the X-ray conditions in the N-th fluoroscopy imaging performed in accordance with an operation input to the input interface 43.

The X-ray diagnosis apparatus 1 of the present embodiment determines a focal-spot size of X-rays at the time when second moving picture imaging is commenced based on an output of the X-ray detector 13 at the time when first moving picture imaging is finished, and determines a focal-spot size of X-rays at the time when third moving picture imaging is commenced based on an output of the X-ray detector 13 at the time when the second moving picture imaging is finished.

For example, the X-ray diagnosis apparatus 1 of the present embodiment determines a focal-spot size of X-rays at the time when N-th fluoroscopy imaging is commenced based on the X-ray conditions at the time when (N−1)th fluoroscopy imaging is finished, and determines a focal-spot size of X-rays at the time when (N+1)th fluoroscopy imaging is commenced based on the X-ray conditions at the time when the N-th fluoroscopy imaging is finished.

The X-ray diagnosis apparatus 1 of the present embodiment calculates, based on an output of the X-ray detector 13 in first moving picture imaging, an imaging condition estimate value that satisfies a condition regarding a target output in the case where a particular focal-spot size of X-rays is used in second moving picture imaging, and determines a focal-spot size of X-rays in the second moving picture imaging based on the imaging condition estimate value in the second moving picture imaging. Furthermore, the X-ray diagnosis apparatus 1 of the present embodiment calculates, based on an output of the X-ray detector 13 in second moving picture imaging, an imaging condition estimate value for third moving picture imaging, and determines a focal-spot size of X-rays in the third moving picture imaging based on the imaging condition estimate value in the third moving picture imaging.

For example, the X-ray diagnosis apparatus 1 of the present embodiment calculates a tube voltage estimate value Vp1 in N-th fluoroscopy imaging based on X-ray conditions in (N−1)th fluoroscopy imaging, determines a focal-spot size in the N-th fluoroscopy imaging based on the tube voltage estimate value Vp1, calculates a tube voltage estimate value Vp1 in (N+1)th fluoroscopy imaging based on the X-ray conditions in the N-th fluoroscopy imaging, and determines a focal-spot size in the (N+1)th fluoroscopy imaging based on the tube voltage estimate value Vp1.

In other words, according to the X-ray diagnosis apparatus 1 of the present embodiment, with the above-described configurations and operations, it is possible to determine a focal-spot size in next fluoroscopy imaging, which is performed through stepping a foot switch once again, based on an output of the X-ray detector 13 in fluoroscopy imaging performed immediately prior. For this reason, in next fluoroscopy imaging, it is possible to set a focal-spot size in accordance with X-ray conditions of the fluoroscopy imaging performed immediately prior. Thus, even when a focal-spot size appropriate for generating an X-ray image in which its contrast satisfies a predetermined condition has been changed due to a change in a body thickness of the subject during immediately prior fluoroscopy imaging, it is still possible to automatically set an appropriate focal-spot size in next fluoroscopy imaging based on X-ray conditions controlled at appropriate values in accordance with the body thickness of the subject through the feedback control. It is thereby possible to improve image quality of an X-ray image generated in next fluoroscopy imaging. For example, if the body thickness of the subject is small and there is room in a tube bulb output, a focal-spot size can be set to a small focal spot, and a sharp image can be thereby generated. In contrast, when the body thickness of the subject is small and the tube voltage becomes high at the small focal point, it is possible to generate an image having a high contrast or an image having less noise through the switching of the focal-spot size to a medium focal spot that provides a higher output.

The X-ray diagnosis apparatus 1 of the present embodiment determines a first focal-spot size as a focal-spot size of X-rays in second moving picture imaging when an imaging condition estimate value in the second moving picture imaging is equal to or smaller than a determination value, and determines a second focal-spot size, larger than the first focal-spot size, as a focal-spot size of X-rays in the second moving picture imaging when the imaging condition estimate value in the second moving picture imaging is greater than the determination value. Furthermore, the X-ray diagnosis apparatus 1 of the present embodiment sets a first focal-spot size as a focal-spot size of X-rays in third moving picture imaging when the imaging condition estimate value in the third moving picture imaging is equal to or smaller than the determination value, and determines a second focal-spot size as a focal-spot size of X-rays in the third moving picture imaging when the imaging condition estimate value in the third moving picture imaging is greater than the determination value.

In summary, for example, in the processing of step S321, the X-ray diagnosis apparatus 1 of the present embodiment determines, if the tube voltage estimate value $Vp1$ in N-th fluoroscopy imaging is equal to or smaller than the threshold $Vth2$, a focal-spot size in the N-th fluoroscopy imaging to a small focal spot, and also determines, if the tube voltage estimate value $Vp1$ in the N-th fluoroscopy imaging is greater than the threshold $Vth2$, a focal-spot size in the N-th fluoroscopy imaging to a medium focal spot.

For example, if the body thickness of the subject becomes smaller during immediately prior fluoroscopy imaging using a medium focal spot, an X-ray tube output necessary for generating an X-ray image having brightness of a predetermined level or higher becomes smaller. In this case, according to the X-ray diagnosis apparatus 1 of the present embodiment, the tube voltage estimate value $Vp1$ in the case of a small focal spot becomes equal to or smaller than the threshold $Vth2$, and the focal-spot size in the next fluoroscopy imaging is set to a small focal spot. Thus, if there is room in the X-ray tube output, in other words, if an X-ray image having a predetermined contrast or higher can be generated using a small focal spot, which provides only a small output, it is possible to generate an X-ray image having a higher resolution compared to a case where a focal-spot size is set to a medium focal spot, through setting a focal-spot size to a small focal spot in next fluoroscopy imaging.

As another example, if the body thickness of the subject becomes larger during immediately prior fluoroscopy imaging using a small focal spot, an X-ray tube output necessary for generating an X-ray image having brightness of a predetermined level or higher becomes greater, thereby reducing a contrast of the X-ray image to be generated. In this case, according to the X-ray diagnosis apparatus 1 of the present embodiment, the tube voltage estimate value $Vp1$ in the small focal spot becomes greater than the threshold $Vth2$, and the focal-spot size in the next fluoroscopy imaging is set to a medium focal spot. For this reason, through switching the focal-spot size to a medium focal spot, which can increase the X-ray tube output compared to a small focal spot, it is possible to secure a necessary dose and control the tube voltage in next fluoroscopy imaging. Accordingly, compared to the case where a small focal-spot size is continuously used, it is possible to generate an X-ray image with more secured contrast and less noise.

The X-ray diagnosis apparatus 1 of the present embodiment determines a focal-spot size of X-rays in second moving picture imaging using a first value as a determination value when a focal-spot size of X-rays in first moving picture imaging is a first focal-spot size, and determines a focal-spot size of X-rays in second moving picture imaging using a second value, which is different from the first value, as a determination value when a focal-spot size of X-rays in first moving picture imaging is a second focal-spot size. If the focal-spot size of X-rays in the second moving picture imaging is the first focal-spot size, a focal-spot size of X-rays in third moving picture imaging is determined using the first value as a determination value, and if the focal-spot size of X-rays in the second moving picture imaging is the second focal-spot size, a focal-spot size of X-rays in third moving picture imaging is determined using the second value as a determination value. For example, the second value is smaller than the first value.

In summary, the X-ray diagnosis apparatus 1 of the present embodiment determines, if a focal-spot size in (N−1)th fluoroscopy imaging is a small focal spot for example, a focal-spot size in N-th fluoroscopy imaging based on the tube voltage estimate value $Vp1$ and the threshold $Vth1$ in the N-th fluoroscopy imaging, and determines, if a focal-spot size in the (N−1)th fluoroscopy imaging is a medium focal spot for example, a focal-spot size in the N-th fluoroscopy imaging based on the tube voltage estimate value $Vp1$ and the threshold $Vth2$ in the N-th fluoroscopy imaging. Herein, the threshold $Vth2$ is smaller than the threshold $Vth1$.

In other words, according to the X-ray diagnosis apparatus 1 of the present embodiment, with the above-described configurations and operations, a threshold for determining whether or not a focal-spot size in next fluoroscopy imaging should be switched from a medium focal spot to a small focal spot differs from a threshold for switching the focal-spot size from a small focal spot to a medium focal spot. For this reason, it is possible to prevent occurrence of focal-spot size switching every time fluoroscopy imaging is performed, even when, for example, the tube voltage estimate value $Vp1$ is switched between a range smaller than the threshold $Vth$ and a range larger than the threshold $Vth$ every time a current fluoroscopy imaging session is switched to a next one.

The X-ray diagnosis apparatus 1 of the present embodiment further calculates a ratio of an exposure dose estimate value to an upper limit value of an exposure dose when an imaging condition estimate value in second moving picture imaging is used as an imaging condition in the second moving picture imaging, and a ratio of an exposure dose estimate value to an upper limit value of an exposure dose when an imaging condition estimate value in third moving picture imaging is used as an imaging condition in the third moving picture imaging. Furthermore, if a focal-spot size of X-rays in first moving picture imaging is a first focal-spot size and the imaging condition estimate value in the second moving picture imaging is larger than a determination value, and the ratio in the second moving picture imaging is larger than a dose determination value, the first focal-spot size is determined as a focal-spot size of X-rays in the second moving picture imaging. If a focal-spot size of X-rays in the second moving picture imaging is the first focal-spot size and the imaging condition estimate value in the third moving picture imaging is larger than the determination value, and the ratio in the third moving picture imaging is larger than a dose determination value, the first focal-spot size is determined as a focal-spot size of X-rays in the third moving picture imaging.

In summary, the X-ray diagnosis apparatus 1 of the present embodiment determines a focal-spot size in N-th fluoroscopy imaging to a medium focal spot if, for example, a focal-spot size in (N−1)th fluoroscopy imaging is a small focal spot and the tube voltage estimate value Vp1 in the N-th fluoroscopy imaging is greater than the threshold Vth1, and the exposure limit attainment index R is equal to or smaller than the threshold β, and determines the focal-spot size in the (N−1)th fluoroscopy imaging to a small focal spot if the focal-spot size in the (N−1)th fluoroscopy imaging is a small focal spot and the tube voltage estimate value Vp1 in the N-th fluoroscopy imaging is greater than the threshold Vth1, and the exposure limit attainment index R is greater than the threshold β.

Accordingly, if a small focal spot is used in immediately prior fluoroscopy imaging, the X-ray diagnosis apparatus 1 of the present embodiment switches the next focal-spot size to a medium focal spot only when a contrast of an X-ray image generated in next fluoroscopy imaging becomes lower, and a predicted exposure dose is sufficiently small with respect to a dose limit in the case where the medium focal spot is used as the focal-spot size. In contrast, even when a contrast of an X-ray image to be generated in next fluoroscopy imaging becomes lower in the X-ray diagnosis apparatus 1 of the present embodiment, the next focal-spot size is not switched to a medium focal spot unless the predicted exposure dose is sufficiently small with respect to the dose limit.

In other words, according to the X-ray diagnosis apparatus 1 of the present embodiment, with the foregoing configurations and operations, a focal-spot size is switched to a medium focal spot that increases an exposure dose to the subject, only when room in an exposure dose can be secured at a certain extent. It is thereby possible to prevent an excess of the exposure dose to the subject over the dose limit in next fluoroscopy imaging.

The X-ray diagnosis apparatus 1 of the present embodiment determines a focal-spot size of X-rays in second moving picture imaging performed in accordance with an operation input to the operating unit after first moving picture imaging, based on an output of the X-ray detector 13 in the first moving picture imaging performed in accordance with an operation input to the operating unit and information regarding a filter selected by the filter selecting unit, and determines a focal-spot size of X-rays in the third moving picture imaging performed in accordance with an operation input to the operating unit after the second moving picture imaging, based on an output of the X-ray detector 13 in the second moving picture imaging and information regarding a filter selected by the filter selecting unit.

In summary, the X-ray diagnosis apparatus 1 of the present embodiment selects an appropriate added filter to be used in next fluoroscopy imaging in consideration of an FPD element size in addition to a body thickness, along with a consideration of the change in a target dose. Then, the X-ray diagnosis apparatus 1 of the present embodiment determines an appropriate focal-spot size in the next fluoroscopy imaging based on imaging condition estimate values in the case where the appropriately selected added filter is used in the next fluoroscopy imaging.

In other words, according to the X-ray diagnosis apparatus 1 of the present embodiment, with the above-described configurations and operations, an appropriate focal-spot size in next fluoroscopy imaging can be set based on X-ray conditions controlled at appropriate values in fluoroscopy imaging performed immediately prior in accordance with the body thickness of the subject through the feedback control, and an added filter selected appropriately in consideration of the change in the target dose. Image quality of an X-ray image generated in next fluoroscopy imaging is thus further improved.

According to at least one of the foregoing embodiments, it is possible to provide an X-ray diagnosis apparatus that can determine an appropriate added filter in accordance with a target dose.

Modifications of Fifth to Eleventh Embodiments

The processing circuitry 44 may select, through the filter selecting function 447, a plurality of additional filters from filters A through D, as an added filter used in N-th fluoroscopy imaging. The processing circuitry 44 may determine that, through the filter selecting function 447, none of filters A through D is not used as a result of selecting an added filter to be used in N-th fluoroscopy imaging.

The number of additional filters provided in the X-ray generator 12 may be one. In this case, an added filter having a different thickness according to a part thereof to be inserted between the X-ray tube and the X-ray diaphragm, and in the filter selecting processing, a correspondence table showing a relationship of a maximum power, a dose limit, an SID, and a body thickness with respect to the thickness of the added filter is used. The processing circuitry 44 determines, through the filter selecting function 447, the thickness of the added filter in the part to be inserted between the X-ray tube and the X-ray diaphragm, based on the correspondence table and the maximum power, the dose limit, the SID, and the body thickness in N-th fluoroscopy imaging. Furthermore, the processing circuitry 44 adjusts, through the drive controlling function 443, the part of the added filter to be inserted between the X-ray tube and the X-ray diaphragm, based on the determined thickness of the added filter. In this case, the processing circuitry 44 that enables the filter selecting function 447 is an example of a thickness determining unit.

A plurality of configurations in the fifth through tenth embodiments may be combined. For example, The processing circuitry 44 may select, through the filter selecting function 447, an added filter to be inserted into a path from the focal spot of the X-ray tube to the X-ray detector 13 from a plurality of additional filters, based on the FPD element size, the focal-spot size, the maximum power, the dose limit, and the body thickness in the N-th fluoroscopy imaging, and may select an added filter to be inserted into the path from the focal spot of the X-ray tube to the X-ray detector 13 from the plurality of additional filters, based on the FPD element size, the FPD pixel size, the pixel size, the focal-spot size, the pulse rate, the maximum power, the dose limit, and the body thickness in the N-th fluoroscopy imaging. Furthermore, for example, the processing circuitry 44 may select, by the filter selecting function 447, an added filter to be inserted into the path from a focal spot of the X-ray tube to the X-ray detector 13 from a plurality of additional filters, based on at least one of an FPD pixel size, a pixel size, a field-of-view size, a focal-spot size, a maximum power, or a dose limit in N-th fluoroscopy imaging, and a body thickness.

For the filter selecting processing, the processing circuitry 44 may use as information regarding the body thickness of the subject, instead of the body thickness, X-ray conditions controlled as appropriate in accordance with the change in subject conditions by the above-described feedback control in the (N−1)th fluoroscopy imaging. The X-ray conditions controlled as appropriate in the (N−1)th fluoroscopy imaging in accordance with subject conditions by the above-described feedback condition are, for example, filter-specifying information, a tube voltage, a tube current, a pulse width, and an AGC magnification, etc. at the time when the (N−1)th fluoroscopy imaging is finished.

According to at least one of the fifth through eleventh embodiments, it is possible to determine an appropriate added filter in accordance with a target dose.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnosis apparatus comprising:
an X-ray tube that generates X-rays;
an X-ray detector that detects X-rays generated by the X-ray tube;
an operating unit that instructs performance of moving picture imaging using the X-ray tube and the X-ray detector; and
processing circuitry configured to determine a condition of X-ray irradiation by the X-ray tube, wherein
the processing circuitry is configured to:
  determine a focal-spot size of X-rays in second moving picture imaging performed in accordance with an operation input to the operating unit after first moving picture imaging, based on an output of the X-ray detector in the first moving picture imaging performed in accordance with an operation input to the operating unit; and
  determine a focal-spot size of X-rays in third moving picture imaging performed in accordance with an operation input to the operating unit after the second moving picture imaging, based on an output of the X-ray detector in the second moving picture imaging.

2. The X-ray diagnosis apparatus according to claim 1, wherein
the processing circuitry changes the focal-spot size of X-rays in accordance with a relationship between a parameter based on an output of the X-ray detector and a threshold, and
the threshold used when the focal-spot size of X-rays is changed from a first size to a second size larger than the first size differs from the threshold used when the focal-spot size of X-rays is changed from the second size to the first size.

3. The X-ray diagnosis apparatus according to claim 2, wherein
an X-ray dose corresponding to the threshold used when the focal-spot size of X-rays is changed from the first size to the second size is larger than a X-ray dose corresponding to the threshold used when the focal-spot size of X-rays is changed from the second size to the first size.

4. The X-ray diagnosis apparatus according to claim 1, wherein
the processing circuitry is configured to:
  determine a focal-spot size at the time when the second moving picture imaging is commenced based on an output of the X-ray detector at the time when the first moving picture imaging is concluded; and
  determine a focal-spot size at the time when the third moving picture imaging is commenced based on an output of the X-ray detector at the time when the second moving picture imaging is concluded.

5. The X-ray diagnosis apparatus according to claim 1, wherein
the processing circuitry is configured to:
  calculate, for the second moving picture imaging, imaging condition estimate value that satisfy a condition regarding a target output in a case where a specific focal-spot size of X-rays is used, based on an output of the X-ray detector in the first moving picture imaging, and determine the focal-spot size of X-rays in the second moving picture imaging based on the imaging condition estimate value in the second moving picture imaging; and
  calculate the imaging condition estimate value for the third moving picture imaging based on an output of the X-ray detector in the second moving picture imaging, and determine the focal-spot size of X-rays in the third moving picture imaging based on the imaging condition estimate value in the third moving picture imaging.

6. The X-ray diagnosis apparatus according to claim 5, wherein
the processing circuitry is configured to:
  if the imaging condition estimate value in the second moving picture imaging are equal to or smaller than determination values, determine a first focal-spot size as the focal-spot size of X-rays in the second moving picture imaging; and if the imaging condition estimate value in the second moving picture imaging are greater than the determination values, determine a second focal-spot size larger than the first focal-spot size as the focal-spot size of X-rays in the second moving picture imaging,
  if the imaging condition estimate value in the third moving picture imaging are equal to or smaller than a determination value, determine the first focal-spot size as the focal-spot size of X-rays in the third moving picture imaging; and if the imaging condition estimate value in the third moving picture imaging are greater than the determination values, determine the second focal-spot size larger than the third focal-spot size as the focal-spot size of X-rays in the second moving picture imaging.

7. The X-ray diagnosis apparatus according to claim 6, wherein
the processing circuitry is configured to:
  if a focal-spot size of X-rays in the first moving picture imaging is the first focal-spot size, determine the focal-spot size of X-rays in the second moving picture imaging using a first value as the determination value; and if a focal-spot size of X-rays in the first moving picture imaging is the second focal-spot size, determine the focal-spot size of X-rays in the second moving picture imaging using a second value, which is different from the first value, as the determination value, if a focal-spot size of X-rays in the second moving picture imaging is the first focal-spot size, determine the focal-spot size of X-rays in the third moving picture imaging using the first value as the determination value; and if a focal-spot size of X-rays in the second moving picture imaging is the second focal-spot size, determine the focal-spot size of X-rays in the second moving picture imaging using the second value as the determination value.

8. The X-ray diagnosis apparatus according to claim 7, wherein
the second value is smaller than the first value.

9. The X-ray diagnosis apparatus according to claim 6, wherein
the processing circuitry is configured to:
further calculate a ratio of an exposure dose estimate value to an upper limit value of an exposure dose in a case where the imaging condition estimate value in the second moving picture imaging are used as imaging conditions in the second moving picture imaging, and a ratio of an exposure dose estimate value to an upper limit value of an exposure dose in a case where the imaging condition estimate value in the third moving picture imaging are used as imaging conditions in the third moving picture imaging,
if a focal-spot size of X-rays in the first moving picture imaging is the first focal-spot size and the imaging condition estimate value in the second moving picture imaging are larger than the determination values, and, furthermore, the ratio in the second moving picture imaging is larger than a dose determination value, the second focal-spot size is determined as a focal-spot size of X-rays in the second moving picture imaging,
if a focal-spot size of X-rays in the second moving picture imaging is the first focal-spot size and the imaging condition estimate value in the third moving picture imaging are larger than the determination values, and, furthermore, the ratio in the third moving picture imaging is larger than a dose determination value, the second focal-spot size is determined as a focal-spot size of X-rays in the third moving picture imaging.

10. The X-ray diagnosis apparatus according to claim 5, wherein
the imaging condition estimate value includes at least one of a tube voltage estimate value that satisfies the condition regarding the target output, a tube current estimate value that satisfies the condition regarding the target output, a pulse width estimate value that satisfies the condition regarding the target output, or an AGC magnification estimate value that satisfies the condition regarding the target output.

11. The X-ray diagnosis apparatus according to claim 5, wherein
the processing circuitry is configured to:
calculate the imaging condition estimate value in the second moving picture imaging based on a focal-spot size of X-rays, a tube voltage, a tube current, a pulse width, an AGC magnification, and filter specifying information obtained based on an output of the X-ray detector in the first moving picture imaging,
calculate the imaging condition estimate value in the third moving picture imaging based on a focal-spot size of X-rays, a tube voltage, a tube current, a pulse width, an AGC magnification, and filter specifying information obtained based on an output of the X-ray detector in the second moving picture imaging.

12. The X-ray diagnosis apparatus according to claim 5, wherein
the processing circuitry is configured to:
calculate the imaging condition estimate value in the second moving picture imaging for each of a plurality of focal-spot sizes of X-rays, and determine, as imaging conditions in the second moving picture imaging, the imaging condition estimate value corresponding to the focal-spot size determined as the focal-spot size of X-rays;
calculate the imaging condition estimate value in the third moving picture imaging for each of a plurality of focal-spot sizes of X-rays, and determine, as imaging conditions in the third moving picture imaging, the imaging condition estimate value corresponding to the focal-spot size determined as the focal-spot size of X-rays.

13. The X-ray diagnosis apparatus according to claim 1, wherein
the processing circuitry is configured to select a filament to be used from a plurality of filaments provided in a tube bulb of the X-ray tube based on the determined focal-spot size of X-rays.

14. The X-ray diagnosis apparatus according to claim 1, further comprising:
a control grid electrode capable of adjusting the focal-spot size of X-rays generated from the X-ray tube, wherein
the processing circuitry is configured to control the control grid electrode based on the determined focal-spot size of X-rays.

15. The X-ray diagnosis apparatus according to claim 1, wherein
the processing circuitry is configured to:
control at least one of the X-ray irradiation condition or a gain to be applied to an X-ray image in a following frame based on an output of the X-ray detector in a prior frame
determine a focal-spot size of X-rays in the second moving picture imaging based on an output of the X-ray detector in the first moving picture imaging, through X-ray irradiation conditions in the first moving picture imaging
determine a focal-spot size of X-rays in the third moving picture imaging based on an output of the X-ray detector in the second moving picture imaging, under X-ray irradiation conditions in the second moving picture imaging.

16. The X-ray diagnosis apparatus according to claim 1, wherein
the processing circuitry is configured to:
determine the focal-spot size of X-rays in the second moving picture imaging according to an X-ray image generated based on an output of the X-ray detector in the first moving picture imaging, and
determine the focal-spot size of X-rays in the third moving picture imaging according to an X-ray image generated based on an output of the X-ray detector in the second moving picture imaging.

17. The X-ray diagnosis apparatus according to claim 1, wherein
the processing circuitry is configured to:
determine the focal-spot size of X-rays in the second moving picture imaging upon conclusion of the first moving picture imaging; and determine the focal-spot size of X-rays in the third moving picture imaging upon conclusion of the second moving picture imaging.

18. The X-ray diagnosis apparatus according to claim 1, further comprising:
a plurality of filters that attenuate X-rays generated from the X-ray tube; and
a filter driving unit that inserts at least one of the plurality of filters into an X-ray path from a focal point of X-rays in the X-ray tube to the X-ray detector; wherein
the processing circuitry is configured to select a filter to be inserted into the path from the plurality of filters based on at least one of a pixel size in the X-ray detector, a pixel size in an X-ray image based on an output of the X-ray detector, or a size of an X-ray irradiation area, and information regarding a body thickness of a subject.

19. An X-ray diagnosis apparatus comprising:
an X-ray tube that generates X-rays;
an X-ray detector that detects X-rays generated by the X-ray tube;
a plurality of filters that attenuate X-rays generated from the X-ray tube;
a filter driving unit that inserts at least one of the plurality of filters into an X-ray path from a focal point of the X-rays in the X-ray tube to the X-ray detector; and
processing circuitry is configured to select a filter to be inserted into the path from the plurality of filters based on at least one of a pixel size in the X-ray detector, a pixel size in an X-ray image based on an output of the X-ray detector, or a size of an X-ray irradiation area, and information regarding a body thickness of a subject.

20. The X-ray diagnosis apparatus according to claim 19, wherein
the processing circuitry is configured to select, if a pixel size in the X-ray detector is large, as a filter to be inserted into the path, a filter having a thickness larger than a filter selected in a case where a pixel size in the X-ray detector is small, based on the pixel size in the X-ray detector and the information regarding the body thickness of the subject.

* * * * *